United States Patent
Spidel et al.

(10) Patent No.: US 12,214,050 B2
(45) Date of Patent: *Feb. 4, 2025

(54) C-TERMINAL LYSINE CONJUGATED IMMUNOGLOBULINS

(71) Applicant: Eisai R&D Management Co., Ltd., Tokyo (JP)

(72) Inventors: Jared Spidel, Downingtown, PA (US); Earl Albone, Blue Bell, PA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 407 days.

This patent is subject to a terminal disclaimer.

(21) Appl. No.: 17/408,003

(22) Filed: Aug. 20, 2021

(65) Prior Publication Data

US 2022/0088212 A1 Mar. 24, 2022

Related U.S. Application Data

(63) Continuation of application No. 16/062,831, filed as application No. PCT/US2016/067165 on Dec. 16, 2016, now Pat. No. 11,135,304.

(60) Provisional application No. 62/269,138, filed on Dec. 18, 2015.

(51) Int. Cl.
| | |
|---|---|
| A61K 47/68 | (2017.01) |
| A61K 47/60 | (2017.01) |
| A61K 49/00 | (2006.01) |
| A61K 49/16 | (2006.01) |
| A61K 51/10 | (2006.01) |
| A61P 31/00 | (2006.01) |
| A61P 35/00 | (2006.01) |
| C07K 16/00 | (2006.01) |

(52) U.S. Cl.
CPC ......... *A61K 47/6811* (2017.08); *A61K 47/60* (2017.08); *A61K 47/6801* (2017.08); *A61K 47/6851* (2017.08); *A61K 47/6863* (2017.08); *A61K 47/6875* (2017.08); *A61K 47/6883* (2017.08); *A61K 47/6887* (2017.08); *A61K 47/6889* (2017.08); *A61K 49/0058* (2013.01); *A61K 49/16* (2013.01); *A61K 51/1087* (2013.01); *A61K 51/109* (2013.01); *A61K 51/1093* (2013.01); *A61K 51/1096* (2013.01); *A61P 31/00* (2018.01); *A61P 35/00* (2018.01); *C07K 16/00* (2013.01); *C07K 2317/14* (2013.01); *C07K 2317/31* (2013.01); *C07K 2317/40* (2013.01); *C07K 2317/522* (2013.01); *C07K 2317/526* (2013.01); *C07K 2317/528* (2013.01); *C07K 2317/55* (2013.01)

(58) Field of Classification Search
None
See application file for complete search history.

(56) References Cited

U.S. PATENT DOCUMENTS

| | | | |
|---|---|---|---|
| 9,359,400 B2 | 6/2016 | Usera et al. | |
| 10,941,431 B2* | 3/2021 | Spidel | A61K 47/6803 |
| 11,135,304 B2* | 10/2021 | Spidel | A61K 51/1096 |
| 11,753,669 B2* | 9/2023 | Spidel | C12P 21/02 |
| | | | 424/179.1 |
| 2013/0230543 A1 | 9/2013 | Pons et al. | |
| 2015/0017192 A1 | 1/2015 | Usera et al. | |
| 2017/0043033 A1 | 2/2017 | Strop et al. | |
| 2021/0171998 A1 | 6/2021 | Spidel et al. | |

FOREIGN PATENT DOCUMENTS

| | | |
|---|---|---|
| JP | 2015-209426 A | 11/2015 |
| RU | 2385879 C2 | 4/2010 |
| WO | 2005/070468 A2 | 8/2005 |
| WO | 2013/176516 A1 | 11/2013 |
| WO | 2014/159579 A1 | 10/2014 |
| WO | 2015/015448 A2 | 2/2015 |
| WO | 2015/162563 A1 | 10/2015 |
| WO | 2017/106643 A1 | 6/2017 |
| WO | 2017/213267 A1 | 12/2017 |

OTHER PUBLICATIONS

U.S. Appl. No. 16/062,831, filed Jun. 15, 2018, U.S. Pat. No. 11,135,304, Issued.
U.S. Appl. No. 15/662,981, filed Jul. 28, 2017, U.S. Pat. No. 10,941,431, Issued.
U.S. Appl. No. 17/159,655, filed Jan. 27, 2021, 2021-0171998, Published.
Behrens et al., Methods for site-specific drug conjugation to antibodies. MAbs. Jan.-Feb. 2014;6(1):46-53.
Dennler et al., Transglutaminase-based chemo-enzymatic conjugation approach yields homogeneous antibody-drug conjugates. Bioconjug Chem. Mar. 19, 2014;25(3):569-78.
Deonarain et al., Emerging formats for next-generation antibody drug conjugates. Expert Opin Drug Discov. May 2015;10(5):463-81.
Edwards et al., The remarkable flexibility of the human antibody repertoire; isolation of over one thousand different antibodies to a single protein, BLyS. J Mol Biol. 2003;334(1):103-118.
Groenen et al., The amine-donor substrate specificity of tissue-type transglutaminase. Influence of amino acid residues flanking the amine-donor lysine residue. Eur J Biochem. Mar. 15, 1994;220(3):795-9.
Gundersen et al., Microbial transglutaminase displays broad acyl-acceptor substrate specificity. Appl Microbiol Biotechnol. Jan. 2014;98(1):219-30.
Harris, Processing of C-terminal lysine and arginine residues of proteins isolated from mammalian cell culture. J Chromatogr A. Jun. 23, 1995;705(1):129-34.

(Continued)

*Primary Examiner* — Phuong Huynh
(74) *Attorney, Agent, or Firm* — McCarter & English, LLP; Marcie B. Clarke; Yelena Margolin

(57) ABSTRACT

Provided herein are conjugated immunoglobulins and methods for generating conjugated immunoglobulins using a microbial transglutaminase.

13 Claims, 15 Drawing Sheets

Specification includes a Sequence Listing.

(56) References Cited

OTHER PUBLICATIONS

Jeger et al., Site-specific and stoichiometric modification of antibodies by bacterial transglutaminase. Angew Chem Int Ed Engl. Dec. 17, 2010;49(51):9995-7.
Josten et al., Use of microbial transglutaminase for the enzymatic biotinylation of antibodies. J Immunol Methods. Jun. 23, 2000;240(1-2):47-54.
Kline et al., Methods to Make Homogenous Antibody Drug Conjugates. Pharm Res. Nov. 2015;32(11):3480-93.
Lloyd et al., Modelling the human immune response: performance of a 1011 human antibody repertoire against a broad panel of therapeutically relevant antigens. Protein Eng Des Sel. 2009;22(3):159-168.
McCombs et al., Antibody drug conjugates: design and selection of linker, payload and conjugation chemistry. AAPS J. Mar. 2015;17(2):339-51.
Mindt et al., Modification of different IgG1 antibodies via glutamine and lysine using bacterial and human tissue transglutaminase. Bioconjug Chem. Jan. 2008;19(1):271-8.
Ohtsuka et al., Comparison of substrate specificities of transglutaminases using synthetic peptides as acyl donors. Biosci Biotechnol Biochem. Dec. 2000;64(12):2608-13.
Ohtsuka et al., Substrate specificities of microbial transglutaminase for primary amines. J Agric Food Chem. Dec. 2000;48(12):6230-3.
Senter et al., The discovery and development of brentuximab vedotin for use in relapsed Hodgkin lymphoma and systemic anaplastic large cell lymphoma. Nat Biotechnol. Jul. 10, 2012;30(7):631-7.
Siegmund et al., Locked by Design: A Conformationally Constrained Transglutaminase Tag Enables Efficient Site-Specific Conjugation. Angew Chem Int Ed Engl. Nov. 2, 2015;54(45):13420-4.
Sochaj et al., Current methods for the synthesis of homogeneous antibody-drug conjugates. Biotechnol Adv. Nov. 1, 2015;33(6 Pt 1):775-84.
Sorensen et al., Polymerization of IgA and IgM: roles of Cys309/Cys414 and the secretory tailpiece. J Immunol. 1999;162(6):3448-3455.
Spidel et al., Site-Specific Conjugation to Native and Engineered Lysines in Human Immunoglobulins by Microbial Transglutaminase. Bioconjug Chem. Sep. 20, 2017;28(9):2471-84.
Strop et al., Location matters: site of conjugation modulates stability and pharmacokinetics of antibody drug conjugates. Chem Biol. Feb. 21, 2013;20(2):161-7.
Sugimura et al., Identification of preferred substrate sequences of microbial transglutaminase from Streptomyces mobaraensis using a phage-displayed peptide library. Arch Biochem Biophys. Sep. 15, 2008;477(2):379-83.
Tagami et al., Substrate specificity of microbial transglutaminase as revealed by three-dimensional docking simulation and mutagenesis. Protein Eng Des Sel. Dec. 2009;22(12):747-52.
Taguchi et al., Substrate specificity analysis of microbial transglutaminase using proteinaceous protease inhibitors as natural model substrates. J Biochem. Sep. 2000;128(3):415-25.
Tol et al., Chemotherapy, bevacizumab, and cetuximab in metastatic colorectal cancer [published correction appears in N Engl J Med. Dec. 23, 2010;363(26):2573]. N Engl J Med. 2009;360(6):563-572.
Van Den Bremer et al., Human IgG is produced in a pro-form that requires clipping of C-terminal lysines for maximal complement activation. MAbs. 2015;7(4):672-80.
International Search Report and Written Opinion for Application No. PCT/JP2017/021672, dated Sep. 14, 2017. 11 pages.
International Search Report and Written Opinion for Application No. PCT/US2016/067165, dated May 2, 2017. 8 pages.
Dennler et al., Antibody Conjugates: From Heterogeneous Populations to Defined Reagents. Antibodies. 2015;4(3):197-224.
Schibli, Microbial transglutaminase for site-specific protein conjugation. Zedira, retrieved online at: https://zedira.com/ISO-9001. 7 pages, Aug. 17, 2015.

\* cited by examiner

FIGURE 2
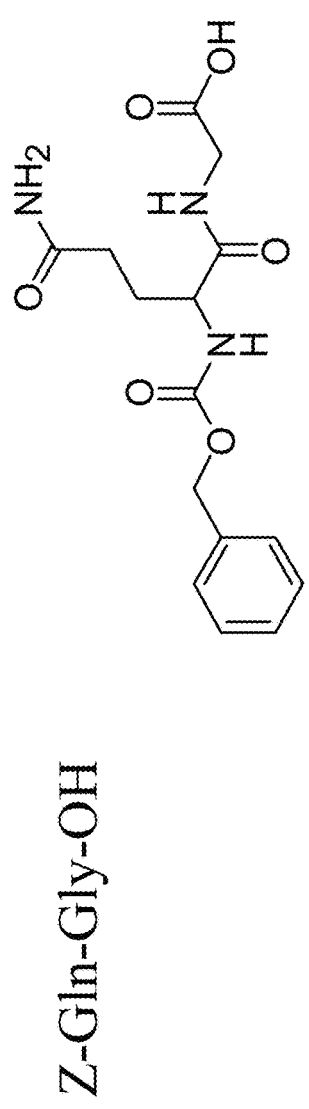
Z-Gln-Gly-OH
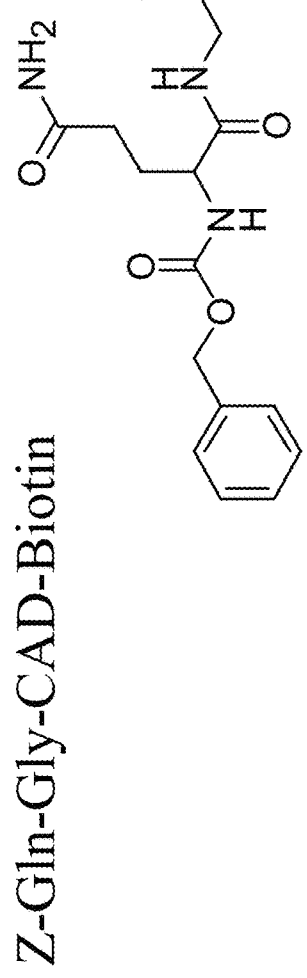
Z-Gln-Gly-CAD-Biotin

FIGURE 2 (cont.)
Z-Gln-Gly-PEG₃-BCN
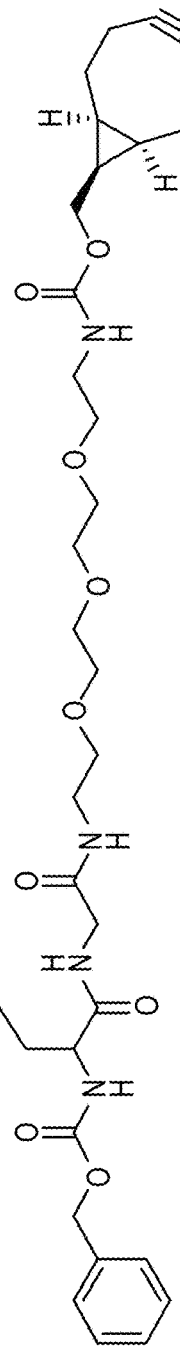
Z-Gln-Gly-N₃
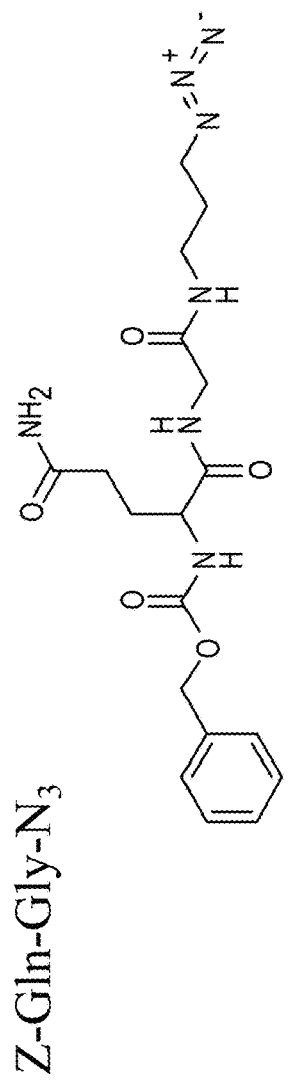
Z-Gln-Gly-PEG₂-Auristatin F
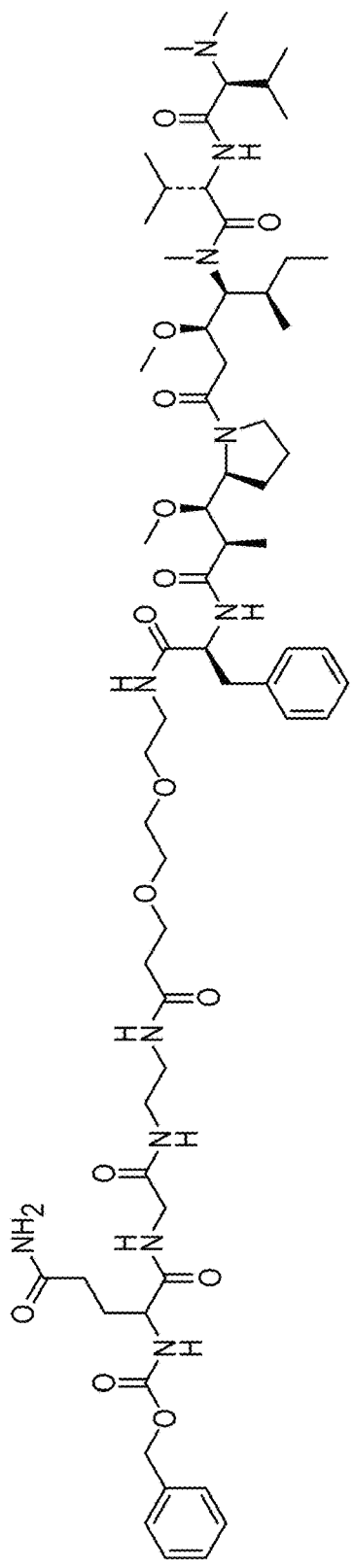

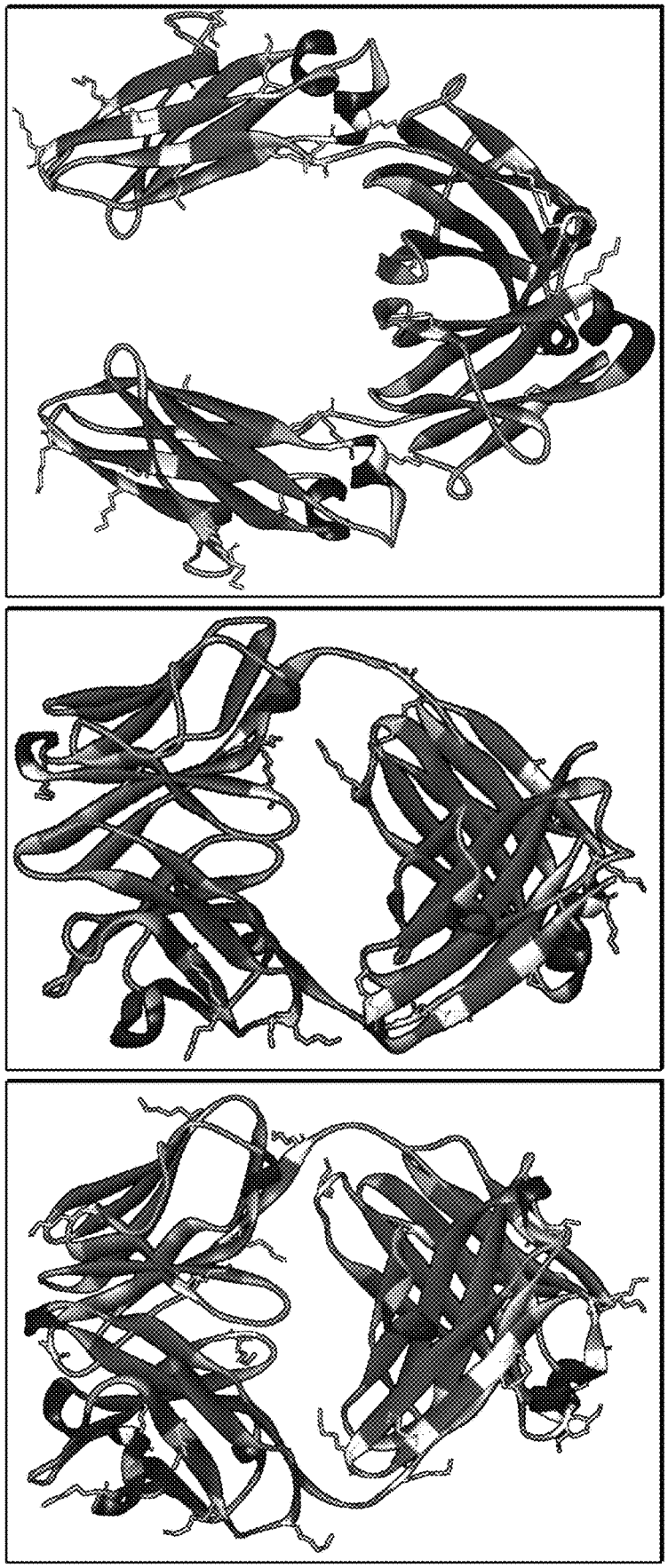

FIGURE 5

```
hu Cγ
118
ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP
218
KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK
318
EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW
418                                   447
QQGNVFSCSV MHEALHNHYT QKSLSLSPGK hu Cκ
108
RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK
208
SFNRGEC hu Cλ
110
GQPKAAPSVT LFPPSSEELQ ANKATLVCLI SDFYPGAVTV AWKADSSPVK AGVETTTPSK QSNNKYAASS YLSLTPEQWK SHKSYSCQVT HEGSTVEKTV
210
APTECS
```

Antibody 02

Antibody 03

Antibody 01

Antibody 04

Antibody 05

Antibody 06

C-TERMINAL LYSINE CONJUGATED IMMUNOGLOBULINS

RELATED APPLICATIONS

This application is a continuation of U.S. patent application Ser. No. 16/062,831, filed on Jun. 15, 2021, now U.S. Pat. No. 11,135,304, issued on Oct. 5, 2021, which is a 35 U.S.C. § 371 national stage filing of International Application No. PCT/US2016/067165, filed on Dec. 16, 2016, which, in turn, claims priority to U.S. Provisional Application No. 62/269,138, filed on Dec. 18, 2015. The entire contents of the foregoing applications are expressly incorporated herein by reference.

TECHNICAL FIELD

Provided herein are C-terminal lysine conjugated immunoglobulins and methods of creating the same.

SEQUENCE LISTING

The instant application contains a Sequence Listing which has been submitted electronically in ASCII format and is hereby incorporated by reference in its entirety. Said ASCII copy, created on Jun. 15, 2018, is named 118557-03803_SL.txt and is 13,252 bytes in size.

BACKGROUND

The utility of monoclonal antibodies extends from basic research to therapeutic and diagnostic applications. The ability to conjugate antibodies to functional agents extends their functionality even further. The manufacture of conjugated antibodies usually involves conjugation of a linker, drug, or other functional agent to reactive lysine cysteine residues on the heavy (HC) and light (LC) chains of a monoclonal antibody (mAb). See Deonarain, et al., "Emerging formats for next-generation antibody drug conjugates", Expert Opinion in Drug Discovery (2015), 10(5): 463-481. Lysine conjugation is typically mediated by succinimide (NHS)-based or isothiocyanate-based chemistry. Cysteine-based conjugation requires partial reduction of the antibody to break some of the interchain disulfide bonds, thereby creating free thiol side chains. Thiol-reactive functional agents can then react with the free thiol groups on the antibody to generate antibody-drug conjugates (ADCs). Both of these methods result in modification of multiple lysines or cysteines leading to heterogeneous mixtures of ADCs with a distribution of drug-to-antibody (DAR) ratios and drug modifications at random positions.

A recent push to utilize site-specific conjugation technologies as a way to produce a homogeneous ADC product with a defined DAR has yielded several methods including engineering unpaired cysteines, incorporation of non-natural amino acids, and site-specific enzymatic modification. While these methods produce homogeneous products, they each have their disadvantages. Cysteine-based conjugation requires an added step to remove a capping cysteine, glutathione, or even a light chain from the unpaired cysteine. See, e.g., Junutula, et al., "Site-Specific Conjugation of a Cytotoxic Drug to an Antibody Improves Therapeutic Index", Nature Biotechnology, (2008) 26:925-932; Chen, et al., "Charge-based Analysis of Antibodies with Engineered Cysteines", MAbs (2009) 1(6): 563-571; Gomez, et al., "Effect of temperature, pH, dissolved oxygen, and hydrolysate on the formation of triple light chain antibodies in cell culture" Biotechnol Progress (2010), 26: 1438-1445. Further, serum instability of maleimide-based chemistry currently used for cysteine-based conjugates has been demonstrated raising concerns for loss in potency or off-target toxicity. Alley, et al., "Contribution of Linker Stability to the Activities of Anticancer Immunoconjugates", Bioconjugate Chemistry (2008) 19(3): 759-765; Shen, et al., "Conjugation site modulates the in vivo stability and therapeutic activity of antibody-drug conjugates", Nature Biotechnology (2012) 30: 184-189. Incorporation of non-natural amino acids requires expression in either a genetically modified cell-based or cell-free system. Hallam, et al., "Unnatural Amino Acids in Novel Antibody Conjugates", Future Med. Chem. (2014) 6(11): 1309-1324. Further, the presence of an unnatural amino acid could trigger an immunogenic response in patients. Site-specific enzymatic modifications, however, could potentially utilize a native, wild-type amino acid in the antibody sequence, thereby minimizing the chance for immunogenicity. Further, the post-translational bonds typically formed by protein-modifying enzymes are very stable.

Site-specific enzymatic modification of proteins has been explored using a family of proteins called transglutaminases that catalyze the formation of a stable isopeptide bond between the γ-carboxyamide group (acyl donor) of a glutamine and the ε-amino group (acyl acceptor) of a lysine (see FIG. 1) (see, e.g., Yokoyama, et al., "Properties and Applications of Microbial Transglutaminase", Appl. Microbiol. Biotech. (2004) 64: 47-454; Strop, "Versatility of Microbial Transglutaminase", Bioconjugate Chemistry, (2014) 25(5): 855-862; Kieliszek et al., "Microbial Transglutaminase and its Application in the Food Industry", Folia Microbiol (2014) 59:241-250). Recently, several groups have explored utilizing transglutaminase as a means to produce ADCs (see, e.g., Josten et al., "Use of Microbial Transglutaminase for the Enzymatic Biotinylation of Antibodies", J. Immunol Methods, (2000) 240:47-54; Mindt et al., "Modification of Different IgG1 Antibodies via Glutamine and Lysine Using Bacterial and Human Tissue Transglutaminase", Bioconjugate Chemistry (2008) 19(1): 271-278); Jeger, et al., "Site-specific and stoichiometric modification of antibodies by bacterial transglutaminase" Angew. Chem. Int. Ed. Engl. (2010) 49: 9995-9997; Strop et al., "Location Matters: Site of Conjugation Modulates Stability and Pharmacokinetics of Antibody Drug Conjugates", Chem Biol (2013) 20(2):161-167; Dennler et al., "Transglutaminase-Based Chemo-Enzymatic Conjugation Approach Yields Homogeneous Antibody-Drug Conjugates", Bioconjugate Chemistry (2014) 25(3): 569-578; Siegmund, et al., "Locked by Design: A Conformationally Constrained Transglutaminase Tag Enables Efficient Site-Specific Conjugation", Angew. Chem. Int. Ed. Engl. (2015) 54(45):13420-13424). Transglutaminases are found in organisms ranging from bacteria through humans that are structurally and functionally related, yet each is involved in specific cellular processes. A microbial transglutaminase (microbial transglutaminase) isolated from the bacterium *Streptomyces mobaraensis* has been used extensively throughout the food industry to crosslink proteins together for various applications. Besides its low manufacturing cost, it is an attractive conjugation technique due to its ability to function under a wide range of pH, salt, and temperature conditions.

Despite over two decades of research, the substrate specificity of microbial transglutaminase has not been clearly defined. In general, glutamines or lysines on exposed loops with hydrophobic or positively charged adjacent residues tend to be preferred. See, Taguchi et al., "Substrate specificity analysis of microbial transglutaminase using proteinaceous protease inhibitors as natural model substrates", J. Biochem. (2000) 128:415-425; Sugimura et al., "Identification of preferred substrate sequences of microbial transglutaminase from *Streptomyces mobaraensis* using a phage-displayed peptide library", Arch. Biochem. Biophys. (2008) 477:379-383; Tagami et al., "Substrate specificity of microbial transglutaminase as revealed by three-dimensional docking simulation and mutagenesis", Protein Eng. Des. Sel. (2009) 22:747-752. The context of the acyl donor glutamine has been found to be more critical than the acyl acceptor lysine. See, e.g., Ohtsuka et al., "Substrate specificities of microbial transglutaminase for primary amines", J. Agric. Food Chem. (2000) 48: 6230-6233; Ohtsuka et al., "Comparison of substrate specificities of transglutaminases using synthetic peptides as acyl donors", Biosci. Biotechnol. Biochem. (2000) 64: 2608-2613; Gundersen et al., "Microbial transglutaminase displays broad acyl-acceptor substrate specificity", Appl. Microbiol. Biotechnol. (2013) 98:219-230.

Due to a lower specificity for the acyl acceptor amine by microbial transglutaminase, research thus far has been focused only on transamidation of antibody glutamine residues. See, Josten et al., Mindt et al., Jeger et al., Strop et al., Dennler et al., and Siegmund et al., referenced above. Human IgG is comprised of an average of 80 lysines, of which 80-90% are predicted to be solvent exposed (Gautier et al., "Lysine Conjugated Properties in Human IgGs Studied by Integrating High-Resolution Native Mass Spectrometry and Bottom-Up Proteomics", Proteomics (2015) 15(16):2756-2765; data not shown), and the C-terminal codon of $IgG_1$, $IgG_2$, $IgG_3$, and $IgG_4$ is a lysine (Ellison et al., DNA (1981) 1:11-18; Ellison et al. ("Ellison et al. 2"), Proc. Nat. Acad. Sci. USA, (1982) 79:1984-1988; Ellison et al., Nucleic Acid Res. (1982) 10:4071-4079). However, serum-derived IgG lacks the lysine (Wang et al., J. Immunol. (1980) 125:1048-1054; Edelman et al., Proc Natl Acad. Sci. USA (1969) 63:78-85; Frangione et al., Biochemistry (1980) 19:4304-4308; Pink et al., Biochem. J. (1970) 117:33-47). The same has been observed for IgD (White et al., Science (1985) 228:733-737; Lin et al., Proc. Natl. Acad. Sci. USA, (1981) 78:504-508; Shinoda et al., Proc. Natl. Acad. Sci. USA (1981) 78:785-789). Recombinant expression of IgG1 in HEK293 and CHO cells also results in a protein lacking the C-terminal Lys447 (Ellison et al.; Harris et al., Eur. J. Biochem. (1990) 194:611-620; Harris, J. Chromatogr. A (1995) 705:129-134; Dick et al., Biotechnol. Bioeng. (2008) 100:1132-1143).

To date, those of ordinary skill in the art thought that utilizing an amine donor-based substrate to transamidate a lysine may yield a heterogeneous ADC product due to the plethora of reactive lysines on the surface of an IgG (Josten et al. and Jeger et al.) and, thus, use of an amine donor-based substrate to transamidate lysine residues on immunoglobulins has been discouraged.

Thus, there exists a need for site-specific enzymatic modifications of immunoglobulins to create conjugates which have a predictable rate of conjugation. This will allow for creation of ADCs with a relatively homologous DAR.

SUMMARY

The instant invention surprisingly discloses that, while no modification of wild-type immunoglobulin lysines by microbial transglutaminase was observed, when a C-terminal immunoglobulin lysine residue was protected from cleavage by carboxypeptidases using a C-terminal amino acid extension, microbial transglutaminase was able to utilize the native C-terminal lysine as an acyl acceptor. Surprisingly, conjugation of the C-terminal lysine using microbial transglutaminase lead to site-specific and predictable incorporation of conjugated functional agents.

In one aspect, disclosed herein is a method for generating a conjugated immunoglobulin, the method comprising incubating an immunoglobulin with a microbial transglutaminase and a functional agent comprising an acyl donor substrate, wherein the immunoglobulin comprises at least one amino acid residue after a C-terminal lysine, wherein the acyl donor substrate comprises a glutamine residue, and wherein the functional agent is a therapeutic agent or a diagnostic agent, wherein the microbial transglutaminase conjugates the C-terminal lysine of the immunoglobulin to the glutamine residue of the acyl donor substrate on the functional agent, thereby generating the conjugated immunoglobulin.

In another aspect, disclosed herein is a method for generating a conjugated immunoglobulin, the method comprising i) incubating an immunoglobulin with a microbial transglutaminase and an acyl donor substrate, wherein the immunoglobulin comprises at least one amino acid residue after a C-terminal lysine, and wherein the acyl donor substrate comprises a glutamine residue and a reactive group, wherein the microbial transglutaminase conjugates the C-terminal lysine of the immunoglobulin to the glutamine residue of the acyl donor substrate, and ii) conjugating a functional agent to the reactive group of the acyl donor substrate, wherein the functional agent is a therapeutic agent or a diagnostic agent, thereby generating the conjugated immunoglobulin.

In one embodiment, the reactive group of the acyl donor substrate is conjugated to the functional agent by click chemistry.

In one embodiment, the C-terminal lysine is Lysine 447 (K447) on a heavy chain of the immunoglobulin.

In one embodiment, the immunoglobulin comprises one amino acid residue after the C-terminal lysine, and the one amino acid residue after the C-terminal lysine is glycine, alanine, valine, leucine, isoleucine, methionine, phenylalanine, tyrosine, tryptophan, serine, threonine, cysteine, asparagine, glutamine, or histidine. In another embodiment, the immunoglobulin comprises one amino acid residue after the C-terminal lysine, and wherein the one amino acid residue after the C-terminal lysine does not comprise proline, aspartic acid, glutamic acid, lysine, or arginine.

In one embodiment, the functional agent comprising the acyl donor substrate is according to one Formulae (I) or (II):

$$(Z)_m\text{-Gln-}(L)_n\text{-}(Y) \qquad (I)$$

$$(Y)\text{-}(L)_n\text{-Gln-}(Z)_m \qquad (II)$$

wherein Z is a carboxylbenzyloxy (CBZ) group or an amino acid residue; Gln is a glutamine amino acid residue; each L is independently a straight or branched linker from 1 to 20 carbon atoms, wherein one or more of the carbon atoms may be optionally and independently replaced with a nitrogen, oxygen or sulfur atom, and wherein each carbon and nitrogen atom may be optionally substituted; or each L is optionally and independently an amino acid residue; m is an integer from 0 to 5; n is an integer from 0 to 5; and Y is a functional agent.

In one embodiment, the functional agent comprising the acyl donor substrate is according to formula (I), and wherein Z is a CBZ group; wherein L is a polyethylene glycol moiety (PEG) (—O(($CH_2$)$_2$)—), ethyl amine (—NH(($CH_2$)$_2$)—) or propyl amine (—NH(($CH_2$)$_3$)—); and wherein n is 0, 1, 2 or 3. In one embodiment, L is a polyethylene glycol moiety (PEG). In another embodiment, L comprises one or more amino acids and a polyethylene glycol moiety (PEG). In another embodiment, the functional agent comprising the acyl donor substrate is according to formula (I), wherein Z is a CBZ group, and wherein L is an amino acid. In one embodiment, L is Gly; m is 1; and n is 1. In another embodiment, the functional agent comprising the acyl donor substrate is according to formula (II), wherein Z is a CBZ group; m is 1; n is 2, 3 or 4; and at least one L is Gly; and at least one L is a PEG moiety. In a further embodiment, the functional agent comprising the acyl donor substrate is according to formula (II), wherein Z is a CBZ group; m is 1; n is 4; one L is Gly and the remaining three L groups are each PEG moieties.

In one embodiment, the acyl donor substrate is according to one Formulae (III) or (IV):

$(Z)_m\text{-Gln-}(L)_n\text{-}(X)$  (III)

$(X)\text{-}(L)_n\text{-Gln-}(Z)_m$  (IV)

wherein Z is a carboxylbenzyloxy (CBZ) group or an amino acid residue; Gln is a glutamine amino acid residue; each L is independently a straight or branched linker from 1 to 20 carbon atoms, wherein one or more of the carbon atoms may be optionally and independently replaced with a nitrogen, oxygen or sulfur atom, and wherein each carbon and nitrogen atom may be optionally substituted; or each L is optionally and independently an amino acid residue; m is an integer from 0 to 5; n is an integer from 0 to 5; and X is a reactive group.

In one embodiment, L is a polyethylene glycol moiety (PEG). In another embodiment, when n is 2-5, at least one L comprises one or more amino acids and another L is a polyethylene glycol (PEG) moiety. In one embodiment, the acyl donor substrate is according to formula (III), and wherein Z is a CBZ group; wherein L is a polyethylene glycol moiety (PEG) (—O((CH$_2$)$_2$)—), ethyl amine (—NH((CH$_2$)$_2$)—) or propyl amine (—NH((CH$_2$)$_3$)—); and wherein n is 0, 1, 2 or 3. In another embodiment, the acyl donor substrate is according to formula (III), wherein Z is a CBZ group, and wherein L is an amino acid. In one embodiment, L is Gly; n is 1; and m is 1. In another embodiment, the acyl donor substrate is according to formula (IV), wherein Z is a CBZ group; m is 1; n is 1, 2 or 3; and at least one L is Gly.

In another embodiment, X is a reactive group selected from the group consisting of (1R,8S,9s)-bicyclo[6.1.0]non-4-yn-9-ylmethanol (BCN),

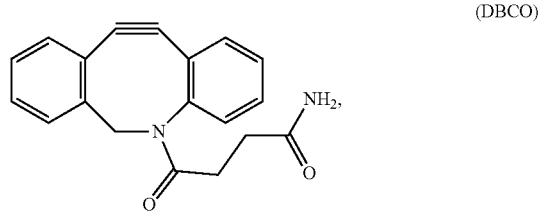 [SMILES: NC(=O)CCC(=O)N1Cc2ccccc2C#Cc2ccccc21]

(DBCO)

trans-cyclooctene (TCO), azido (N$_3$), alkyne, tetrazine methylcyclopropene, norbornene, hydrazide/hydrazine, and aldehyde.

In one embodiment, the therapeutic agent is an antibody or antigen-binding portion thereof, a chemotherapeutic agent, a drug agent, a radioactive agent, a cytotoxic agent, an antibiotic, a small molecule, a nucleic acid, or a polypeptide. In another embodiment, the diagnostic agent is a fluorophore, a fluorescent dye, a radionuclide, or an enzyme.

In one embodiment, the immunoglobulin has two amino acid residues after the C-terminal lysine, comprising a first amino acid residue after the C-terminal lysine and a second amino acid residue after the C-terminal lysine. In one embodiment, the first amino acid residue after the C-terminal lysine is any amino acid residue except aspartic acid, glutamic acid, or proline, and wherein the second amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In another embodiment, the first amino acid residue after the C-terminal lysine is lysine or arginine. In another embodiment, the first amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine.

In one embodiment, the immunoglobulin has three amino acid residues after the C-terminal lysine, comprising a first amino acid residue after the C-terminal lysine, a second amino acid residue after the C-terminal lysine, and a third amino acid residue after the C-terminal lysine, wherein the third amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is not aspartic acid, glutamic acid, or proline. In one embodiment, the first amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the second amino acid residue after the C-terminal lysine is not aspartic acid, glutamic acid, or proline. In one embodiment, the second amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine.

In one embodiment, the immunoglobulin has four amino acid residues after the C-terminal lysine, comprising a first amino acid residue after the C-terminal lysine, a second amino acid residue after the C-terminal lysine, a third amino acid residue after the C-terminal lysine, and a fourth amino acid residue after the C-terminal lysine, wherein the fourth amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is not aspartic acid, glutamic acid, or proline. In one embodiment, the first amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the second amino acid residue after the C-terminal lysine is not aspartic acid, glutamic acid, or proline. In one embodiment, the second amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the third amino acid residue after the C-terminal lysine is not aspartic acid, glutamic acid, or proline. In one embodiment, the third amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine.

In one embodiment, the immunoglobulin has five amino acid residues after the C-terminal lysine, comprising a first amino acid residue after the C-terminal lysine, a second amino acid residue after the C-terminal lysine, a third amino acid residue after the C-terminal lysine, a fourth amino acid residue after the C-terminal lysine, and a fifth amino acid residue after the C-terminal lysine, wherein the fifth amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is not aspartic acid, glutamic acid, or proline. In one embodiment, the first amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the second amino acid residue after the C-terminal lysine is not aspartic acid, glutamic acid, or proline. In one embodiment, the second amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the third amino acid residue after the C-terminal lysine is not aspartic acid, glutamic acid, or proline. In one embodiment, the third amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the fourth amino acid residue after the C-terminal lysine is not aspartic acid, glutamic acid, or proline. In one embodiment, the fourth amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine.

In one embodiment, the immunoglobulin has less than 9 amino acid residues after the C-terminal lysine, and wherein the last amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine.

In one embodiment, the immunoglobulin has less than 13 amino acid residues after the C-terminal lysine, and wherein the last amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine.

In one embodiment, the microbial transglutaminase is from *Streptomyces mobarensis*.

In one embodiment, the immunoglobulin is an $IgG_1$ immunoglobulin. In another embodiment, the immunoglobulin is an $IgG_2$, $IgG_3$, or $IgG_4$ immunoglobulin. In one embodiment, the immunoglobulin is an $IgA_1$, an $IgA_2$, or an IgM immunoglobulin which does not comprise a tailpiece. In one embodiment, the immunoglobulin is an IgD or IgE, immunoglobulin.

In one embodiment, the immunoglobulin is a human immunoglobulin or a humanized immunoglobulin. In one embodiment, the immunoglobulin is a chimeric immunoglobulin or a non-human immunoglobulin.

In one embodiment, the immunoglobulin comprises two heavy chains and two light chains. In one embodiment, there is no intramolecular cross-linking between the two heavy chains of the immunoglobulin.

In one embodiment, the ratio of functional agent to immunoglobulin is 1:1 to 2:1.

In another aspect, described herein is a conjugated immunoglobulin comprising an immunoglobulin and a functional agent, wherein the immunoglobulin comprises at least one amino acid residue after a C-terminal lysine, the functional agent comprises an acyl donor substrate, wherein the acyl donor substrate comprises a glutamine residue, and the functional agent is a therapeutic agent or a diagnostic agent, wherein the C-terminal lysine of the immunoglobulin is conjugated to the glutamine residue of the acyl donor substrate of the functional agent.

In another aspect, described herein is a conjugated immunoglobulin comprising an immunoglobulin and a functional agent, wherein the immunoglobulin comprises at least one amino acid residue after a C-terminal lysine, the C-terminal lysine is conjugated to a glutamine residue on an acyl donor substrate, wherein the acyl donor substrate further comprises a reactive group, the reactive group is conjugated to a functional agent, wherein the functional agent is a therapeutic agent or a diagnostic agent.

In one embodiment, the C-terminal lysine is Lysine 447 (K447) on a heavy chain of the immunoglobulin.

In one embodiment, the immunoglobulin comprises one amino acid residue after the C-terminal lysine, and wherein the one amino acid residue after the C-terminal lysine is glycine, alanine, valine, leucine, isoleucine, methionine, phenylalanine, tyrosine, tryptophan, serine, threonine, cysteine, asparagine, glutamine, or histidine.

In another embodiment, the immunoglobulin comprises one amino acid residue after the C-terminal lysine, and wherein the one amino acid residue after the C-terminal lysine is not proline, aspartic acid, glutamic acid, lysine, or arginine.

In one embodiment, the functional agent comprising the acyl donor substrate is according to one Formulae (I) or (II):

$(Z)_m$-Gln-$(L)_n$-(Y)  (I)

(Y)-$(L)_n$-Gln-$(Z)_m$  (II)

wherein Z is a carboxylbenzyloxy (CBZ) group or an amino acid residue; Gln is a glutamine amino acid residue; each L is independently a straight or branched linker from 1 to 20 carbon atoms, wherein one or more of the carbon atoms may be optionally and independently replaced with a nitrogen, oxygen or sulfur atom, and wherein each carbon and nitrogen atom may be optionally substituted; or each L is optionally and independently an amino acid residue; m is an integer from 0 to 5; n is an integer from 0 to 5; and Y is a functional agent.

In one embodiment, the functional agent comprising the acyl donor substrate is according to formula (I), and wherein Z is a CBZ group; wherein L is a polyethylene glycol moiety (PEG) (—O((CH$_2$)$_2$)—), ethyl amine (—NH((CH$_2$)$_2$)—) or propyl amine (—NH((CH$_2$)$_3$)—); and wherein n is 0, 1, 2 or 3. In another embodiment, the functional agent comprising the acyl donor substrate is according to formula (I), wherein Z is a CBZ group, and wherein L is an amino acid. In one embodiment, L is Gly; m is 1; and n is 1. In one embodiment, the functional agent comprising the acyl donor substrate is according to formula (II), wherein Z is a CBZ group; m is 1; n is 1, 2 or 3; and at least one L is Gly. In one embodiment, L is a polyethylene glycol moiety (PEG). In another embodiment, L comprises one or more amino acids and a polyethylene glycol moiety (PEG).

In one embodiment, the acyl donor substrate is according to one Formulae (III) or (IV):

(Z)$_m$-Gln-(L)$_n$-(X)          (III)

(X)-(L)$_n$-Gln-(Z)$_m$          (IV)

wherein Z is a carboxylbenzyloxy (CBZ) group or an amino acid residue; Gln is a glutamine amino acid residue; each L is independently a straight or branched linker from 1 to 20 carbon atoms, wherein one or more of the carbon atoms may be optionally and independently replaced with a nitrogen, oxygen or sulfur atom, and wherein each carbon and nitrogen atom may be optionally substituted; or each L is optionally and independently an amino acid residue; m is an integer from 0 to 5; n is an integer from 0 to 5; and X is a reactive group.

In one embodiment, the acyl donor substrate is according to formula (III), and wherein Z is a CBZ group; wherein L is a polyethylene glycol moiety (PEG) (—O((CH$_2$)$_2$)—), ethyl amine (—NH((CH$_2$)$_2$)—) or propyl amine (—NH((CH$_2$)$_3$)—); and wherein n is 0, 1, 2 or 3. In another embodiment, the acyl donor substrate is according to formula (III), wherein Z is a CBZ group, and wherein L is an amino acid. In one embodiment, L is Gly; m is 1; and n is 1. In another embodiment, the acyl donor substrate is according to formula (IV), wherein Z is a CBZ group; m is 1; n is 1, 2 or 3; and at least one L is Gly. In one embodiment, L is a polyethylene glycol moiety (PEG). In another embodiment, when n is 2-5, then at least one L comprises one or more amino acids and one or more L comprises a polyethylene glycol moiety (PEG).

In one embodiment, X is a reactive group selected from the group consisting of (1R,8S,9s)-bicyclo[6.1.0]non-4-yn-9-ylmethanol (BCN),

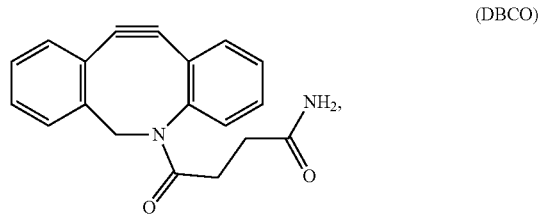 [SMILES: NC(=O)CCC(=O)N1Cc2ccccc2C#Cc2ccccc21]
(DBCO)

trans-cyclooctene (TCO), azido (N$_3$), alkyne, tetrazine methylcyclopropene, norbornene, hydrazide/hydrazine, and aldehyde.

In one embodiment, the therapeutic agent is an antibody or antigen-binding portion thereof, a chemotherapeutic agent, a drug agent, a radioactive agent, a cytotoxic agent, an antibiotic, a small molecule, nucleic acid, or a polypeptide. In another embodiment, the diagnostic agent is a fluorophore, a fluorescent dye, a radionuclide, or an enzyme.

In one embodiment, the immunoglobulin has two amino acid residues after the C-terminal lysine, comprising a first amino acid residue after the C-terminal lysine and a second amino acid residue after the C-terminal lysine.

In one embodiment, the first amino acid residue after the C-terminal lysine is any amino acid residue except aspartic acid, glutamic acid, or proline, and wherein the second amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is lysine or arginine.

In one embodiment, the immunoglobulin has three amino acid residues after the C-terminal lysine, comprising a first amino acid residue after the C-terminal lysine, a second amino acid residue after the C-terminal lysine, and a third amino acid residue after the C-terminal lysine, wherein the third amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is not aspartic acid, glutamic acid, or proline. In one embodiment, the first amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the second amino acid residue after the C-terminal lysine is not aspartic acid, glutamic acid, or proline. In one embodiment, the second amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine.

In one embodiment, the immunoglobulin has four amino acid residues after the C-terminal lysine, comprising a first amino acid residue after the C-terminal lysine, a second amino acid residue after the C-terminal lysine, a third amino acid residue after the C-terminal lysine, and a fourth amino acid residue after the C-terminal lysine, wherein the fourth amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is not aspartic acid, glutamic acid, or proline. In one embodiment, the first amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the second amino acid residue after the C-terminal lysine is not aspartic acid, glutamic acid, or proline. In one embodiment, the second amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the third amino acid residue after the C-terminal lysine is not aspartic acid, glutamic acid, or proline. In one embodiment, the third amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine.

In one embodiment, the immunoglobulin has five amino acid residues after the C-terminal lysine, comprising a first amino acid residue after the C-terminal lysine, a second amino acid residue after the C-terminal lysine, a third amino acid residue after the C-terminal lysine, a fourth amino acid residue after the C-terminal lysine, and a fifth amino acid residue after the C-terminal lysine, wherein the fifth amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is not aspartic acid, glutamic acid, or proline. In one embodiment, the first amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the second amino acid residue after the C-terminal lysine is not aspartic acid, glutamic acid, or proline. In one embodiment, the second amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the third amino acid residue after the C-terminal lysine is not aspartic acid, glutamic acid, or proline. In one embodiment, the third amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine. In one embodiment, the fourth amino acid residue after the C-terminal lysine is not aspartic acid, glutamic acid, or proline. In one embodiment, the fourth amino acid residue after the C-terminal lysine is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine.

In one embodiment, the immunoglobulin has less than 9 amino acid residues after the C-terminal lysine, and wherein the last amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine.

In one embodiment, the immunoglobulin has less than 13 amino acid residues after the C-terminal lysine, and wherein the last amino acid residue after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine.

In one embodiment, the immunoglobulin is an $IgG_1$ immunoglobulin. In another embodiment, the immunoglobulin is an $IgG_2$, $IgG_3$, or $IgG_4$ immunoglobulin. In one embodiment, the immunoglobulin is an $IgA_1$, an $IgA_2$, or an IgM immunoglobulin which does not comprise a tailpiece. In one embodiment, the immunoglobulin is an IgD or IgE, immunoglobulin.

In one embodiment, the immunoglobulin is a human immunoglobulin or a humanized immunoglobulin. In one embodiment, the immunoglobulin is a chimeric immunoglobulin or a non-human immunoglobulin.

In one embodiment, the immunoglobulin comprises two heavy chain and two light chains. In one embodiment, there is no intramolecular cross-linking between the two heavy chains of the immunoglobulin.

In one embodiment, the ratio of functional agent to immunoglobulin is 1:1 to 2:1.

In one embodiment, the functional agent is an antibody, or antigen-binding portion thereof, and wherein the immunoglobulin and the functional agent bind the same antigen or bind different antigens.

In another aspect, described herein is a nucleic acid encoding a conjugated immunoglobulin. In another aspect, described herein is a plasmid comprising a nucleic acid. In another embodiment, described herein is an isolated cell comprising a plasmid.

In another aspect, described herein is a pharmaceutical composition comprising a conjugated immunoglobulin and a pharmaceutically acceptable carrier.

In one aspect, described herein is a conjugated immunoglobulin produced by any of the methods described herein.

In one embodiment, the method further comprises a step of purifying the immunoglobulin conjugated to the glutamine residue of the acyl donor substrate before conjugating the functional agent to the reactive group of the acyl donor substrate. In one embodiment, the purifying step comprises size-based methods, such as chromatography or diafiltration. In another embodiment, the purifying step includes charge-based separation, such as anion exchange or cation exchange chromatography. In another embodiment, the purifying step comprises an affinity-based step, such as Protein A or Protein G chromatography.

BRIEF DESCRIPTION OF THE DRAWINGS

The summary, as well as the following detailed description, is further understood when read in conjunction with the appended drawings. For the purpose of illustrating the disclosed methods, and conjugated immunoglobulins, there are shown in the drawings exemplary embodiments; however, the methods and conjugated immunoglobulins are not limited to the specific embodiments disclosed. In the drawings:

FIG. 2, shows the structures of exemplary Z-Gln-Gly acyl-donor substrates.

FIG. 4, comprising FIGS. 4A, 4B, and 4C, shows solvent exposed lysines in human $IgG_1$ Fab and Fc crystal structures; (A) Fab VH-CH1 and Vκ-Cκ, (B) Fab VH-CH1 and Vλ-Cλ, and (C) Fc CH2 and CH3 were determined using Discovery Studio 4.5 with a 1.4 Å probe radius and highlighted in yellow.

FIG. 5, shows sequences of human IgG₁ (SEQ ID NO: 40), kappa (SEQ ID NO: 41), and lambda (SEQ ID NO: 42) constant domains. Solvent exposed constant domain lysines based on 1FC1 (Fcγ), 4F3F (CH1 and Cκ), and 4HK0(Cλ) are highlighted in red; lysines within loops are underlined. The constant domains are numbered according the EU numbering system.

FIG. 6, comprising

FIG. 7, comprising

FIG. 8, comprising

FIG. 9, comprising

DETAILED DESCRIPTION

Figure 1:
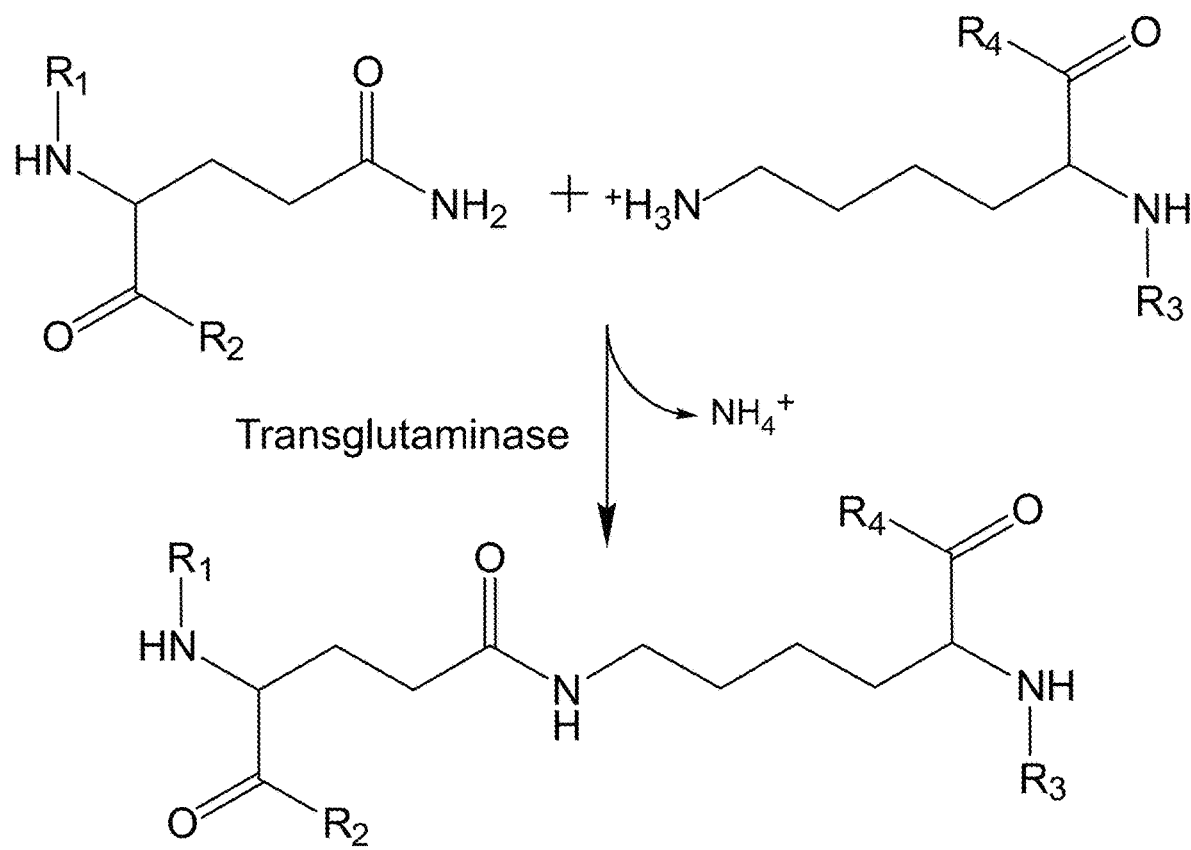
FIG. 1, shows a transglutaminase reaction, wherein the transglutaminase catalyzes the formation of an isopeptide bond between an acyl donor glutamine and an acyl acceptor lysine with release of an ammonia molecule.

The disclosed methods and conjugated immunoglobulins may be understood more readily by reference to the following detailed description taken in connection with the accompanying figures, which form a part of this disclosure. It is to be understood that the disclosed methods and conjugated immunoglobulins are not limited to the specific embodiments described and/or shown herein, and that the terminology used herein is for the purpose of describing particular embodiments by way of example only and is not intended to be limiting of the claimed methods or conjugated immunoglobulins.

Unless specifically stated otherwise, any description as to a possible mechanism or mode of action or reason for improvement is meant to be illustrative only, and the disclosed methods and conjugated immunoglobulins are not to be constrained by the correctness or incorrectness of any such suggested mechanism or mode of action or reason for improvement.

Throughout this text, the descriptions refer to conjugated immunoglobulins and methods of generating the same. Where the disclosure describes or claims a feature or embodiment associated with a conjugated immunoglobulin, such a feature or embodiment is equally applicable to the methods of generating the same. Likewise, where the disclosure describes or claims a feature or embodiment associated with a method of generating a conjugated immunoglobulin, such a feature or embodiment is equally applicable to the conjugated immunoglobulin.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

When values are expressed as approximations, by use of the antecedent "about," it will be understood that the particular value forms another embodiment.

It is to be appreciated that certain features of the disclosed methods and conjugated immunoglobulins which are, for clarity, described herein in the context of separate embodiments, may also be provided in combination in a single embodiment. Conversely, various features of the disclosed methods and conjugated immunoglobulins that are, for brevity, described in the context of a single embodiment, may also be provided separately or in any subcombination.

As used herein, the singular forms "a," "an," and "the" include the plural.

Various terms relating to aspects of the description are used throughout the specification and claims. Such terms are to be given their ordinary meaning in the art unless otherwise indicated. Other specifically defined terms are to be construed in a manner consistent with the definitions provided herein.

The term "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

"Acidic Amino Acid" refers to an amino acid exhibiting a negative charge at physiological pH. Genetically encoded hydrophobic amino acids include aspartate, glutamate, asparagine, and glutamine.

The term "acyl donor substrate" refers to a group with a terminal acyl group on it. Preferably, the "acyl donor substrate" comprises a glutamine residue. An acyl donor substrate may optionally contain a further reactive group. In a first embodiment, the acyl donor substrate is covalently connected to a functional agent. In a second embodiment, the acyl donor substrate is not connected to a functional agent. In one embodiment, the acyl donor substrate comprises a glutamine residue and a reactive group. In another embodiment, the acyl donor substrate comprises one or more linkers, as described further herein. In any of the above embodiments, there is optionally a linker between the acyl donor substrate and the functional agent or between the acyl donor substrate and the reactive group.

The term "antibody", as used herein, broadly refers to any immunoglobulin (Ig) molecule comprised of four polypeptide chains, two heavy (H) chains and two light (L) chains. The term "antibody", as used herein, also refers to any antigen-binding portion, mutant, variant, or derivative of an immunoglobulin molecule, which retains the essential epitope binding features of an Ig molecule. Such mutant, variant, or derivative antibody formats are known in the art and nonlimiting embodiments of which are discussed herein. In one embodiment, the antibody is a humanized antibody. In another embodiment, the antibody is a human antibody. In another embodiment, the antibody is a chimeric antibody. In another embodiment, the antibody is a non-human antibody.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

The term "antigen-binding portion" of an antibody (or simply "antibody portion"), as used herein, refers to one or more fragments of an antibody that retain the ability to specifically bind to an antigen. It has been shown that the antigen-binding function of an antibody can be performed by fragments of a full-length antibody. Such antibody embodiments may also be bispecific, dual specific, or multispecific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding portions are known in the art (Kontermann and Dubel eds., Antibody Engineering (2001) Springer-Verlag. New York. 790 pp. (ISBN 3-540-41354-5).

"Basic Amino Acid" refers to an amino acid exhibiting a positive charge at physiological pH. Genetically encoded hydrophobic amino acids include histidine, lysine and arginine.

As used herein, the term "biological sample" refers to a sample obtained from a subject, including sample of biological tissue or fluid origin obtained in vivo or in vitro. Such samples can be, but are not limited to, body fluid (e.g., blood, blood plasma, serum, milk, spinal fluid, ascites, or urine), organs, tissues, fractions, and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

The term "C-terminal lysine" refers to the C-terminal end of the heavy chain of an immunoglobulin. Preferably, there is at least one amino acid residue after a C-terminal lysine. In one embodiment, wherein there is only one amino acid residue after the C-terminal lysine (amino acid position +1), the amino acid residue directly adjacent to the C-terminal lysine is selected from the group consisting of glycine, alanine, valine, leucine, isoleucine, methionine, phenylalanine, tyrosine, tryptophan, serine, threonine, cysteine, asparagine, glutamine and histidine. In the case where more than one amino acid residue is added to the C-terminal lysine (amino acid position +1, +2, etc.), the amino acid residue directly adjacent to the C-terminal lysine (amino acid position +1) may be selected from any amino acid except aspartic acid, glutamic acid, or proline. In one embodiment, where two amino acid residues are added to the C-terminal lysine, the amino acid residue directly adjacent to the C-terminal lysine (amino acid position +1) is any amino acid except aspartic acid, glutamic acid, or proline, and the second amino acid residue (amino acid position +2) after the C-terminal lysine is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, where two amino acid residues are added to the C-terminal lysine, the first amino acid residue adjacent to the C-terminal lysine (amino acid position +1) is lysine or arginine.

In one embodiment, there is one amino acid residue after the C-terminal lysine (amino acid position +1). In another embodiment, there are two amino acid residues after the C-terminal lysine (amino acid positions +1 and +2). In yet another embodiment, there are three (amino acid positions +1, +2, and +3), four (amino acid positions +1, +2, +3, and +4), five (amino acid positions +1, +2, +3, +4 and +5), six (amino acid positions +1, +2, +3, +4, +5, and +6), seven (amino acid positions +1, +2, +3, +4, +5, +6, and +7), eight (amino acid positions +1, +2, +3, +4, +5, +6, +7, and +8), nine (amino acid positions +1, +2, +3, +4, +5, +6, +7, +8, and +9), ten (amino acid positions +1, +2, +3, +4, +5, +6, +7, +8, +9, and +10), eleven (amino acid positions +1, +2, +3, +4, +5, +6, +7, +8, +9, +10, and +11), twelve (amino acid positions +1, +2, +3, +4, +5, +6, +7, +8, +9, +10, +11, and +12), thirteen (amino acid positions +1, +2, +3, +4, +5, +6, +7, +8, +9, +10, +11, +12, and +13), fourteen (amino acid positions +1, +2, +3, +4, +5, +6, +7, +8, +9, +10, +11, +12, +13, and +14), fifteen (amino acid positions +1, +2, +3, +4, +5, +6, +7, +8, +9, +10, +11, +12, +13, +14, and +15), sixteen (amino acid positions +1, +2, +3, +4, +5, +6, +7, +8, +9, +10, +11, +12, +13, +14, +15, and +16), seventeen (amino acid positions +1, +2, +3, +4, +5, +6, +7, +8, +9, +10, +11, +12, +13, +14, +15, +16, and +17), eighteen (amino acid positions +1, +2, +3, +4, +5, +6, +7, +8, +9, +10, +11, +12, +13, +14, +15, +16, +17, and +18), nineteen (amino acid positions +1, +2, +3, +4, +5, +6, +7, +8, +9, +10, +11, +12, +13, +14, +15, +16, +17, +18, and +19), or twenty (amino acid positions +1, +2, +3, +4, +5, +6, +7, +8, +9, +10, +11, +12, +13, +14, +15, +16, +17, +18, +19, and +20) amino acid residues after the C-terminal lysine.

In one embodiment, the amino acid residues after the C-terminal lysine do not include GTYFQAYGT (SEQ ID NO: 1). In one embodiment, the amino acid residues after the C-terminal lysine do not include GECTYFQAYGCTE (SEQ ID NO: 2). In one embodiment, the amino acid residues after the C-terminal lysine do not include GENTYFQAYGNTE (SEQ ID NO: 3).

In one embodiment, the C-terminal lysine is Lysine 447 of $IgG_1$, $IgG_2$, $IgG_3$, or $IgG_4$. In another embodiment, the C-terminal lysine is the C-terminal lysine of IgD or IgE. In another embodiment, the term "C-terminal lysine" refers to the last lysine residue before the tail piece of $IgA_1$, $IgA_2$, or IgM. In one embodiment, the tail piece of $IgA_1$, $IgA_2$, or IgM is removed. In one embodiment, the tail piece of $IgA_1$, $IgA_2$, or IgM is not removed. The sequences of tail pieces for the antibodies are set forth, below:

```
                                    (SEQ ID NO: 4)
    IgA1           PTHVNVSVVMAEVDGTCY (SEQ ID NO: 4)
    IgA2           PTHVNVSVVMAEVDGTCY (SEQ ID NO: 5)
    IgM            PTLYNVSLVMSDTAGTCY
```

In another embodiment, one or more amino acid residues can be removed, e.g., deleted from the C-terminus of the heavy chain of an immunoglobulin, and a C-terminal lysine residue, followed by at least one additional amino acid residue can be added to the immunoglobulin. For example, amino acid residues 446 and 447 of an $IgG_1$, $IgG_2$, $IgG_3$, or $IgG_4$ immunoglobulin can be deleted, and a C-terminal lysine followed by at least one additional amino acid residue can be added, wherein a microbial transglutaminase can then conjugate the C-terminal lysine of the immunoglobulin to a glutamine residue of an acyl donor substrate. In other words, the C-terminal lysine may be present, for example, at amino acid position 446 of an immunoglobulin if the immunoglobulin has been mutated to remove wild-type amino acid positions 446 and 447. One or more additional amino acid residues may then be added to the C-terminal lysine at, for example, amino acid positions +1, +2, +3, +4, etc., as described herein. In one embodiment, one, two, three, four, five, six, seven, eight, nine, or ten amino acid residues can be removed, e.g., deleted from the C-terminus of the heavy chain of an immunoglobulin, and a C-terminal lysine residue, followed by at least one additional amino acid residue can be added to the immunoglobulin at, for example, amino acid positions +1, +2, +3, +4, etc., as described herein.

In another embodiment, the CH3 domain is removed from the C-terminus of the heavy chain of an immunoglobulin, and a C-terminal lysine residue, followed by at least one additional amino acid residue can be added to the immunoglobulin. In another embodiment, both the CH2 domain and the CH3 domain are removed from the C-terminus of the heavy chain of an immunoglobulin, and a C-terminal lysine residue, followed by at least one additional amino acid residue can be added to the immunoglobulin. In another embodiment, the hinge region, the CH2 domain, and the CH3 domain are removed from the C-terminus of the heavy chain of an immunoglobulin, and a C-terminal lysine residue, followed by at least one additional amino acid residue can be added to the immunoglobulin. In yet another embodiment, the CH1 domain, the hinge region, the CH2 domain, and the CH3 domain are removed from the C-terminus of the heavy chain of an immunoglobulin, and a C-terminal lysine residue, followed by at least one additional amino acid residue can be added to the immunoglobulin.

The term "click chemistry" refers to particular reactions for protein synthesis and/or conjugation which are high yield, highly-selective, reliable and clean. See, e.g., King et al., "Developments in the Field of Bioorthagonal Bond Forming Reactions—Past and Present Trends", Bioconjug. Chem., (2014) 25(5): 825-839; McKay et al., "Click Chemistry in Complex Mixtures: Bioorthagonal Bioconjugation", Chem. Biol., (2014) 21(9): 1075-1101.

The term "chimerized," "chimeric," "chimeric antibody" and like terms refer to an immunoglobulin comprising a heavy chain variable region and light chain variable region, i.e., antigen-binding region, from one source or species and at least a portion of a heavy chain constant region and light chain constant region derived from a different source or species. These portions may be joined together chemically by conventional techniques (e.g., synthetic) or prepared as a contiguous polypeptide using genetic engineering techniques (e.g., DNA encoding the protein portions of the chimeric antibody may be expressed to produce a contiguous polypeptide chain). Other forms of "chimeric immunoglobulins" encompassed by the present disclosure are those in which the class or subclass has been modified or changed from that of the original immunoglobulin (also referred to as "class-switched immunoglobulins"). Throughout the disclosure, chimeric immunoglobulins are designated "xi." Herein, "chimeric immunoglobulin" and like terms refer to the sequence of the immunoglobulin rather than the process used to generate the antibody.

As used herein, "Lys447" or "Lysine 447" refers to a lysine residue at amino acid position 447 of the heavy chain constant region of an immunoglobulin (as numbered using the EU numbering system), and which is, for example, the C-terminal codon in $IgG_1$, $IgG_2$, $IgG_3$, $IgG_4$, IgD, and IgE.

As used herein, "functional agent" refers to an agent having therapeutic, diagnostic, or other functional property (ies). In one embodiment, a functional agent may be a therapeutic agent. In another embodiment, a functional agent may be a diagnostic agent. Functional agents may be large molecules or small molecules. Large molecule functional agents include, but are not limited to, an antibody and antigen-binding portions thereof. Small molecule functional agents include, but are not limited to, chemotherapeutic agents, cytotoxic agents, antibiotics, other organic compounds which may regulate biological process (e.g., drugs), and polypeptides.

The term "humanized," "humanized immunoglobulin" and like terms refer to immunoglobulins in which the framework or "complementarity determining regions" (CDR) have been modified to comprise the CDR of an immunoglobulin of different specificity as compared to that of the parent immunoglobulin. For the most part, humanized immunoglobulins are human immunoglobulins (recipient immunoglobulin) in which residues from a hypervariable region of the recipient are replaced by residues from a hypervariable region of a non-human species (donor immunoglobulin) such as mouse, rat, rabbit or nonhuman primate having the desired specificity, affinity, and capacity. In some instances, FWR residues of the human immunoglobulin are replaced by corresponding non-human residues. Furthermore, humanized immunoglobulins may comprise residues that are not found in the recipient immunoglobulin or in the donor immunoglobulin. These modifications are made to further refine immunoglobulin performance. In general, the humanized immunoglobulin will comprise substantially all of at least one, and typically two, variable domains, in which all or substantially all of the hypervariable loops correspond to those of a non-human immunoglobulin and all or substantially all of the FWRs are those of a human immunoglobulin sequence. The humanized immunoglobulin can optionally also comprise at least a portion of an immunoglobulin constant region (Fc), typically that of a human immunoglobulin. See, e.g., Riechmann, L., et al., Nature 332 (1988) 323-327; and Neuberger, M. S., et al., Nature 314 (1985) 268-270. Throughout the disclosure, "humanized immunoglobulins" are designated "zu." Herein, "humanized immunoglobulin" and like terms refer to the sequence of the immunoglobulin rather than the process used to generate the immunoglobulin.

The term "diagnostic agent" refers to a compound which may be useful for in vivo imaging studies such as CT, MRI and X-ray and/or in vitro imaging studies. Non-limiting examples of diagnostic agents include a fluorophore, a fluorescent dye, a radionuclide, and an enzyme.

The term "donor immunoglobulin" refers to a non-human immunoglobulin that contributes the amino acid sequences of its variable regions, CDRs, or other functional fragments or analogs thereof to the humanized immunoglobulin, and thereby provides the humanized immunoglobulin with the antigenic specificity and neutralizing activity characteristic of the donor immunoglobulin.

The term "recipient immunoglobulin" refers to an immunoglobulin heterologous to the donor immunoglobulin, which provides the amino acid sequences of its heavy and/or light chain framework regions and/or its heavy and/or light chain constant regions to the humanized immunoglobulin. The recipient immunoglobulin may be derived from any mammal. In preferred embodiments, the recipient immunoglobulin is non-immunogenic in humans. Preferably the recipient immunoglobulin is a human immunoglobulin.

"Humanizing" refers to a process of generating a humanized immunoglobulin and includes any process for generating humanized immunoglobulins having the above characteristics, including, but not limited to, in silico humanization, engineering species/host CDRs into human immunoglobulins, substituting framework region residues of a chimeric immunoglobulin to match a corresponding human framework region, etc.

"Immunoglobulin," as used herein, refers to a protein consisting of one or more polypeptides substantially encoded by immunoglobulin genes including the kappa and lambda light chains and the alpha, gamma, delta, epsilon and mu heavy chains. Full-length immunoglobulin "light chains" (about 25 Kd or 214 amino acids) are encoded by a variable region gene at the $NH_2$-terminus (about 110 amino acids) and a kappa or lambda constant region gene at the COOH—terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids). "Immunoglobulins" include: (a) immunoglobulin polypeptides, i.e., polypeptides of the immunoglobulin family that contain an antigen binding site that specifically binds to a specific antigen, including all immunoglobulin isotypes (IgG, IgA, IgE, IgM, IgD, and IgY), classes (e.g., $IgG_1$, $IgG_2$, $IgG_3$, $IgG_4$, $IgA_1$, $IgA_2$), subclasses, and various monomeric and polymeric forms of each isotype, unless otherwise specified; and (b) conservatively substituted variants of such immunoglobulin polypeptides that immunospecifically bind to the antigen. Immunoglobulins are generally described in, for example, Harlow & Lane, Antibodies: A Laboratory Manual (Cold Spring Harbor Laboratory Press, 1988).

One form of immunoglobulin disclosed herein constitutes the basic structural unit of an antibody. For example, an antibody can include a tetramer and consist of two identical pairs of immunoglobulin chains, each pair having one light chain and one heavy chain. Generally, in each pair, the light chain and heavy chain variable regions are together responsible for binding to an antigen, and the constant regions are responsible for the antibody effector functions.

In addition to antibodies, immunoglobulins may exist in a variety of other forms including, for example: antigen-binding fragments or portions of a full-length immunoglobulin, such as Fv, Fab, (Fab')$_2$ and Fv fragments; and alternative antibody formats such as single chain immunoglobulins (scFV and scFab), diabodies, triabodies, tetrabodies, linear antibodies, and multispecific antibodies, to name a few. See, for example, James D. Marks, Antibody Engineering, Chapter 2, Oxford University Press (1995) (Carl K. Borrebaeck, Ed.).

In one embodiment, an immunoglobulin may comprise an Fab fragment. In another embodiment, an immunoglobulin may comprise a CH3 domain. In another embodiment, an immunoglobulin may comprise a heavy chain.

As used herein, the term "immunospecifically" refers to the ability of an immunoglobulin to specifically bind to an antigen against which the immunoglobulin was generated and not specifically bind to other peptides or proteins. An immunoglobulin that immunospecifically binds to an antigen against which the immunoglobulin was generated may not bind to other polypeptides or proteins, or may bind to other polypeptides or proteins with a lower binding affinity than the antigen against which the immunoglobulin was generated as determined by, for example, immunoassays, BIAcore, or other assays known in the art. An immunoglobulin binds immunospecifically to an antigen against which the immunoglobulin was generated when it binds to the antigen with a higher binding affinity than to any cross-reactive antigen as determined using experimental techniques, such as, but not limited to, radioimmunoassays (RIA) and enzyme-linked immunosorbent assays (ELISAs) (See, for example, Paul, ed., Fundamental Immunology, 2nd ed., Raven Press, New York, pages 332-336 (1989) for a discussion regarding antibody specificity.).

"Linker," as used herein, refers to a spacer, which may be a straight or branched chain, for connecting an immunoglobulin (through an acyl donor substrate) to a functional agent or a reactive group. Such linkers may be cleavable (e.g., acid labile or protease cleavable) or non-cleavable. In one embodiment, a linker is a polyethylene glycol (PEG) moiety. In another embodiment, a linker comprises one or more amino acids and a polyethylene glycol moiety (PEG).

The term "monoclonal antibody" refers to an antibody that is derived from a single cell clone, including any eukaryotic or prokaryotic cell clone, or a phage clone, and not the method by which it is produced. A monoclonal antibody displays a single binding specificity and affinity for a particular epitope. The term "monoclonal antibody" is not limited to antibodies produced through hybridoma technology.

"Native" refers to the wild type immunoglobulin sequence from the species in which the immunoglobulin is derived.

As used herein, "percent identity" and like terms is used to describe the sequence relationships between two or more nucleic acids, polynucleotides, proteins, or polypeptides, and is understood in the context of and in conjunction with the terms including: (a) reference sequence, (b) comparison window, (c) sequence identity and (d) percentage of sequence identity.
- (a) A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, exemplary lengths of the reference polypeptide sequence include at least about 16 amino acids, at least about 20 amino acids, at least about 25 amino acids, at least about 35 amino acids, at least about 50 amino acids, or at least about 100 amino acids. For nucleic acids, exemplary length of the reference nucleic acid sequence include at least about 50 nucleotides, at least about 60 nucleotides, at least about 75 nucleotides, at least about 100 nucleotides, or at least about 300 nucleotides, or any integer thereabout or therebetween.
- (b) A "comparison window" includes reference to a contiguous and specified segment of a polynucleotide or polypeptide sequence, wherein the polynucleotide or polypeptide sequence may be compared to a reference sequence and wherein the portion of the polynucleotide or polypeptide sequence in the comparison window may comprise additions, substitutions, or deletions (i.e., gaps) compared to the reference sequence (which does not comprise additions, substitutions, or deletions) for optimal alignment of the two sequences. Exemplary comparison windows can be at least 20 contiguous nucleotides or amino acids in length, and optionally may be 30, 40, 50, 100, or longer. Those of skill in the art understand that to avoid a misleadingly high similarity to a reference sequence due to inclusion of gaps in the polynucleotide or polypeptide sequence a gap penalty is typically introduced and is subtracted from the number of matches.
- (c) Methods of alignment of sequences for comparison are well known in the art. Optimal alignment of sequences for comparison may be conducted by the local homology algorithm of Smith and Waterman, Adv. Appl. Math., 2: 482, 1981; by the homology alignment algorithm of Needleman and Wunsch, J. Mol. Biol., 48: 443, 1970; by the search for similarity method of Pearson and Lipman, Proc. Natl. Acad. Sci. USA, 8: 2444, 1988; by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 7 Science Dr., Madison, Wis., USA; the CLUSTAL program is well described by Higgins and Sharp, Gene, 73: 237-244, 1988; Corpet, et al., Nucleic Acids Research, 16:881-90, 1988; Huang, et al., Computer Applications in the Biosciences, 8:1-6, 1992; and Pearson, et al., Methods in Molecular Biology, 24:7-331, 1994. The BLAST family of programs which may be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York, 1995. New versions of the above programs or new programs altogether will undoubtedly become available in the future, and may be used with the present disclosure.
- (d) "Percent identity" means the value determined by comparing two optimally aligned sequences over a comparison window, wherein the portion of the polynucleotide or polypeptide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Pharmaceutically effective amount" refers to an amount of an immunoglobulin that treats a subject.

"Pharmaceutically acceptable carrier" refers to components of a pharmaceutical formulation for an immunoglobulin as described herein for administration to a subject. For example, a pharmaceutically acceptable carrier may be a liposome-based, lipid-based and/or nano-particle-based.

The term "reactive group" as used here in refers to a chemical functional group which may react to other compounds, such as functional agents, to form at least one covalent bond. In one embodiment, reactive groups are reactive in click chemistry coupling reactions. Non-limiting examples of reactive groups include (1R,8S,9s)-bicyclo [6.1.0]non-4-yn-9-ylmethanol (BCN),

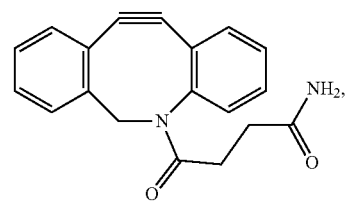

(DBCO)

trans-cyclooctene (TCO), azido ($N_3$), alkyne, tetrazine methylcyclopropene, norbornene, hydrazide/hydrazine, and aldehyde.

The term "subject" as used herein refers to a human or non-human organism. Thus, the methods, immunoglobulins, and conjugated immunoglobulins described herein are applicable to both human and veterinary diseases and conditions. Subjects can be "patients," i.e., living humans or non-human organisms that are receiving medical care for a disease or condition, or humans or non-human organisms with no defined illness who are being investigated for signs of pathology or presence/absence of a particular condition.

"Substituting" refers to the replacement of one amino acid residue for another. "Substituting" includes, for example, missense mutations in one or more DNA base pairs encoding the amino acid residue or engineering the protein to exchange one amino acid with another.

As used herein, "treating" and like terms refer to reducing the severity and/or frequency of disease symptoms, eliminating disease symptoms and/or the underlying cause of said symptoms, reducing the frequency or likelihood of disease symptoms and/or their underlying cause, and improving or remediating damage caused, directly or indirectly, by disease.

The term "therapeutic agent" means a large or small molecule which may be administered to a subject in need thereof to treat a condition. Therapeutic agents may be administered to treat, or prevent the onset, slow the progression, or to ameliorate one or more symptoms of a medical condition in subjects suffering from the same. Therapeutic agents include, but are not limited to, an antibody or antigen-binding portion thereof, a chemotherapeutic agent, a radioactive agent, a cytotoxic agent, an antibiotic, etc. In one embodiment, the therapeutic agent is a small molecule. In another embodiment, the therapeutic agent is a polypeptide.

As used herein "90% identical to" encompasses at least 90% identical, 91% identical, 92% identical, 93% identical, 94% identical, 95% identical, 96% identical, 97% identical, 98% identical, 99% identical, or 100% identical to the reference item (e.g., a biological sequence).

The following abbreviations are used throughout the disclosure: antibody drug conjugates (ADCs); drug-to-antibody ratio (DAR); frame work region (FWR); complementary determining region (CDR); auristatin F (AuF); variable heavy region (VH); variable light region (VL); variable kappa (Vκ); gamma constant region (Cγ); kappa constant region (Cκ); monoclonal antibody (mAb); lysine at amino acid position 447 of the heavy chain of the immunoglobulin, as numbered using the EU numbering system (Lys447).

Generation of Conjugated Immunoglobulins

Disclosed herein are methods for generating a conjugated immunoglobulin, the methods comprising: incubating an immunoglobulin with a microbial transglutaminase and a functional agent comprising an acyl donor substrate, a) wherein the immunoglobulin comprises at least one amino acid residue after a C-terminal lysine, b) wherein the acyl donor substrate comprises a glutamine residue, and c) wherein the functional agent is a therapeutic agent or a diagnostic agent, wherein the microbial transglutaminase conjugates the C-terminal lysine of the immunoglobulin to the glutamine residue of the acyl donor substrate on the functional agent, thereby generating the conjugated immunoglobulin.

Also disclosed herein are methods for generating a conjugated immunoglobulin, the methods comprising: i) incubating an immunoglobulin with a microbial transglutaminase and an acyl donor substrate, a) wherein the immunoglobulin comprises at least one amino acid residue after a C-terminal lysine, b) wherein the acyl donor substrate comprises a glutamine residue and a reactive group, wherein the microbial transglutaminase conjugates the C-terminal lysine of the immunoglobulin to the glutamine residue of the acyl donor substrate, and ii) conjugating a functional agent to the reactive group of the acyl donor substrate, wherein the functional agent is a therapeutic agent or a diagnostic agent, thereby generating the conjugated immunoglobulin.

Conjugation can be performed by dissolving a functional agent comprising an acyl donor substrate in a dissolution solution and incubating the dissolved functional agent with the immunoglobulin and microbial transglutaminase in a conjugation buffer. Conjugation may also be performed by dissolving a acyl donor substrate in a dissolution solution and incubating the acyl donor substrate with the immunoglobulin and microbial transglutaminase in a conjugation buffer.

For aqueous-insoluble functional agents and acyl donor substrates, suitable dissolution solutions include organic, water-miscible solvents such as dimethylsulfoxide (DMSO). For aqueous-soluble functional agents and acyl donor substrates, suitable dissolution solutions include, but are not limited to, water or buffered aqueous solutions, such as phosphate-buffered saline, pH 7.2 (1×PBS) or DPBS.

Suitable concentrations of the functional agent or the acyl donor substrate include from about 10 μM to about 800 mM, from about 10 mM to about 100 mM, from about 25 mM to about 100 mM, from about 40 mM to about 100 mM, from about 55 mM to about 100 mM, from about 70 mM to about 100 mM, from about 10 mM to about 90 mM, from about 10 mM to about 75 mM, from about 10 mM to about 60 mM, from about 10 mM to about 50 mM, from about 10 mM to about 40 mM, or from about 10 mM to about 30 mM.

In some embodiments, the concentration of the functional agent or the acyl donor substrate can be about 10 μM. In some embodiments, the concentration of the functional agent or the acyl donor substrate can be about 25 μM. In some embodiments, the concentration of the functional agent or the acyl donor substrate can be about 50 μM. In some embodiments, the concentration of the functional agent or the acyl donor substrate can be about 100 μM. In some embodiments, the concentration of the functional agent or the acyl donor substrate can be about 250 μM. In some embodiments, the concentration of the functional agent or the acyl donor substrate can be about 500 μM. In some embodiments, the concentration of the functional agent or the acyl donor substrate can be about 750 μM. In some embodiments, the concentration of the functional agent or the acyl donor substrate can be about 1 mM. In some embodiments, the concentration of the functional agent or the acyl donor substrate can be about 10 mM. In some embodiments, the concentration of the functional agent or the acyl donor substrate can be about 20 mM. In some embodiments, the concentration of the functional agent or the acyl donor substrate can be about 30 mM. In some embodiments, the concentration of the functional agent or the acyl donor substrate can be about 40 mM. In some embodiments, the concentration of the functional agent or the acyl donor substrate can be about 50 mM. In some embodiments, the concentration of the functional agent or the acyl donor substrate can be about 60 mM. In some embodiments, the concentration of the functional agent or the acyl donor substrate can be about 70 mM. In some embodiments, the concentration of the functional agent or the acyl donor substrate can be about 80 mM. In some embodiments, the concentration of the functional agent or the acyl donor substrate can be about 90 mM. In some embodiments, the concentration of the functional agent or the acyl donor substrate can be about 100 mM. In some embodiments, the concentration of the functional agent or the acyl donor substrate can be about 150 mM. In some embodiments, the concentration of the functional agent or the acyl donor substrate can be about 200 mM. In some embodiments, the concentration of the functional agent or the acyl donor substrate can be about 250 mM. In some embodiments, the concentration of the functional agent or the acyl donor substrate can be about 300 mM. In some embodiments, the concentration of the functional agent or the acyl donor substrate can be about 350 mM. In some embodiments, the concentration of the functional agent or the acyl donor substrate can be about 400 mM. In some embodiments, the concentration of the functional agent or the acyl donor substrate can be about 450 mM. In some embodiments, the concentration of the functional agent or the acyl donor substrate can be about 500 mM. In some embodiments, the concentration of the functional agent or the acyl donor substrate can be about 550 mM. In some embodiments, the concentration of the functional agent or the acyl donor substrate can be about 600 mM. In some embodiments, the concentration of the functional agent or the acyl donor substrate can be about 650 mM. In some embodiments, the concentration of the functional agent or the acyl donor substrate can be about 700 mM. In some embodiments, the concentration of the functional agent or the acyl donor substrate can be about 750 mM. In some embodiments, the concentration of the functional agent or the acyl donor substrate can be about 800 mM.

Suitable concentrations of immunoglobulin include from about 0.1 mg/ml to about 20 mg/ml, from about 0.5 mg/ml to about 20 mg/ml, from about 1 mg/ml to about 20 mg/ml, from about 5 mg/ml to about 20 mg/ml, from about 10 mg/ml to about 20 mg/ml, from about 0.1 mg/ml to about 15 mg/ml, from about 0.1 mg/ml to about 12 mg/ml, from about 0.1 mg/ml to about 10 mg/ml, from about 0.1 mg/ml to about 5 mg/ml, or from about 0.1 mg/ml to about 2 mg/ml. In some embodiments, the concentration of immunoglobulin can be about 0.1 mg/ml. In some embodiments, the concentration of immunoglobulin can be about 0.5 mg/ml. In some embodiments, the concentration of immunoglobulin can be about 1 mg/ml. In some embodiments, the concentration of immunoglobulin can be about 2 mg/ml. In some embodiments, the concentration of immunoglobulin can be about 5 mg/ml. In some embodiments, the concentration of immunoglobulin can be about 10 mg/ml. In some embodiments, the concentration of immunoglobulin can be about 15 mg/ml. In some embodiments, the concentration of immunoglobulin can be about 20 mg/ml.

Suitable ratios of a functional agent or an acyl donor substrate:immunoglobulin include from about 1:1 to 100:1. In one embodiment, the ratio of functional agent to acyl donor substrate:immunoglobulin is about 25:1 to about 75:1. In another embodiment, the ratio of functional agent to acyl donor substrate:immunoglobulin is about 40:1 to about 60:1. In some embodiments, the ratio of a functional agent or an acyl donor substrate:immunoglobulin can be 1:1. In some embodiments, the ratio of a functional agent or an acyl donor substrate:immunoglobulin can be 2:1. In some embodiments, the ratio of a functional agent or an acyl donor substrate:immunoglobulin can be 3:1. In some embodiments, the ratio of a functional agent or an acyl donor substrate:immunoglobulin can be 4:1. In some embodiments, the ratio of a functional agent or an acyl donor substrate:immunoglobulin can be 5:1. In some embodiments, the ratio of a functional agent or an acyl donor substrate:immunoglobulin can be 6:1. In some embodiments, the ratio of a functional agent or an acyl donor substrate:immunoglobulin can be 7:1. In some embodiments, the ratio of a functional agent or an acyl donor substrate:immunoglobulin can be 8:1. In some embodiments, the ratio of a functional agent or an acyl donor substrate:immunoglobulin can be 9:1. In some embodiments, the ratio of a functional agent or an acyl donor substrate:immunoglobulin can be 10:1. In some embodiments, the ratio of a functional agent or an acyl donor substrate:immunoglobulin can be 11:1. In some embodiments, the ratio of a functional agent or an acyl donor substrate:immunoglobulin can be 12:1. In some embodiments, the ratio of a functional agent or an acyl donor substrate:immunoglobulin can be 13:1. In some embodiments, the ratio of a functional agent or an acyl donor substrate:immunoglobulin can be 14:1. In some embodiments, the ratio of a functional agent or an acyl donor substrate:immunoglobulin can be 15:1. In some embodiments, the ratio of a functional agent or an acyl donor substrate:immunoglobulin can be 16:1. In some embodiments, the ratio of a functional agent or an acyl donor substrate:immunoglobulin can be 17:1. In some embodiments, the ratio of a functional agent or an acyl donor substrate:immunoglobulin can be 18:1. In some embodiments, the ratio of a functional agent or an acyl donor substrate:immunoglobulin can be 19:1. In some embodiments, the ratio of a functional agent or an acyl donor substrate:immunoglobulin can be 20:1. In some embodiments, the ratio of a functional agent or an acyl donor substrate:immunoglobulin can be 25:1. In some embodiments, the ratio of a functional agent or an acyl donor substrate:immunoglobulin can be 30:1. In some embodiments, the ratio of a functional agent or an acyl donor substrate:immunoglobulin can be 35:1. In some embodiments, the ratio of a functional agent or an acyl donor substrate:immunoglobulin can be 40:1. In some embodiments, the ratio of a functional agent or an acyl donor substrate:immunoglobulin can be 45:1. In some embodiments, the ratio of a functional agent or an acyl donor substrate:immunoglobulin can be 50:1. In some embodiments, the ratio of a functional agent or an acyl donor substrate:immunoglobulin can be 60:1. In some embodiments, the ratio of a functional agent or an acyl donor substrate:immunoglobulin can be 70:1. In some embodiments, the ratio of a functional agent or an acyl donor substrate:immunoglobulin can be 80:1. In some embodiments, the ratio of a functional agent or an acyl donor substrate:immunoglobulin can be 90:1. In some embodiments, the ratio of a functional agent or an acyl donor substrate:immunoglobulin can be 100:1.

The incubating can be performed in a number of suitable conjugation buffers including, for example, DPBS, 1×PBS, pH 7.2, sodium phosphate, potassium phosphate, sodium borate, Tris, and HEPES, to name a few. The concentration of conjugation buffer include from about 5 mM to about 2 M, from about 5 mM to about 1 M, from about 5 mM to about 500 mM, from about 5 mM to about 100 mM, from about 10 mM to about 100 mM, from about 20 mM to about 100 mM, from about 30 mM to about 100 mM, from about 45 mM to about 100 mM, from about 60 mM to about 100 mM, from about 75 mM to about 100 mM, from about 10 mM to about 90 mM, from about 10 mM to about 75 mM, from about 10 mM to about 60 mM, from about 10 mM to about 45 mM, or from about 10 mM to about 30 mM. In some embodiments, the concentration of the conjugation buffer can be about 10 mM. In some embodiments, the concentration of the conjugation buffer can be about 20 mM. In some embodiments, the concentration of the conjugation buffer can be about 30 mM. In some embodiments, the concentration of the conjugation buffer can be about 40 mM. In some embodiments, the concentration of the conjugation buffer can be about 50 mM. In some embodiments, the concentration of the conjugation buffer can be about 60 mM. In some embodiments, the concentration of the conjugation buffer can be about 70 mM. In some embodiments, the concentration of the conjugation buffer can be about 80 mM. In some embodiments, the concentration of the conjugation buffer can be about 90 mM. In some embodiments, the concentration of the conjugation buffer can be about 100 mM. In some embodiments, the concentration of the conjugation buffer can be about 250 mM. In some embodiments, the concentration of the conjugation buffer can be about 500 mM. In some embodiments, the concentration of the conjugation buffer can be about 750 mM. In some embodiments, the concentration of the conjugation buffer can be about 1 M. In some embodiments, the concentration of the conjugation buffer can be about 1.25 M. In some embodiments, the concentration of the conjugation buffer can be about 1.5 M. In some embodiments, the concentration of the conjugation buffer can be about 1.75 M. In some embodiments, the concentration of the conjugation buffer can be about 2 M.

The conjugation buffer can further include sodium chloride. Suitable concentrations of sodium chloride include from about 0 mM to about 2 M, from about 0 mM to about 1 M, from about 1 M to about 2 M, from about 500 mM to about 1.5 M, from about 25 mM to about 500 mM, from about 50 mM to about 500 mM, from about 75 mM to about 500 mM, from about 100 mM to about 500 mM, from about 150 mM to about 500 mM, from about 200 mM to about 500 mM, from about 250 mM to about 500 mM, from about 300 mM to about 500 mM, from about 350 mM to about 500 mM, from about 400 mM to about 500 mM, from about 0 mM to about 400 mM, from about 0 mM to about 350 mM, from about 0 mM to about 300 mM, from about 0 mM to about 250 mM, from about 0 mM to about 200 mM, from about 0 mM to about 150 mM, from about 0 mM to about 100 mM, from about 0 mM to about 50 mM, or from about 0 mM to about 25 mM. In some embodiments, the concentration of sodium chloride can be about 25 mM. In some embodiments, the concentration of sodium chloride can be about 50 mM. In some embodiments, the concentration of sodium chloride can be about 75 mM. In some embodiments, the concentration of sodium chloride can be about 100 mM. In some embodiments, the concentration of sodium chloride can be about 150 mM. In some embodiments, the concentration of sodium chloride can be about 200 mM. In some embodiments, the concentration of sodium chloride can be about 250 mM. In some embodiments, the concentration of sodium chloride can be about 300 mM. In some embodiments, the concentration of sodium chloride can be about 350 mM. In some embodiments, the concentration of sodium chloride can be about 400 mM. In some embodiments, the concentration of sodium chloride can be about 500 mM. In some embodiments, the concentration of sodium chloride can be about 750 mM. In some embodiments, the concentration of sodium chloride can be about 1 M. In some embodiments, the concentration of sodium chloride can be about 1.25 M. In some embodiments, the concentration of sodium chloride can be about 1.5 M. In some embodiments, the concentration of sodium chloride can be about 1.75 M. In some embodiments, the concentration of sodium chloride can be about 2 M.

The pH of the conjugation buffer can be from about 4 to about 9. In some embodiments, the pH of the conjugation buffer can be about 5 to about 8. In another embodiment, the pH of the conjugation buffer can be about 6 to about 7. In some embodiments, the pH of the conjugation buffer can be about 4. In some embodiments, the pH of the conjugation buffer can be about 4.5. In some embodiments, the pH of the conjugation buffer can be about 5. In some embodiments, the pH of the conjugation buffer can be about 5.5. In some embodiments, the pH of the conjugation buffer can be about 6.0. In some embodiments, the pH of the conjugation buffer can be about 6.5. In some embodiments, the pH of the conjugation buffer can be about 6.6. In some embodiments, the pH of the conjugation buffer can be about 6.7. In some embodiments, the pH of the conjugation buffer can be about 6.8. In some embodiments, the pH of the conjugation buffer can be about 6.9. In some embodiments, the pH of the conjugation buffer can be about 7.0. In some embodiments, the pH of the conjugation buffer can be about 7.1. In some embodiments, the pH of the conjugation buffer can be about 7.2. In some embodiments, the pH of the conjugation buffer can be about 7.3. In some embodiments, the pH of the conjugation buffer can be about 7.4. In some embodiments, the pH of the conjugation buffer can be about 7.5. In some embodiments, the pH of the conjugation buffer can be about 7.6. In some embodiments, the pH of the conjugation buffer can be about 7.7. In some embodiments, the pH of the conjugation buffer can be about 7.8. In some embodiments, the pH of the conjugation buffer can be about 7.9. In some embodiments, the pH of the conjugation buffer can be about 8.0. In some embodiments, the pH of the conjugation buffer can be about 8.1. In some embodiments, the pH of the conjugation buffer can be about 8.2. In some embodiments, the pH of the conjugation buffer can be about 8.3. In some embodiments, the pH of the conjugation buffer can be about 8.4. In some embodiments, the pH of the conjugation buffer can be about 8.5. In some embodiments, the pH of the conjugation buffer can be about 9.

To facilitate solubility of a functional agent or an acyl donor substrate in the conjugation buffer, a final concentration of organic, water-miscible solvent in the conjugation buffer may be from about 0% to about 20%, from about 2% to about 20%, from about 5% to about 20%, from about 8% to about 20%, from about 11% to about 20%, from about 16% to about 20%, from about 0% to about 18%, from about 0% to about 15%, from about 0% to about 12%, from about 0% to about 10%, from about 0% to about 8%, from about 0% to about 6%, or from about 0% to about 2%.

The conjugation buffer can further comprise propylene glycol to facilitate solubility of the thiol-reactive compound in the conjugation buffer. Suitable concentrations of propylene glycol include from about 1% to about 50%, from about 20% to about 50%, from about 30% to about 50%, from about 40% to about 50%, from about 10% to about 40%, from about 10% to about 30%, or from about 10% to about 20%. In some embodiments, the concentration of propylene glycol can be about 1% or about 5%. In some embodiments, the concentration of propylene glycol can be about 10%. In some embodiments, the concentration of propylene glycol can be about 20%. In some embodiments, the concentration of propylene glycol can be about 30%. In some embodiments, the concentration of propylene glycol can be about 40%. In some embodiments, the concentration of propylene glycol can be about 50%.

The conjugation buffer can further comprise a non-ionic detergent to facilitate solubility of the conjugated immunoglobulin in the conjugation buffer. Exemplary non-ionic detergents include, but are not limited to, polysorbate-20 or polysorbate-80. Suitable concentrations of non-ionic detergent include from about 0% to about 1%, from about 0.1% to about 1%, from about 0.3% to about 1%, from about 0.5% to about 1%, from about 0.7% to about 1%, from about 0% to about 0.8%, from about 0% to about 0.6%, from about 0% to about 0.4%, or from about 0% to about 0.2%. In some embodiments, the concentration of non-ionic detergent can be about 0.1%. In some embodiments, the concentration of non-ionic detergent can be about 0.2%. In some embodiments, the concentration of non-ionic detergent can be about 0.3%. In some embodiments, the concentration of non-ionic detergent can be about 0.4%. In some embodiments, the concentration of non-ionic detergent can be about 0.5%. In some embodiments, the concentration of non-ionic detergent can be about 0.6%. In some embodiments, the concentration of non-ionic detergent can be about 0.7%. In some embodiments, the concentration of non-ionic detergent can be about 0.8%. In some embodiments, the concentration of non-ionic detergent can be about 0.9%. In some embodiments, the concentration of non-ionic detergent can be about 1.0%.

The incubating can be performed for about 30 minutes to about 48 hours, for about 1 hour to about 48 hours, for about 2 hours to about 24 hours, for about 24 hours to about 48 hours, for about 30 hours to about 48 hours, for about 36 hours to about 48 hours, for about 42 hours to about 48 hours, for about 2 hours to about 42 hours, for about 2 hours to about 36 hours, for about 2 hours to about 30 hours, for about 2 hours to about 24 hours, for about 2 hours to about 18 hours, for about 2 hours to about 12 hours, about 30 minutes to about 1 hour, about 30 minutes to about 2 hours, or for about 2 hours to about 6 hours. In some embodiments, the incubating can be performed for about 30 minutes. In some embodiments, the incubating can be performed for about 1 hour. In some embodiments, the incubating can be performed for about 1.5 hours. In some embodiments, the incubating can be performed for 2 hours. In some embodiments, the incubating can be performed for 6 hours. In some embodiments, the incubating can be performed for 12 hours. In some embodiments, the incubating can be performed for 18 hours. In some embodiments, the incubating can be performed for 24 hours. In some embodiments, the incubating can be performed for 30 hours. In some embodiments, the incubating can be performed for 36 hours. In some embodiments, the incubating can be performed for 42 hours. In some embodiments, the incubating can be performed for 48 hours.

The temperature of the incubating can be from about 4° C. to about 50° C., from about 18° C. to about 37° C., from about 20° C. to about 37° C., from about 22° C. to about 37° C., from about 24° C. to about 37° C., from about 26° C. to about 37° C., from about 28° C. to about 37° C., from about 30° C. to about 37° C., from about 32° C. to about 37° C., from about 34° C. to about 37° C., from about 18° C. to about 34° C., from about 18° C. to about 32° C., from about 18° C. to about 30° C., from about 18° C. to about 28° C., from about 18° C. to about 26° C., or from about 18° C. to about 24° C. In some embodiments, the incubating can be performed at 4° C. In some embodiments, the incubating can be performed at 18° C. In some embodiments, the incubating can be performed at 20° C. In some embodiments, the incubating can be performed at 22° C. In some embodiments, the incubating can be performed at 24° C. In some embodiments, the incubating can be performed at 26° C. In some embodiments, the incubating can be performed at 28° C. In some embodiments, the incubating can be performed at 30° C. In some embodiments, the incubating can be performed at 32° C. In some embodiments, the incubating can be performed at 34° C. In some embodiments, the incubating can be performed at 37° C. In some embodiments, the incubating can be performed at 50° C.

Unincorporated functional agent or acyl donor substrate can be separated from the conjugated immunoglobulin by desalting chromatography using a number of suitable resins including, but not limited to, G-25 resin, G-50 resin, Biogel P10, or other resins with exclusion limits of ranges 5,000-10,000 Da. Chromatography can be performed in column format or spin-column format, depending on scale. Suitable buffers for desalting include, for example, DPBS, 1×PBS, sodium phosphate, potassium phosphate, sodium borate, Tris, or HEPES-based buffers may substitute for 1×PBS.

In a first embodiment, the functional agent comprising an acyl donor substrate which comprises a glutamine residue conjugated to the C-terminal lysine via the acyl donor substrate. In this first embodiment, the functional agent is combined with the acyl donor substrate prior to conjugation with the immunoglobulin by reacting the reactive group on the acyl donor substrate with the functional agent. In a second embodiment, the acyl donor substrate comprising a glutamine residue and a reactive group is first conjugated to the immunoglobulin, and then the reactive group is joined to a functional agent.

The acyl donor substrates can comprise a linker, "L". Linkers can be non-cleavable linkers or cleavable linkers. Exemplary linkers include, for example, disulfide containing linkers, acetal-based linkers, and ketal-based linkers. In some aspects, the linker can be a non-cleavable linker. Suitable non-cleavable linkers include, but are not limited to, one or more amino acid, polyethylene glycol (PEG) or an alkyl. In some embodiments, the linker can comprise PEG. In some aspects, the linker can be a cleavable linker. Suitable cleavable linkers include, for example, valine-citrulline-para aminobenzyl. In some aspects, the linker can be a disulfide containing linker. In some aspects, the linker can be an acetal-based linker. In some aspects, the linker can be a ketal-based linker. A linker may also be one or more amino acids, alone or in combination with another linker such as one or more PEG groups.

The acyl donor substrate comprising a glutamine residue can be present in, part of, or attached to, a functional agent. Suitable functional agents include, for example, fluorophores, fluorescent dyes, polypeptides, immunoglobulins, antibiotics, nucleic acids, radionuclides, chemical linkers, small molecules, chelators, lipids, nucleic acids (such as DNA or RNA) and drugs. In some aspects, the functional agent can comprise a fluorophore. In some aspects, the functional agent can comprise a fluorescent dye. In some aspects, the functional agent can comprise a polypeptide. In some aspects, the functional agent can comprise an immunoglobulin. In some aspects, the functional agent can comprise an antibiotic. In some aspects, the functional agent can comprise a nucleic acid (such as DNA or RNA). In some aspects, the functional agent can comprise a radionuclide. In some aspects, the functional agent can comprise a small molecule. In some aspects, the functional agent can comprise a chelator (for example, DOTA, CHX-A"-DTPA, NOTA, among others). In some aspects, the functional agent can comprise a lipid. In some aspects, the functional agent can comprise a drug. In some aspects, the functional agent can comprise a combination of any of the above listed functional agents.

The acyl donor substrate (i.e., a first acyl donor substrate) can be bound to a second acyl donor substrate or linker, the second acyl donor substrate or linker being bound to a second immunoglobulin having a second heavy chain variable region and a second light chain variable region, the second heavy chain variable region having a C-terminal lysine, wherein the C-terminal lysine has at least one amino acid residue after the lysine. For example, the first acyl donor substrate and the second acyl donor substrate can have a first and second chemical linker as the first and second functional agents, respectively. The first and second chemical linkers can be bound to each other by a number of suitable means including, for example, by click chemistry.

In one embodiment, the functional agent comprising an acyl donor substrate is according to one of formulae (I) or (II):

(I)

(II)

wherein Z is a carboxylbenzyloxy (CBZ) group or an amino acid residue; Gln is a glutamine amino acid residue; each L is independently a straight or branched linker from 1 to 20 carbon atoms, wherein one or more of the carbon atoms may be optionally and independently replaced with a nitrogen, oxygen or sulfur atom, and wherein each carbon and nitrogen atom may be optionally substituted; or each L is optionally and independently an amino acid residue; m is an integer from 0 to 5; n is an integer from 0 to 5; and Y is a functional agent.

In another embodiment, the acyl donor substrate is according to one of formulae (III) or (IV):

(III)

(IV)

wherein

Z is a carboxylbenzyloxy (CBZ) group or an amino acid residue; Gln is a glutamine amino acid residue; each L is independently a straight or branched linker from 1 to 20 carbon atoms, wherein one or more of the carbon atoms may be optionally and independently replaced with a nitrogen, oxygen or sulfur atom, and wherein each carbon and nitrogen atom may be optionally substituted; or each L is optionally and independently an amino acid residue; m is an integer from 0 to 5; n is an integer from 0 to 5; and X is a reactive group.

In one embodiment, Z is a CBZ group. In another embodiment, Z is an amino acid residue.

In one embodiment, L is an amino acid residue. In one embodiment, n is 2-5, and each L is independently an amino acid residue. In another embodiment, L is a straight or branched linker from 1 to 20 carbon atoms, wherein one or more of the carbon atoms may be optionally and independently replaced with a nitrogen, oxygen or sulfur atom, and wherein each carbon and nitrogen atom may be optionally substituted. In another embodiment, L is a polyethylene glycol (PEG) moiety. In another embodiment, n is 2-5, and one or more L comprises one or more amino acids and one or more additional L groups comprises a polyethylene glycol moiety (PEG).

In one embodiment, m is 0. In another embodiment, m is 1. In another embodiment, m is 2. In another embodiment, m is 3. In another embodiment, m is 4. In another embodiment, m is 5.

In one embodiment, n is 0. In another embodiment, n is 1. In another embodiment, n is 2. In another embodiment, n is 3. In another embodiment, n is 4. In another embodiment, n is 5.

In one embodiment, X is (1R,8S,9s)-bicyclo[6.1.0]non-4-yn-9-ylmethanol (BCN). In another embodiment, X is

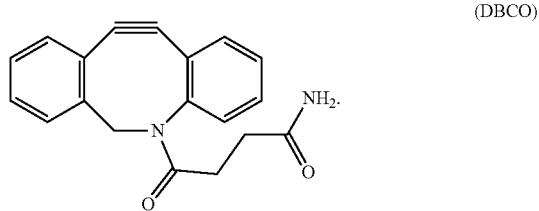 [SMILES: NC(=O)CCC(=O)N1Cc2ccccc2C#Cc2ccccc21]

(DBCO)

In another embodiment, X is trans-cyclooctene (TCO). In another embodiment, X is azido ($N_3$). In another embodiment, X is alkyne. In another embodiment, X is tetrazine methylcyclopropene. In another embodiment, X is nor- bornene. In another embodiment, X is hydrazide/hydrazine. In another embodiment, X is aldehyde.

In one embodiment, for an acyl donor substrate according to formula (I), Z is a CBZ group; L is a polyethylene glycol moiety (PEG) (—O((CH$_2$)$_2$)—), ethyl amine (—NH((CH$_2$)$_2$)—) or propyl amine (—NH((CH$_2$)$_3$)—); and n is 0, 1, 2 or 3.

In another embodiment, the acyl donor substrate is according to formula (I), wherein Z is a CBZ group, and L is an amino acid. In one embodiment, L is Gly. In one aspect of this embodiment, m is 1, and n is 1.

In one embodiment, the acyl donor substrate is according to formula (II), wherein Z is a CBZ group; m is 1; n is 1, 2 or 3; and at least one L is a Gly.

In one embodiment, for an acyl donor substrate according to formula (III), Z is a CBZ group; L is a polyethylene glycol moiety (PEG) (—O((CH$_2$)$_2$)—), ethyl amine (—NH((CH$_2$)$_2$)—) or propyl amine (—NH((CH$_2$)$_3$)—); and n is 0, 1, 2 or 3.

In another embodiment, the acyl donor substrate is according to formula (III), wherein Z is a CBZ group, and L is an amino acid. In one embodiment, L is Gly. In one aspect of this embodiment, m is 1, and n is 1.

In one embodiment, the acyl donor substrate is according to formula (IV), wherein Z is a CBZ group; m is 1; n is 1, 2 or 3; and at least one L is a Gly.

In one embodiment, the immunoglobulin has from 1 to 20 amino acid residues added after the C-terminal lysine (e.g., Lys447). In one embodiment, wherein 1 amino acid residue is added after the C-terminal lysine, the added amino acid residue adjacent to the C-terminal lysine (amino acid position +1) is selected from the group consisting of glycine, alanine, valine, leucine, isoleucine, methionine, phenylalanine, tyrosine, tryptophan, serine, threonine, cysteine, asparagine, glutamine, and histidine. In one embodiment, wherein 1 amino acid residue is added after the C-terminal lysine, the added amino acid residue adjacent to the C-terminal lysine (amino acid position +1) is not proline, aspartic acid, or glutamic acid. In one embodiment, wherein 1 amino acid residue is added after the C-terminal lysine, the added amino acid residue adjacent to the C-terminal lysine (amino acid position +1) is not lysine or arginine.

In one embodiment, the immunoglobulin has 2 amino acid residues (amino acid positions +1 and +2) added after the C-terminal lysine (e.g., Lys447). In one embodiment, the immunoglobulin has 3 amino acid residues (amino acid positions +1, +2, and +3) added after the C-terminal lysine (e.g., Lys447). In one embodiment, the immunoglobulin has 4 amino acid residues (amino acid positions +1, +2, +3, and +4) added after the C-terminal lysine (e.g., Lys447). In one embodiment, the immunoglobulin has 5 amino acid residues (amino acid positions +1, +2, +3, +4 and +5) added after the C-terminal lysine (e.g., Lys447). In one embodiment, the immunoglobulin has 6 amino acid residues (amino acid positions +1, +2, +3, +4, +5, and +6) added after the C-terminal lysine (e.g., Lys447). In one embodiment, the immunoglobulin has 7 amino acid residues (amino acid positions +1, +2, +3, +4, +5, +6, and +7) added after the C-terminal lysine e.g., (Lys447). In one embodiment, the immunoglobulin has 8 amino acid residues (amino acid positions +1, +2, +3, +4, +5, +6, +7, and +8) added after the C-terminal lysine (e.g., Lys447). In one embodiment, the immunoglobulin has 9 amino acid residues (amino acid positions +1, +2, +3, +4, +5, +6, +7, +8, and +9) added after the C-terminal lysine (e.g., Lys447). In one embodiment, the immunoglobulin has 10 amino acid residues (amino acid positions +1, +2, +3, +4, +5, +6, +7, +8, +9, and +10) added after the C-terminal lysine (e.g., Lys447). In one embodiment, the immunoglobulin has 11 amino acid residues (amino acid positions +1, +2, +3, +4, +5, +6, +7, +8, +9, +10, and +11) added after the C-terminal lysine (e.g., Lys447). In one embodiment, the immunoglobulin has 12 amino acid residues (amino acid positions +1, +2, +3, +4, +5, +6, +7, +8, +9, +10, +11, and +12) added after the C-terminal lysine (e.g., Lys447). In one embodiment, the immunoglobulin has 13 amino acid residues (amino acid positions +1, +2, +3, +4, +5, +6, +7, +8, +9, +10, +11, +12, and +13) added after the C-terminal lysine (e.g., Lys447). In one embodiment, the immunoglobulin has 14 amino acid residues (amino acid positions +1, +2, +3, +4, +5, +6, +7, +8, +9, +10, +11, +12, +13, and +14) added after the C-terminal lysine (e.g., Lys447). In one embodiment, the immunoglobulin has 15 amino acid residues (amino acid positions +1, +2, +3, +4, +5, +6, +7, +8, +9, +10, +11, +12, +13, +14, and +15) added after the C-terminal lysine (e.g., Lys447). In one embodiment, the immunoglobulin has 16 amino acid residues (amino acid positions +1, +2, +3, +4, +5, +6, +7, +8, +9, +10, +11, +12, +13, +14, +15, and +16) added after the C-terminal lysine (e.g., Lys447). In one embodiment, the immunoglobulin has 17 amino acid residues (amino acid positions +1, +2, +3, +4, +5, +6, +7, +8, +9, +10, +11, +12, +13, +14, +15, +16, and +17) added after the C-terminal lysine (e.g., Lys447). In one embodiment, the immunoglobulin has 18 amino acid residues (amino acid positions +1, +2, +3, +4, +5, +6, +7, +8, +9, +10, +11, +12, +13, +14, +15, +16, +17, and +18) added after the C-terminal lysine (e.g., Lys447). In one embodiment, the immunoglobulin has 19 amino acid residues (amino acid positions +1, +2, +3, +4, +5, +6, +7, +8, +9, +10, +11, +12, +13, +14, +15, +16, +17, +18, and +19) added after the C-terminal lysine (e.g., Lys447). In one embodiment, the immunoglobulin has 20 amino acid residues (amino acid positions +1, +2, +3, +4, +5, +6, +7, +8, +9, +10, +11, +12, +13, +14, +15, +16, +17, +18, +19, and +20) added after the C-terminal lysine (e.g., Lys447).

In one embodiment, the immunoglobulin has less than 9 amino acid residues added after the C-terminal lysine (e.g., Lys447). In one embodiment, the immunoglobulin has less than 13 amino acid residues added after the C-terminal lysine (e.g., Lys447). In one embodiment, the immunoglobulin does not have the sequence: GTYFQAYGT (SEQ ID NO: 1), GECTYFQAYGCTE (SEQ ID NO: 2) or GENTYFQAYGNTE (SEQ ID NO: 3) added after the C-terminal lysine e.g., Lys447).

In one embodiment, wherein two or more amino acid residues are added or present after the C-terminal lysine, the last amino acid residue added or present after the C-terminal lysine (i.e., the added amino acid residue furthest from the C-terminal lysine) is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, wherein two or more amino acid residues are added or present after the C-terminal lysine, the last amino acid residue added or present after the C-terminal lysine is not lysine or arginine.

The disclosed methods can be performed on a humanized immunoglobulin. Thus, in some embodiments, the immunoglobulin can be a humanized immunoglobulin.

The disclosed methods can be performed on a human immunoglobulin. Thus, in some embodiments, the immunoglobulin can be a human immunoglobulin. In another embodiment, the immunoglobulin can be a non-human immunoglobulin.

In one embodiment, the disclosed methods can be performed on an $IgG_1$, $IgG_2$, $IgG_3$ or $IgG_4$ immunoglobulin. In one embodiment, the method is performed on an $IgG_1$ immunoglobulin. In one embodiment, the method is performed on an $IgG_2$ immunoglobulin. In one embodiment, the method is performed on an $IgG_3$ immunoglobulin. In one embodiment, the method is performed on an $IgG_4$ immunoglobulin.

In one embodiment, the disclosed methods can be performed on an $IgA_1$, $IgA_2$, or IgM immunoglobulin. In one embodiment, the method is performed on an $IgA_1$ immunoglobulin. In one embodiment, the method is performed on an $IgA_2$ immunoglobulin. In one embodiment, the method is performed on an IgM immunoglobulin. In one embodiment, the IgA or IgM immunoglobulin has a tail piece. In another embodiment, the IgA or IgM immunoglobulin has the tail piece removed.

In one embodiment, the method is performed on an IgD or IgE immunoglobulin. In one embodiment, the method is performed on an IgD immunoglobulin. In one embodiment, the method is performed on an IgE immunoglobulin.

For the methods described herein, in one embodiment, the microbial transglutaminase is from *Actinomadura* sp. T-2, *Bacillus circulans* BL32, *Bacillus subtilis* spores, *Corynebacterium ammoniagenes*, *Corynebacterium glutamicum*, *Enterobacter* sp. C2361, *Providencia* sp. C1112, *Streptoverticillium mobaraense* (aka *Streptomyces mobarensis*), *Streptomyces platensis* M5218, *Streptomyces hygroscopicus*, *Streptomyces lividans*, *Streptomyces lividans* JT46/pAE053, *Streptomyces lydicus*, *Streptomyces platensis*, *Streptomyces sioyansis*, *Streptoverticillium griseocarneum*, *Streptoverticillium ladakanum* NRRL-3191, *Streptoverticillium* sp. s-8112, or *Streptococcus suis*. In one embodiment, the microbial transglutaminase is from *Streptomyces mobarensis*.

For the methods described herein, in one embodiment, the transglutaminase is isolated from a plant selected from the group consisting of *Medicago sativa*, *Beta vulgaris*, *Helianthus tuberosus*, *Zea mays*, *Glycine max*, *Arabidopsis thaliana*, *Nicotiana tabacum*, *Chlamydomonas reinhardtii*, *Dunaliella salina*, *Oryza sativa*, and *Rosmarinus officinalis* L.

For the methods described herein, in one embodiment, the transglutaminase is mamillian and is isolated from Transglutaminase 1 thru 7 and Factor XIII.

In one embodiment, the transglutaminase is at least 75%, 80%, 81%, 82%, 83%, 84%, 85%, 86%, 87%, 88%, 89%, 90%, 91%, 92%, 93%, 94%, 95%, 96%, 97%, 98%, or 99% identical to a microbial transglutaminase described herein. In one embodiment, the transglutaminase is at least 75%, 80%, 81%, 82%, 83%, 84%, 85%, 86%, 87%, 88%, 89%, 90%, 91%, 92%, 93%, 94%, 95%, 96%, 97%, 98%, or 99% identical to the microbial transglutaminase is from *Streptomyces mobarensis*. Transglutaminase enzymes can be purchased from Ajinomoto® or Zedira (Product number T001). In another embodiment, the transglutaminase is purified. In another embodiment, the transglutaminase is recombinantly expressed and subsequently purified using methods known to one of ordinary skill in the art.

In one embodiment, the transglutaminase enzyme is present in the methods described herein in a concentration of about 0.1 units/mL to about 250 units/mL. In one embodiment, the transglutaminase enzyme is present in the methods described herein in a concentration of about 1 unit/mL to about 25 units/mL. In one embodiment, the transglutaminase enzyme is present in the methods described herein in a concentration of about 1 unit/mL to about 25 units/mL. In one embodiment, the transglutaminase enzyme is present in the methods described herein in a concentration of about 0.1 unit/mL. In one embodiment, the transglutaminase enzyme is present in the methods described herein in a concentration of about 0.5 unit/mL. In one embodiment, the transglutaminase enzyme is present in the methods described herein in a concentration of about 1 unit/mL. In one embodiment, the transglutaminase enzyme is present in the methods described herein in a concentration of about 5 units/mL. In one embodiment, the transglutaminase enzyme is present in the methods described herein in a concentration of about 10 units/mL. In one embodiment, the transglutaminase enzyme is present in the methods described herein in a concentration of about 15 units/mL. In one embodiment, the transglutaminase enzyme is present in the methods described herein in a concentration of about 20 units/mL. In one embodiment, the transglutaminase enzyme is present in the methods described herein in a concentration of about 25 units/mL. In one embodiment, the transglutaminase enzyme is present in the methods described herein in a concentration of about 50 units/mL. In one embodiment, the transglutaminase enzyme is present in the methods described herein in a concentration of about 75 units/mL. In one embodiment, the transglutaminase enzyme is present in the methods described herein in a concentration of about 100 units/mL. In one embodiment, the transglutaminase enzyme is present in the methods described herein in a concentration of about 150 units/mL, 200 units/mL, or 250 units/mL.

For the methods provided herein, in one embodiment, the ratio of functional agent to immunoglobulin is from about 1:1 to about 2:1. In one embodiment, the ratio of functional agent to immunoglobulin is from about 1:1 to about 2:1. In one embodiment, the ratio of functional agent to immunoglobulin is about 1:1. In one embodiment, the ratio of functional agent to immunoglobulin is about 2:1. In one embodiment, the ratio of functional agent to immunoglobulin is known and is consistently reproducible by following the methods disclosed herein. The ratio of functional agent to immunoglobulin, as used herein, is calculated based on an average of the conjugation ratio of the functional agent to an immunoglobulin in a pool of antibodies in a composition.

In embodiments provided herein, wherein at least two additional amino acid residues are present after the C-terminal lysine, and wherein one of the at least two additional amino acid residues comprises a lysine, the ratio of functional agent to immunoglobulin is increased based on the number of additional amino acid residues which are lysine. For example, wherein two additional amino acid residues are present after a C-terminal lysine, and one of the additional amino acid residues is also a lysine, there are two lysine residues present, resulting in an antibody with four transamidation sites and a ratio of functional agent to immunoglobulin of about 2:1 to about 4:1. As another example, wherein five additional amino acid residues are present after a C-terminal lysine, and two of the additional amino acid residues are lysines, there are three (total) lysine residues present, resulting in an antibody with six transamidation sites and a ratio of functional agent to immunoglobulin of about 2:1 to about 6:1.

Conjugated Immunoglobulins

Also disclosed herein are conjugated immunoglobulins comprising any of the immunoglobulins disclosed herein, wherein the lysine at the C-terminal position (for example, the lysine at position 447, or "Lys447") has at least one additional amino acid residue after the C-terminal lysine, and is conjugated to a functional agent comprising an acyl donor substrate, wherein the acyl donor substrate comprises a glutamine residue. Additional embodiments include conjugated immunoglobulins comprising any of the immunoglobulins disclosed herein, wherein the lysine at the C-terminal position (for example, the lysine at position 447, or "Lys447") has at least one additional amino acid residue after the C-terminal lysine, and is conjugated to an acyl donor substrate, wherein the acyl donor substrate comprises a glutamine residue and a reactive group, wherein the reactive group can be reacted with a functional agent after the conjugation of the acyl donor substrate to the immunoglobulin.

In one embodiment, the amino acid residue adjacent to the C-terminal lysine (amino acid position +1) comprises glycine, alanine, valine, leucine, isoleucine, methionine, phenylalanine, tyrosine, tryptophan, serine, threonine, cysteine, asparagine, glutamine, or histidine. In one embodiment, the amino acid residue adjacent to the C-terminal lysine (amino acid position +1) comprises glycine. In one embodiment, the amino acid residue adjacent to the C-terminal lysine (amino acid position +1) comprises alanine. In one embodiment, the amino acid residue adjacent to the C-terminal lysine (amino acid position +1) comprises valine. In one embodiment, the amino acid residue adjacent to the C-terminal lysine (amino acid position +1) comprises leucine. In one embodiment, the amino acid residue adjacent to the C-terminal lysine (amino acid position +1) comprises isoleucine. In one embodiment, the amino acid residue adjacent to the C-terminal lysine (amino acid position +1) comprises methionine. In one embodiment, the amino acid residue adjacent to the C-terminal lysine (amino acid position +1) comprises phenylalanine. In one embodiment, the amino acid residue adjacent to the C-terminal lysine (amino acid position +1) comprises tyrosine. In one embodiment, the amino acid residue adjacent to the C-terminal lysine (amino acid position +1) comprises tryptophan. In one embodiment, the amino acid residue adjacent to the C-terminal lysine (amino acid position +1) comprises serine. In one embodiment, the amino acid residue adjacent to the C-terminal lysine (amino acid position +1) comprises threonine. In one embodiment, the amino acid residue adjacent to the C-terminal lysine (amino acid position +1) comprises cysteine. In one embodiment, the amino acid residue adjacent to the C-terminal lysine (amino acid position +1) comprises asparagine. In one embodiment, the amino acid residue adjacent to the C-terminal lysine (amino acid position +1) comprises glutamine. In one embodiment, the amino acid residue adjacent to the C-terminal lysine (amino acid position +1) comprises histidine. In one embodiment, wherein 1 amino acid residue is added after the C-terminal lysine, the added amino acid residue adjacent to the C-terminal lysine (amino acid position +1) is not proline, aspartic acid, glutamic acid, lysine, or arginine.

In another embodiment, if more than one amino acid is added to the C-terminal lysine, the last additional amino acid (i.e., the amino acid located at the C-terminus of the added amino acid residues) may be any amino acid, except for lysine or arginine. For example, wherein two amino acid residues are added after the C-terminal lysine, the sequence comprises a first amino acid residue after the C-terminal lysine (amino acid position +1), and a second amino acid after the C-terminal lysine (amino acid position +2), wherein the first amino acid residue after the C-terminal lysine (amino acid position +1) is any amino acid residue except aspartic acid, glutamic acid, or proline, and wherein the second amino acid residue after the C-terminal lysine (amino acid position +2) is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In one embodiment, the first amino acid residue after the C-terminal lysine is lysine or arginine. In another embodiment, the second amino acid residue after the C-terminal lysine (amino acid position +2) is not lysine or arginine.

As another example, wherein five amino acid residues are added after a C-terminal lysine (amino acid positions +1, +2, +3, +4, and +5), the sequence comprises a first amino acid residue after the C-terminal lysine (amino acid position +1), a second amino acid residue after the C-terminal lysine (amino acid position +2), a third amino acid residue after the C-terminal lysine (amino acid position +3), a fourth amino acid residue after the C-terminal lysine (amino acid position +4), and a fifth amino acid residue after the C-terminal lysine (amino acid position +5). The first amino acid residue after the C-terminal lysine may be any amino acid residue except aspartic acid, glutamic acid, or proline. The second, third, and fourth amino acid residues after the C-terminal lysine may be any amino acid. However, the fifth amino acid residue after the C-terminal lysine (amino acid position +5) is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan, and glycine. In another embodiment, the fifth amino acid residue after the C-terminal lysine (amino acid position +5) is not lysine or arginine. In another embodiment, the first, second, third, or fourth amino acid residue(s) (amino acid positions +1, +2, +3, and/or +4) after the C-terminal lysine may each be lysine or arginine.

In some embodiments, the immunoglobulin can be humanized. In other embodiments, the immunoglobulin is human. In another embodiment, the immunoglobulin is chimeric.

The acyl donor substrate comprising a glutamine residue and a reactive group can also comprise a linker, "L". Likewise, the functional agents which contain an acyl donor substrate comprising a glutamine residue can have a linker between the functional agent and the acyl donor substrate portion of the molecule. Linkers can be non-cleavable linkers or cleavable linkers. Exemplary linkers include, for example, disulfide containing linkers, acetal-based linkers, and ketal-based linkers. In some aspects, the linker can be a non-cleavable linker. Suitable non-cleavable linkers include, but are not limited to, polyethylene glycol (PEG) or an alkyl. In some embodiments, the linker can comprise PEG. In some aspects, the linker can be a cleavable linker. Suitable cleavable linkers include, for example, valine-citrulline-para aminobenzyl. In some aspects, the linker can be a disulfide containing linker. In some aspects, the linker can be an acetal-based linker. In some aspects, the linker can be a ketal-based linker.

The conjugated immunoglobulins of the invention comprise a functional agent. Suitable functional agents include, for example, a therapeutic agent or a diagnostic agent. Suitable functional agents include, for example, fluorophores, fluorescent dyes, polypeptides, immunoglobulins, antibiotics, nucleic acids, radionuclides, chemical linkers, small molecules, chelators, lipids, and drugs. In some aspects, the functional agent can comprise a fluorophore. In some aspects, the functional agent can comprise a fluorescent dye. In some aspects, the functional agent can comprise a polypeptide. In some aspects, the functional agent can comprise an immunoglobulin. In some aspects, the functional agent can comprise an antibiotic. In some aspects, the functional agent can comprise a nucleic acid (such as DNA or RNA). In some aspects, the functional agent can comprise a radionuclide. In some aspects, the functional agent can comprise a small molecule. In some aspects, the functional agent can comprise a chelator (for example, DOTA, CHX-A"-DTPA, NOTA, among others). In some aspects, the functional agent can comprise a lipid. In some aspects, the functional agent can comprise a drug. In some aspects, the functional agent can comprise a combination of any of the above listed functional agents.

Accordingly, the disclosed conjugated immunoglobulins include, but are not limited to, immunoglobulin-fluorophore C-terminal lysine conjugates, immunoglobulin-fluorescent dye C-terminal lysine conjugates, immunoglobulin-polypeptide C-terminal lysine conjugates, immunoglobulin-immunoglobulin C-terminal lysine conjugates, immunoglobulin-antibiotic C-terminal lysine conjugates, immunoglobulin-nucleic acid C-terminal lysine conjugates, immunoglobulin-radionuclide C-terminal lysine conjugates, immunoglobulin-chemical linker C-terminal lysine conjugates, immunoglobulin-small molecule C-terminal lysine conjugates, immunoglobulin-chelator C-terminal lysine conjugates, immunoglobulin-lipid C-terminal lysine conjugates, and immunoglobulin-drug C-terminal lysine conjugates.

Any of the immunoglobulins disclosed herein can be conjugated to any of the functional agents disclosed herein. For example, the conjugated immunoglobulin can comprise a fluorophore, fluorescent dye, polypeptide, immunoglobulin, antibiotic, nucleic acid, radionuclide, chemical linker, small molecule, chelator, lipid, or drug.

In some embodiments, the immunoglobulin can be conjugated to a small molecule antineoplastic agent, such as an auristatin. In some aspects, the functional agent can be auristatin F (AuF). Thus, the disclosed conjugated immunoglobulins include any of the above disclosed immunoglobulins conjugated to auristatin F (AuF Lys447 conjugate).

Pharmaceutical Compositions

Also provided herein are pharmaceutical compositions. In some embodiments, the pharmaceutical compositions can comprise any of the immunoglobulins disclosed herein. In some embodiments, the pharmaceutical compositions can comprise any of the conjugated immunoglobulins disclosed herein. In one embodiment, the pharmaceutical composition comprises the conjugated immunoglobulin and a pharmaceutically acceptable carrier.

Nucleic Acid Molecules Encoding Immunoglobulins and Host Cells Comprising the Same Also provided herein are nucleic acid molecules encoding any of the immunoglobulins disclosed herein. As an example, in one embodiment, the nucleic acid molecule encodes an immunoglobulin comprising a heavy chain variable region and a light chain variable region, the light chain variable region having a lysine at the C-terminal position (for example, position 447 or "Lys447") and one or more amino acids after the C-terminal lysine selected from glycine, alanine, valine, leucine, isoleucine, methionine, phenylalanine, tyrosine, tryptophan, serine, threonine, cysteine, asparagine, glutamine and histidine.

Also disclosed are host cells comprising any of the disclosed nucleic acid molecules. Suitable host cells include, but are not limited to, mammalian cells, bacterial cells, yeast cells, insect cells, to name a few.

The following examples are provided to further describe some of the embodiments disclosed herein. The examples are intended to illustrate, not to limit, the disclosed embodiments.

EXAMPLES

Example 1: Materials & Methods

Mutagenesis

Mutations were generated using Stratagene's QuikChange XL according to the manufacturer's protocol. The desired mutations were confirmed by DNA sequencing.

Transfection and Stable Cell Line Generation

For each milliliter of cells to be transfected with Expi-Fectamine, 333.3 ng HC plasmid and 333.3 ng LC plasmid was incubated for 5-10 min in 50 µL Opti-MEM (ThermoFisher). Likewise, 2.67 µL ExpiFectamine was incubated in 50 µL Opti-MEM. The ExpiFectamine solution was added to the DNA mixture, and incubated for 20-30 min at room temperature. The DNA:ExpiFectamine mixture was added to the cells while swirling and incubated at 37° C., 8% $CO_2$, shaking at 125 rpm. The following day, 5 µL of enhancer 1 and 50 µL of enhancer 2 per mL of cells were added to the transfection with continued incubation for another 7-10 days.

Antibody-expressing stable pools were selected by adding 1 mL of transfectants to 14 mL DMEM in a T75 flask with 5 µg/mL blasticidin and 400 µg/mL zeocin (Invivogen) one to three days after transfection. After drug-resistant cells grew to confluency, the medium was replaced with FreeStyle 293 expression medium for 24 to 48 h. Cells were physically dislodged by tapping the flask (trypsinization resulted in low viability, data not shown) and were then seeded at $6 \times 10^5$ cells/mL in 30 mL FreeStyle 293 expression medium in a 125-mL shake flask. Cultures were incubated at 37° C. in 8% $CO_2$ with shaking at 125 rpm.

MAb Production

Stably-transfected cell line pools were seeded at 0.6 to $1 \times 10^6$ cells/mL in FreeStyle 293 expression medium. Cells were incubated at 37° C., 8% $CO_2$, shaking at 125 rpm. Two days after the culture reached a density of $1 \times 10^6$ cells/mL, cultures were fed with final concentrations of 10 g/L Select Soytone (BD Biosciences), 5 mM valeric acid (Sigma Aldrich), and 1:100 CD Lipid Concentrate (ThermoFisher). When the cell viability was less than 50% (7-10 days), the cultures were centrifuged for 1 h at 8000 rpm in a Beckman JLA8.1000 rotor. The supernatant was then filtered through a 0.2 µm PES filter and stored at 4° C. or −20° C. until purification.

MAb Purification

MAbs were purified using one of two methods. For mAb supernatants less than 10 mL, affinity chromatography was performed using a batch purification method with protein A resin. MAb supernatants greater than 25 mL were purified using pre-packed protein A columns.

Batch Purification

Prosep-vA High Capacity Protein A resin (Millipore) was equilibrated with DPBS, and 100 µL were added to 3 to 6 mL of sample. Following incubation at 4° C. for 1 hour to overnight, the resin was washed three times with 1 mL DPBS and centrifuged at 18,000×g for 30 s. The sample was eluted from the resin by addition of 400 µL 0.1 M Glycine, pH 2.9 followed by centrifugation at 18,000×g for 30 s. The sample was neutralized with 40 µL of 1 M Tris, pH 8.0. The buffer was exchanged using 0.5 mL Amicon Ultra, 10k cutoff filters (Millipore) by concentrating the sample to ~100 µL by centrifugation at 18,000×g for 3 to 5 minutes. The concentrated sample was diluted in 400 µL DPBS, followed by centrifugation. The process was repeated a total of four times.

Column Purification

A protein A column (GE Healthcare) was equilibrated with 10 column volumes (CV) of 20 mM sodium phosphate, 10 mM EDTA, pH 7.2. The sample was then loaded, followed by washing unbound material with 10 CV of equilibration buffer. The sample was eluted using 5 CV of 0.1 M Glycine, pH 2.9. The fractions containing the mAb were pooled and dialyzed in DPBS using a MWCO 20K Slide-A-Lyzer (ThermoFisher).

Z-Gln-Gly Substrate Synthesis

Z-Gln-Gly-OH was purchased from Bachem, and Z-Gln-Gly-CAD-biotin was purchased from Zedira (FIG. 2).

Figure 3:
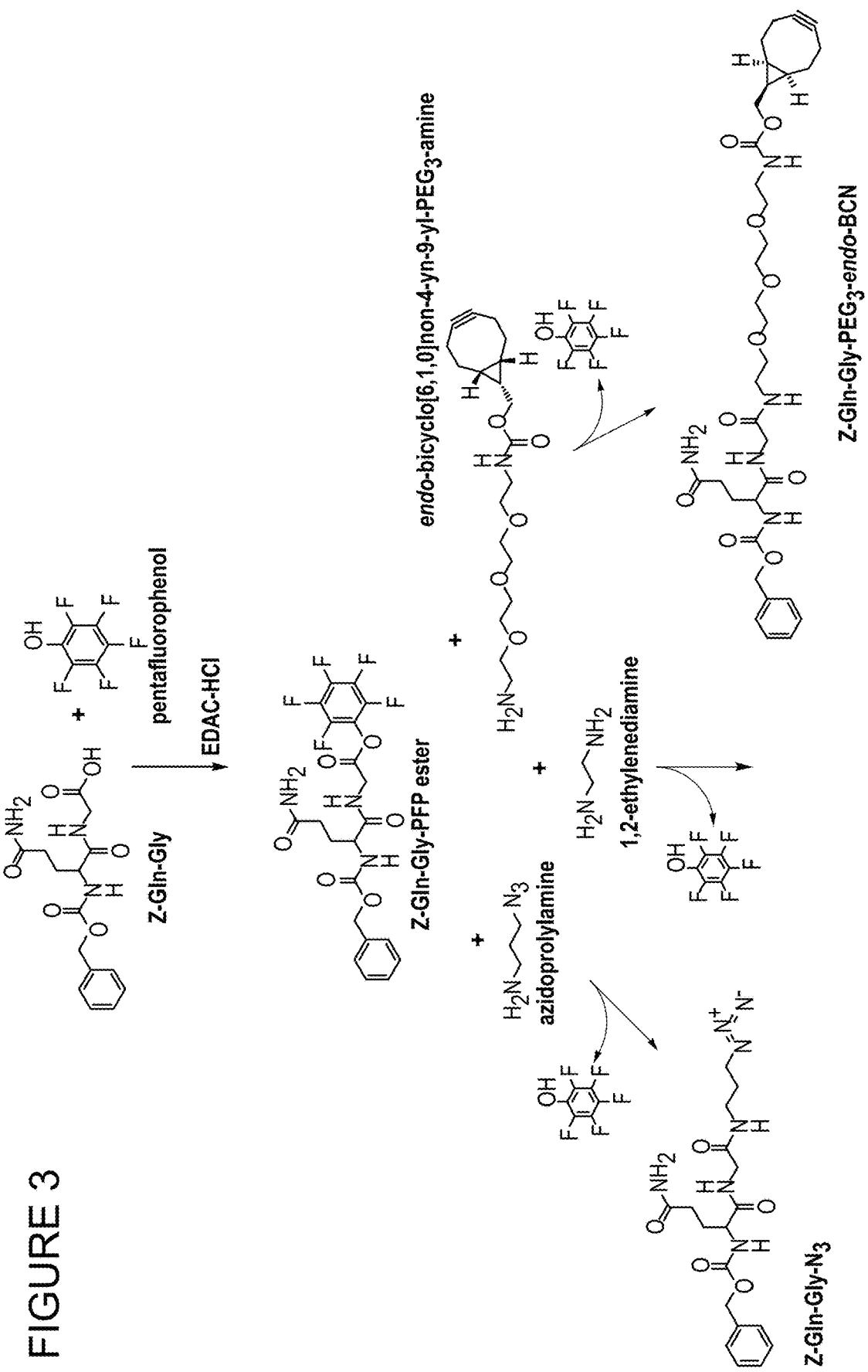
FIG. 3, shows possible routes to synthesize some of the exemplary Z-Gln-Gly acyl-donor substrates.
Figure 3:
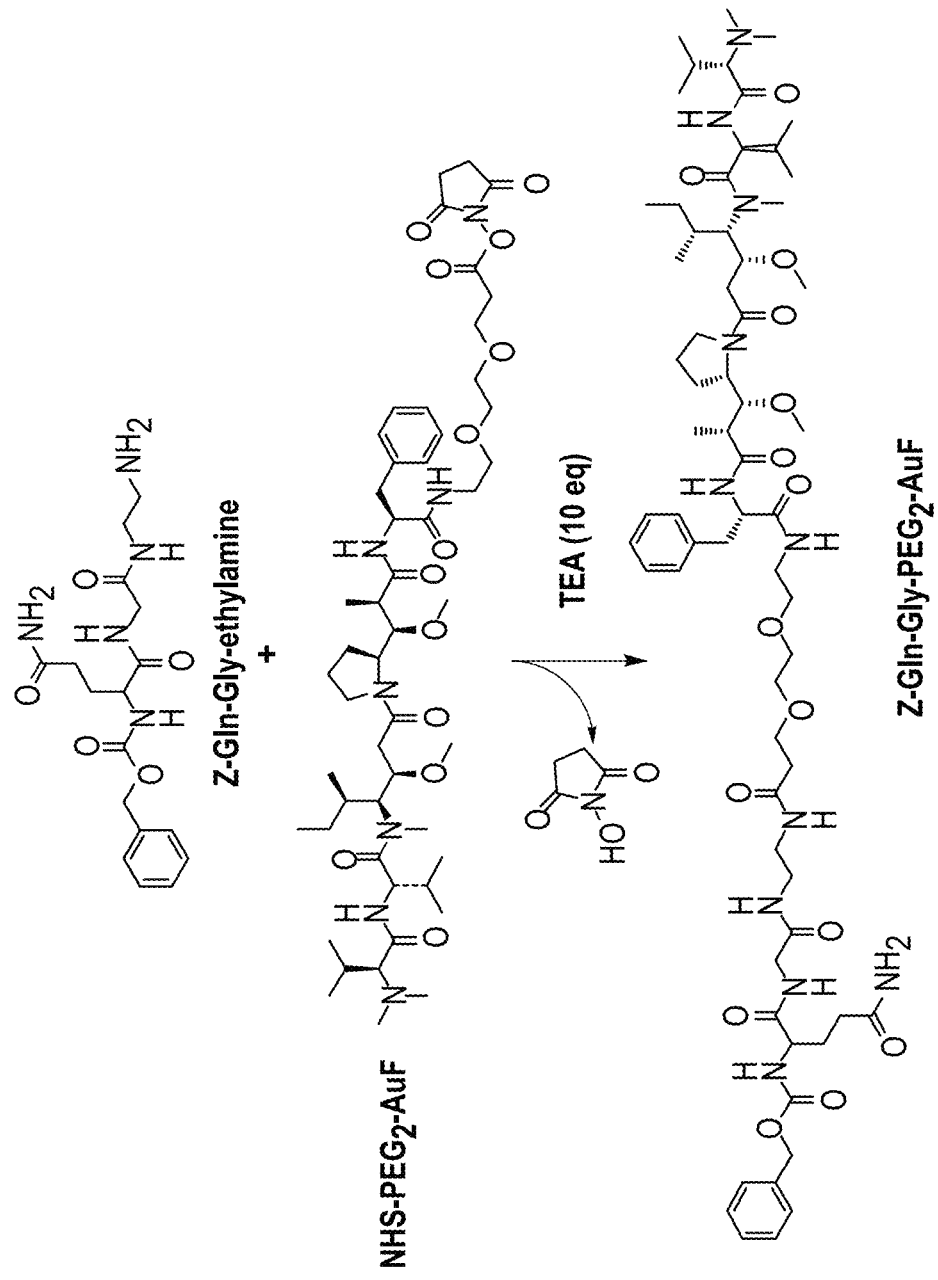
Figure 6A:
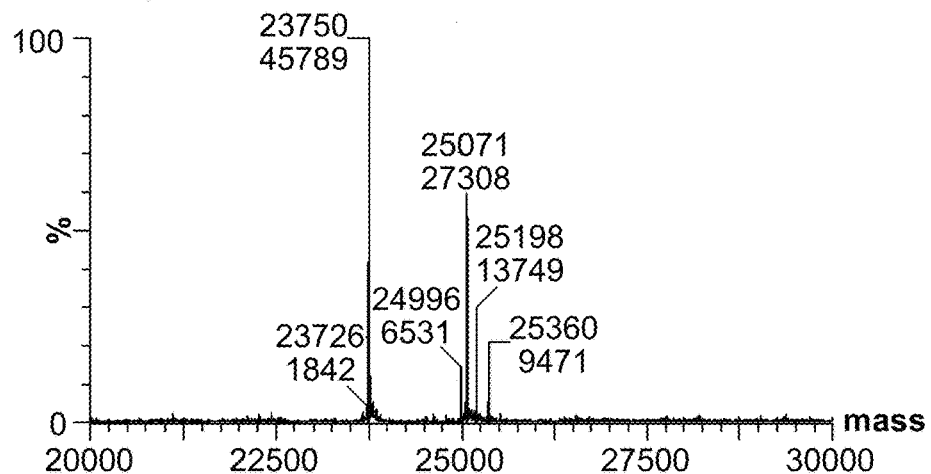
FIGS. 6A, 6B, 6C, 6D, 6E, and 6F, shows ESI-MS analysis of antibodies incubated with an acyl donor and microbial transglutaminase. Antibodies were incubated with 50-fold molar excess Z-Gln-Gly-CAD-biotin and 1 U/mL microbial transglutaminase overnight at 37° C. Following IdeS digestion and reduction, the LC, Fd, and Fc masses were determined by ESI-MS.
Figure 6B:
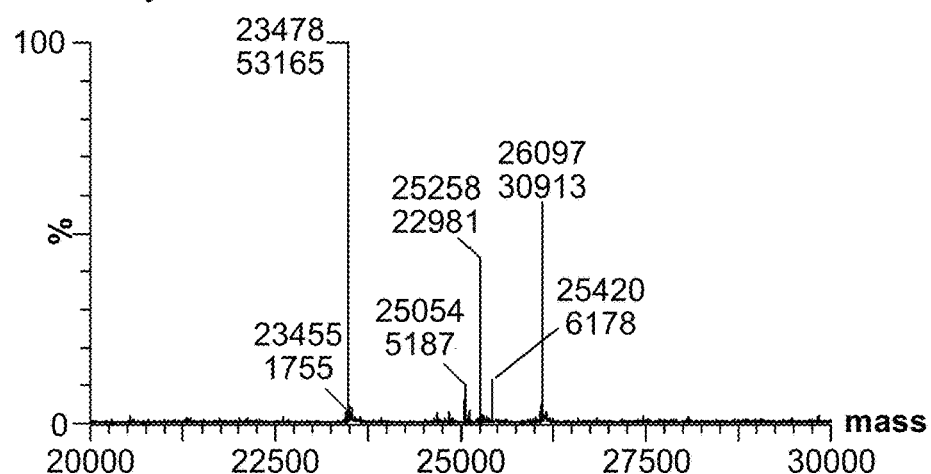
Figure 6C:
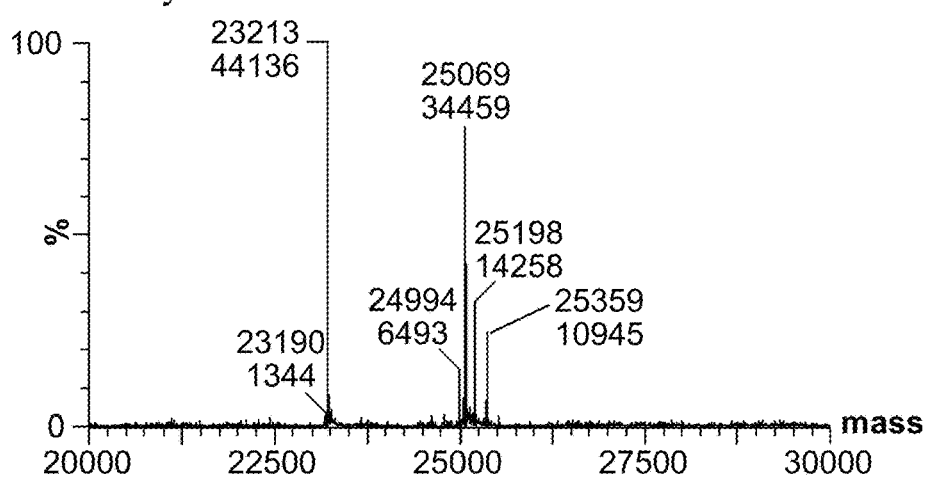
Figure 6D:
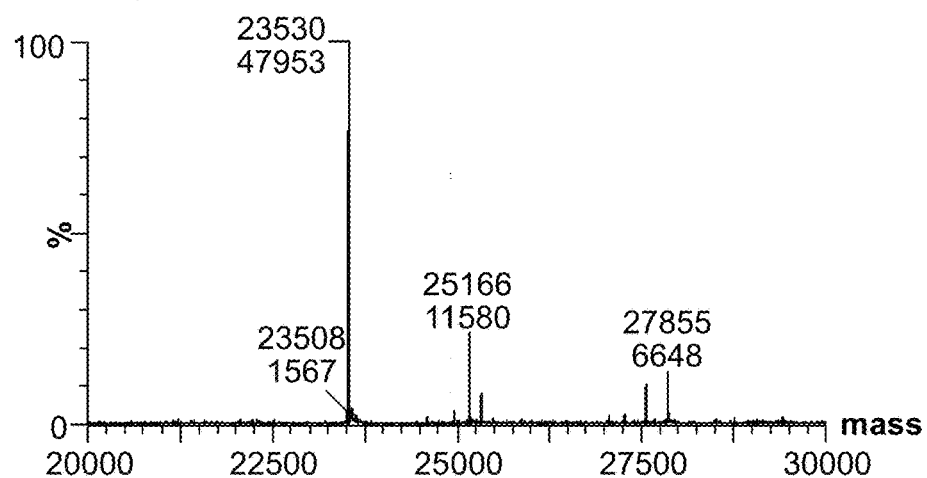
Figure 6E:
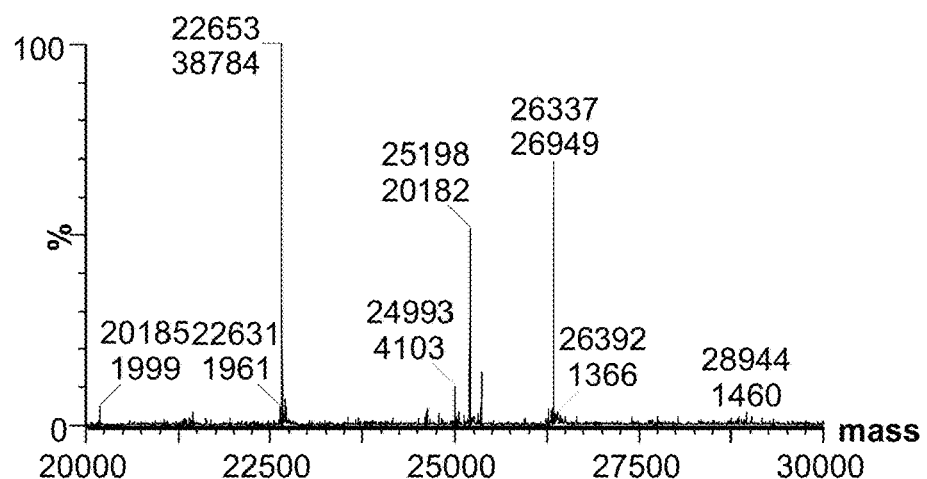
Figure 6F:
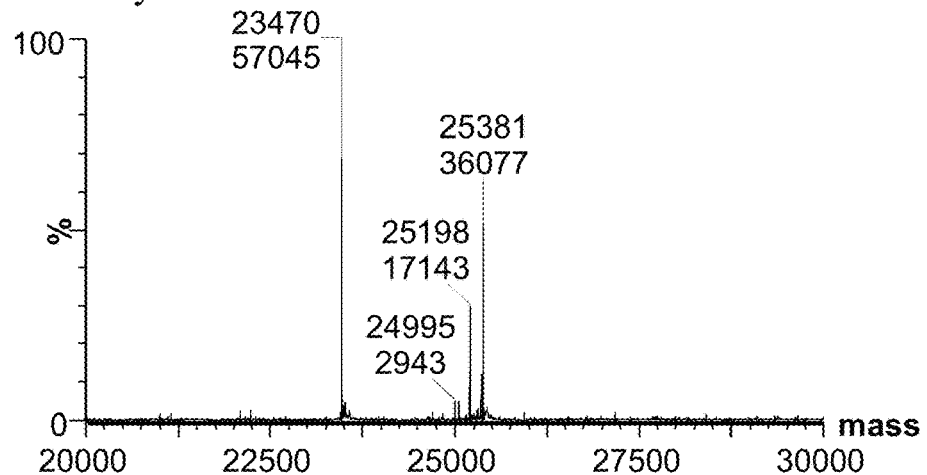

Z-Gln-Gly-pentafluorophenyl ester (Z-Gln-Gly-PFP) Synthesis was from Pasternack et al. {Pasternack, 1997 15/id}, with modifications (FIG. 3). Z-Gln-Gly-OH (328.8 mg, 0.975 mmol) and pentafluorophenol (Sigma, 183.3 mg, 0.996 mmol) were dissolved in 10 mL N,N'-dimethylformamide (DMF). EDAC-HCl (Sigma, 201 mg, 1.04 mmol) was then added and the reaction was incubated at room temperature under $N_2$ for 2 hr. 100 mL of cold diethyl ether was added to the reaction and precipitated overnight at −80° C. The crude product was collected by centrifugation and re-crystallized from 20 mL 60° C. methanol. The final product was rinsed with cold diethyl ether and dried over a stream of $N_2$. Final yield was 219.04 mg (44.7%). ESI-MS (direct infusion in 50% acetonitrile in 0.1% formic acid) m/z 504.0 ([M+H], 86%), 526.0 ([M+Na], 100%), 542.0 ([M+K], 22%).

Z-Gln-Gly-propyl azide (Z-Gln-Gly-$N_3$)

Z-Gln-Gly-PFP (21.24 mg, $4.22 \times 10^{-5}$ mol) and azidopropylamine (Click Chemistry Tools, 42.2 µL of a 0.91 M stock solution in DMF, $3.84 \times 10^{-5}$ mol) were dissolved in 0.42 mL final volume of DMF. Reaction was stirred under N2 overnight at room temperature. Product was purified by HPLC using a 0.1% formic acid in $H_2O$/0.1% formic acid in acetonitrile mobile phase. Product was dried in vacuo. Final yield was 10.7 mg (60.4%). ESI-MS (gradient purification) m/z 420.2 ([M+H], 100%), 442.1 ([M+Na], 32%).

Z-Gln-Gly-$PEG_3$-endo-bicyclononyne (Z-Gln-Gly-$PEG_3$-BCN)

Z-Gln-Gly-PFP (18.4 mg, $3.66 \times 10^{-5}$ mol) and endo-bicyclo[6,1,0]non-4-yn-9-yl-$PEG_3$-amine (Conju-Probe, 175 µL of a 0.27 M stock solution in DMF, $4.75 \times 10^{-5}$ mol) were dissolved in 0.37 mL final volume of DMF. Reaction was stirred under $N_2$ overnight at room temperature. Product was purified by HPLC using a 0.1% formic acid in $H_2O$/ 0.1% formic acid in acetonitrile mobile phase. Product was dried in vacuo. Final yield was 0.6 mg (2%). ESI-MS (gradient purification) m/z 688.2 ([M+H], 100%), 710.2 ([M+Na], 69%).

Z-Gln-Gly-$PEG_2$-Auristatin F (Z-Gln-Gly-$PEG_2$-AuF)

Z-Gln-Gly-PFP (22.2 mg, $4.37 \times 10^{-5}$ mol) was dissolved in 0.85 mL DMF and 1,2-ethylenediamine ($2.3 \times 10^{-5}$ L, $3.5 \times 10^{-4}$ mol) was added and mixed. Reaction was stirred under $N_2$ overnight at room temperature. Product was purified by HPLC using a 0.1% formic acid in $H_2O$/0.1% formic acid in acetonitrile mobile phase. Product was dried in vacuo. Final yield of Z-Gln-Gly-$NH_2$ was 3.8 mg (23%). ESI-MS (gradient purification) m/z 380.1 ([M+H], 100%). Z-Gln-Gly-NH2 (3.8 mg, $1.01 \times 10^{-5}$ mol) and NHS-$PEG_2$-AuF (10.3 mg, $1.03 \times 10^{-5}$ mol) were dissolved in 0.2 mL DMF. Triethylamine (14 µL, $1 \times 10^{-4}$ mol) was added and reaction was incubated under $N_2$ overnight at room temperature. Half of the reaction was purified by HPLC using a 0.1% formic acid in H$_2$O/0.1% formic acid in acetonitrile mobile phase. Product was dried in vacuo. Final yield of CBZ-Gln-Gly-PEG$_2$-AuF was 3.8 mg (60%). ESI-MS (gradient purification) m/z 634.0 ([M+H]$^{2+}$, 100%), 645.1 ([M+ Na]$^{2+}$, 45%). 1267.0 ([M+H], 16%).

Microbial Transglutaminase Reaction

MAbs ranging in concentrations from 100 μg/mL to 2.5 mg/mL were incubated with 785 μM Z-Gln-Gly-biotin (Zedira), Z-Gln-Gly-N$_3$, Z-Gln-Gly-BCN, or Z-Gln-Gly-PEG$_2$-AuF with 1 U/mL microbial transglutaminase (Zedira) in DPBS for at least 16 h at 37° C.

Ultra-Performance Liquid Chromatography (UPLC)/ESI-MS Analysis of mAb Conjugation Purified antibodies were diluted to 1 mg/mL in DPBS (if below 1.0 mg/mL samples were left at original concentration). Reactions containing dimethylsulfoxide (DMSO) were desalted using a Zeba spin desalting column. The mAbs were then either deglycosylated using PNGase F (NEB) or digested into Fab'$_2$ and Fc fragments by IdeS (Promega). To deglycosylate the mAbs, G7 buffer (5 or 10 μL) and PNGase F (1 or 2 μL) were added to the mAb (50 or 100 μL). The reaction was incubated in a Discover microwave (CEM) for 2 cycles: 1.) microwave power 10 W, 37° C., 10 min, and then wait for 3-5 min; 2.) microwave power 2 W, 37° C., 10 min. A portion of the deglycosylated sample was reduced by adding dithiothreitol (DTT) to a final concentration of 20 mM, followed by incubation at 60° C. for 3 min. To generate Fab'$_2$ and Fc fragments, 50 U/μL of IdeS was added to 0.5 mg/mL of mAb and incubated at 37° C. for 0.5-1 h. The IdeS samples were not reduced except for Antibody 01-C which was reduced as above.

Samples were then analyzed using a Waters Acquity UPLC and Q-Tof Premier mass spectrometer. Samples (0.5-2 μg each) were injected onto a MassPrep micro desalting column at 65° C., eluted from the column with a 5 min equilibration in 95% of mobile phase A, a 10 min gradient (5-90% B), and a 10 min re-equilibration in 95% of mobile phase A, at 0.05 mL/min. Mobile phase A was 0.1% formic acid in water. Mobile phase B was 0.1% formic acid in acetonitrile. The Q-Tof mass spectrometer was run in positive ion, V-mode with detection in the range of 500-4000 m/z. The source parameters were as follows: capillary voltage, 2.25 kV (intact antibody)-2.50 kV (reduced antibody); sampling cone voltage, 65.0 V (intact antibody) or 50.0 V (reduced antibody); source temperature, 100° C.; desolvation temperature, 250° C.; desolvation gas flow, 550 L/hr. The protein peak was deconvoluted using the MassLynx MaxEnt 1 function.

Reverse Phase Liquid Chromatography (LC)-MS

Antibody 01-L (1 mg/mL) was incubated overnight with a 50-fold molar excess of Z-Gln-Gly-PEG$_2$-AuF in the presence of 1 U/mL TGase at 37° C. The mAb was digested into Fab'$_2$ and Fc fragments by IdeS and reduced with DTT as above. The sample was analyzed using Waters Alliance HPLC with SQD and PDA detectors. The sample (0.5-2 μg) was injected onto a Proteomix RP-1000 column (4.6×50 mm, Sepax) at 65° C. Separation of the LC, Fc, and Fd fragments occurred with a 1.5 minutes equilibration in 75% of mobile phase A (0.1% TFA in water), and a 13.5-minute gradient [25-65% mobile phase B (0.1% TFA in acetonitrile)] at a flow rate of 1 mL/min.

The SQD mass spectrometer was run in positive ion, V-mode with detection in the range of 200-2000 m/z. Source parameters were as follows: capillary voltage, 3.00 kV; sampling cone voltage, 40° C.; source temperature, 120° C.; desolvation temperature, 250° C.; desolvation gas flow, 800 L/hr. Scan time, 1 second. The protein peak was deconvoluted by the MassLynx MaxEnt 1 function. The PDA detector was at 280 nm.

Example 2: Analysis of Solvent Exposed Lysines on IgG Antibodies

The crystal structures of an IgG1-kappa Fab (Antibody 01, 4F3F), an IgG1-lambda Fab (4HK0), and IgG1 Fc (1FC1) were examined for potential acyl acceptor sites. As microbial transglutaminase tends to prefer solvent-exposed substrate glutamines and lysines within loops {Spolaore, 2012 17/id}, solvent exposed lysines were highlighted using Discovery Studio v4.5 with a 1.4 Å probe radius (FIG. 4). There are 7 solvent exposed lysines in the Antibody 01 VH with 3 in loops. As the number of lysines can vary between mAbs due to utilization of different variable region families and somatic hypermutation, the solvent exposure of lysines in the VH region of five other antibodies were also analyzed based on analogous positions of residues in the 4F3F structure. These VH regions potentially contain 1-5 solvent exposed lysines with 1 or 2 present in a loop. In the Antibody 01 Vκ there are 6 solvent exposed lysines and 4 are in loops. The VK regions from four other antibodies potentially contain 3-5 solvent exposed lysines with 2 in a loop. Antibody 05 utilizes a lambda chain, and the solvent exposure of the lysines was determined using the crystal structure of 4HK0 based on sequence similarity of the light chain. Antibody 05 potentially has 2 solvent exposed lysines in the Vλ domain with only 1 in a loop.

The constant domains of CH1 and kappa, Fc, and lambda were analyzed using the crystal structures of 4F3F, 1FC1, and 4HK0, respectively. The IgG$_1$ constant domains have 23 solvent exposed lysines with 13 in loops. The kappa constant region has 8 lysines with 5 in a loop. The lambda has 6 solvent exposed lysines with half in loops. In total, the analyzed antibodies range from 42 to 50 solvent exposed lysines in loops per mAb.

To determine whether microbial transglutaminase can transamidate a native lysine residue on an IgG antibody, antibodies were incubated with a 50-fold molar excess of Z-Gln-Gly-CAD-biotin and 1 U/mL microbial transglutaminase at 37° C. overnight. The samples were digested with IdeS and reduced with DTT, and the masses of the LC, Fd, and Fc fragments were analyzed by mass spectrometry. The samples were not deglycosylated, and two mass peaks corresponding to the G0F (+1445 Da) and G1F (+1608 Da) glycoforms were observed for each Fc. Antibody 04 also contains an N-linked glycosylation site in VH and two glycan species, G2FS and G2FS2 were observed. All samples lacked the C-terminal lysine (128 Da), as evidenced by the −130 to −132 Da difference between the observed and theoretical mass for the Fc. Although there are 42-50 potential acyl acceptor lysines in the different antibodies, neither the HC nor the LC was modified by the acyl donor substrate (FIG. 6, Table 1).

TABLE 1

ESI-MS analysis of antibodies incubated with an acyl donor and microbial transglutaminase
ZQG-CAD-biotin: +631 Da

|  | LC | | | Fd | | | | Fc | | | |
| --- | --- | --- | --- | --- | --- | --- | --- | --- | --- | --- | --- |
|  | Calculated | Observed | ΔMass | Calculated | Observed | Glycan | ΔMass | Calculated | Glycan | Observed | ΔMass |
| Antibody 02 | 23751 | 23750 | −1 | 25073 | 25071 |  | −2 | 25328 | G0F | 25198 | −130 |
|  |  |  |  |  |  |  |  | 25491 | G1F | 25360 | −131 |
| Antibody 03 | 23478 | 23478 | 0 | 26097 | 26097 |  | 0 | 25388 | G0F | 25258 | −130 |
|  |  |  |  |  |  |  |  | 25551 | G1F | 25420 | −131 |
| Antibody 01 | 23216 | 23213 | −3 | 25072 | 25069 |  | −3 | 25328 | G0F | 25198 | −130 |
|  |  |  |  |  |  |  |  | 25491 | G1F | 25359 | −132 |
| Antibody 04 | 23532 | 23530 | −2 | 27566 | 27564 | G2FS | −2 | 25296 | G0F | 25166 | −130 |
|  |  |  |  | 27857 | 27855 | G2FS2 | −2 | 25459 | G1F | 25327 | −132 |
| Antibody 05 | 22655 | 22653 | −2 | 26340 | 26337 |  | −3 | 25328 | G0F | 25198 | −130 |
|  |  |  |  |  |  |  |  | 25491 | G1F | 25360 | −131 |
| Antibody 05 | 23472 | 23470 | −2 | 25383 | 25381 |  | −2 | 25328 | G0F | 25198 | −130 |
|  |  |  |  |  |  |  |  | 25491 | G1F | 25359 | −132 |

Table 1: The masses of the LC, Fd, and Fc were determined by ESI-MS in FIG. 6. The theoretical mass of each fragment was determined by the amino acid sequence subtracted from the observed mass to determine the change in mass (Δmass). A Δmass of −128 Da is due to cleavage of Lys447. The Fc is glycosylated with one or two oligosaccharides, G0F or G1F.

Figure 7A:
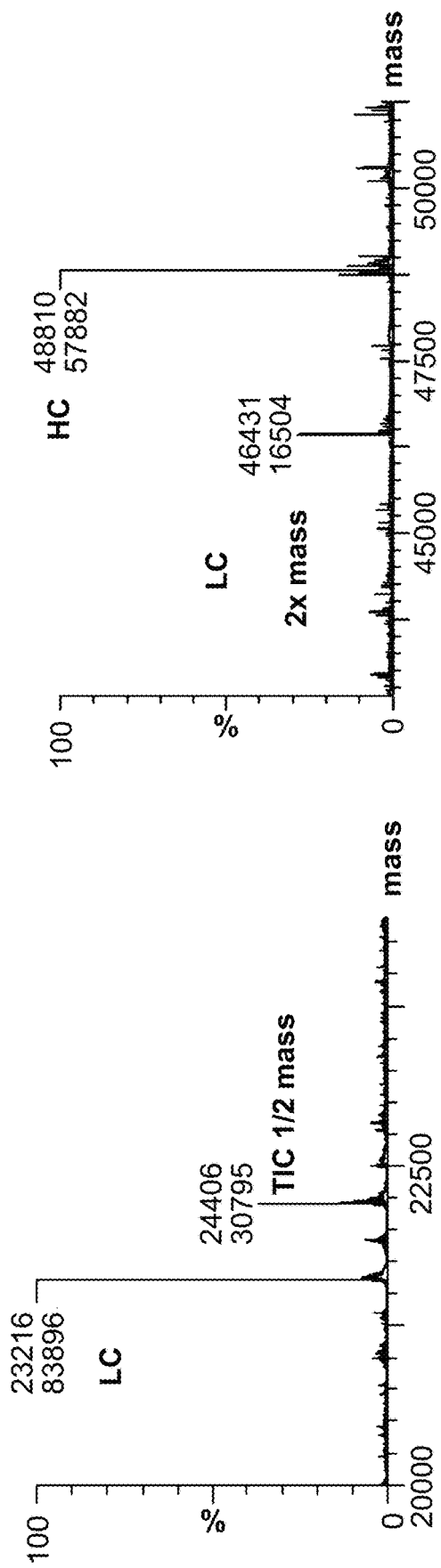
FIGS. 7A, 7B and 7C, shows ESI-MS analysis of Antibody 01 and K-Tag microbial transglutaminase reactions. MAbs were incubated with Z-Gln-Gly-CAD-biotin and microbial transglutaminase overnight at 37° C. Following deglycosylation and reduction, the HC and LC masses of (A) Antibody 01, (B) Antibody 01-HC-KTag, and (C) Antibody 01-LC-KTag were determined by ESI-MS.
Figure 7B:
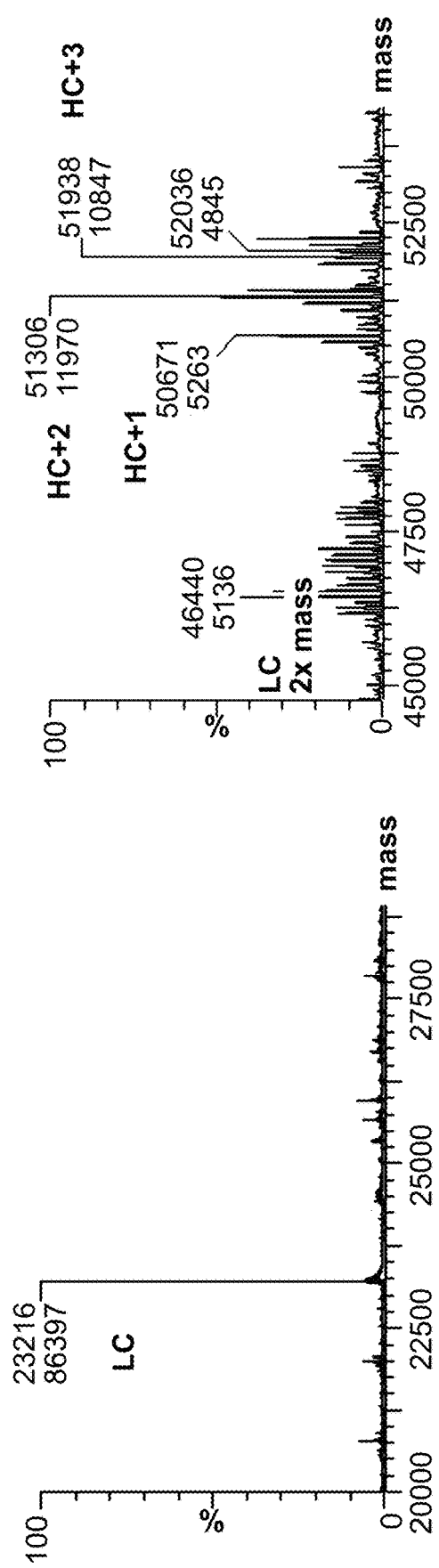
Figure 7C:
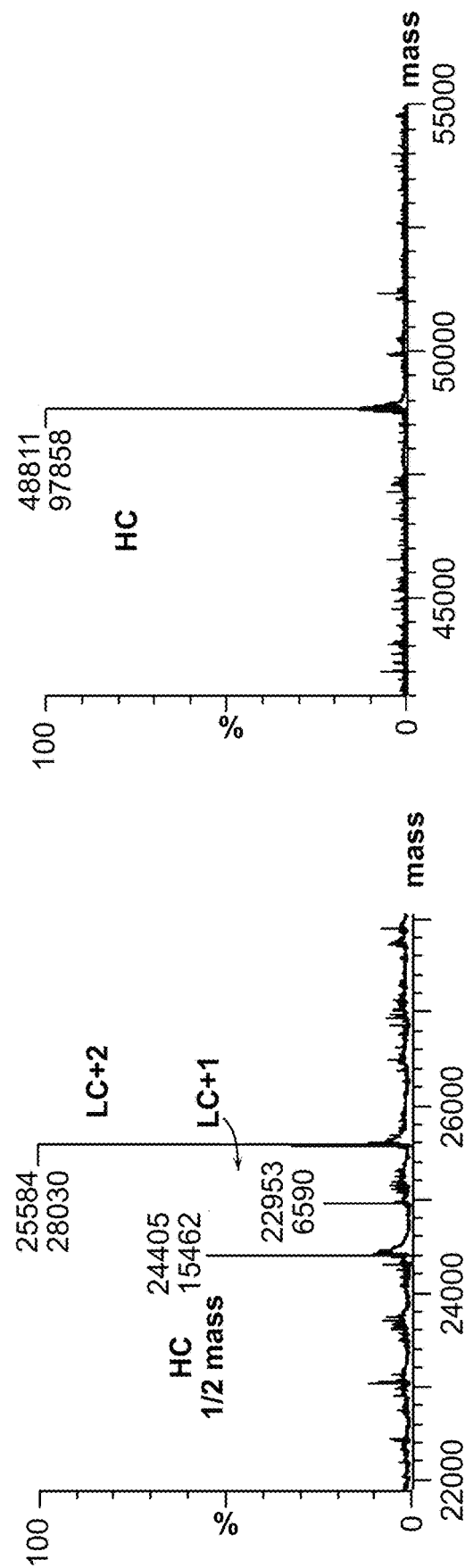

Two positive controls generated containing a peptide with two known lysine acyl acceptor sites (GGSTKHKIPGGS (SEQ ID NO: 6); {Takazawa, 2004 23/id} genetically fused to the C terminus of Antibody 01 HC or LC (HC-KTag or LC-KTag, respectively) were analyzed as well. The KTag mAbs were incubated with Z-Gln-Gly-CAD-biotin and microbial transglutaminase. The samples were deglycosylated by PNGase F and reduced with DTT. The masses of the heavy and light chains were analyzed by mass spectrometry. The LC-KTag mAb was modified with up to two Z-Gln-Gly-CAD-biotin molecules, consistent with modification of the two lysines in the KTag (FIG. 7, Table 2).

TABLE 2

Transamidation of a C-terminal K-Tag
Z-Gln-Gly-CAD-biotin: +631 Da

|  | Calculated | Observed | ΔMass | # Biotins | % conjugated |
| --- | --- | --- | --- | --- | --- |
| LC |  |  |  |  |  |
| Antibody 01 | 23216 | 23216 | 0 | 0 | 0.0% |
| HC-KTag | 23216 | 23216 | 0 | 0 | 0.0% |
| LC-KTag | 24323 | 24953 | 630 | 1.00 | 19.0% |
|  | 24323 | 25584 | 1261 | 2.00 | 81.0% |
| HC |  |  |  |  |  |
| Antibody 01 | 48937 | 48810 | −127 | 0 | 0.0% |
| HC-KTag | 50044 | 50671 | 627 | 0.99 | 18.7% |
|  | 50044 | 51306 | 1262 | 2.00 | 42.6% |
|  | 50044 | 51938 | 1894 | 3.00 | 38.6% |
| LC-KTag | 48809 | 48811 | 2 | 0 | 0.0% |

The masses of the HC and LC were determined by ESI-MS in FIG. 7. The theoretical mass of each fragment was determined by the amino acid sequence subtracted from the observed mass to determine the change in mass (Δmass). A Δmass of −128 Da is due to cleavage of Lys447, and a Δmass of +631 Da indicates addition of one Z-Gln-Gly-CAD-biotin. The number of Z-Gln-Gly-CAD-biotin molecules conjugated onto the HC or LC was determined by dividing the change in mass by the mass of Z-Gln-Gly-CAD-biotin. The percentage of conjugation was determined by dividing the signal intensity of a single HC or LC peak by the sum of the intensities of all HC or LC peaks in the sample.

Addition of the KTag to the HC surprisingly resulted in the addition of not just two, but up to three Z-Gln-Gly-CAD-biotin molecules to the HC. As there are only two lysines in the KTag, a lysine in the mAb was the third acyl acceptor site. Given the proximity to the KTag, the most likely mAb lysine acceptor site was heavy chain Lys447.

Example 3: A Single Amino Acid Extension is Sufficient for Transamidation of Lys447

Figure 8A:
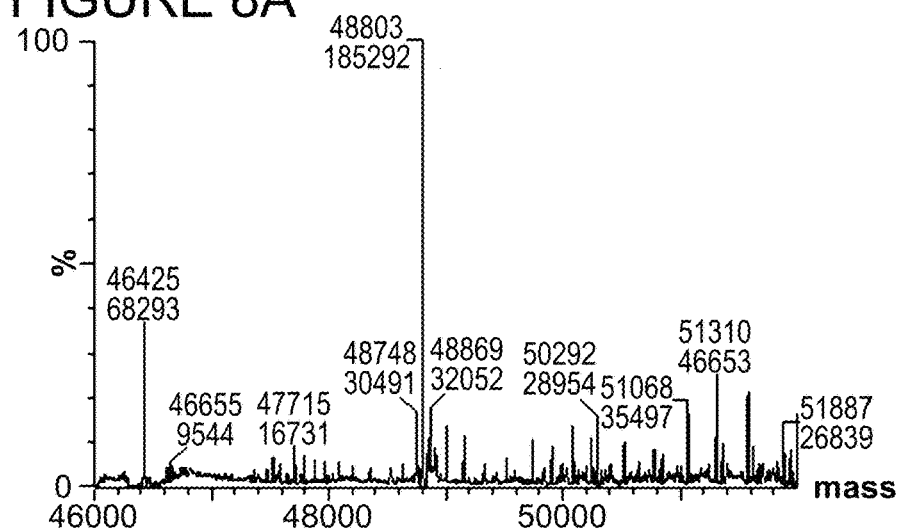
FIGS. 8A, 8B, and 8C, illustrates ESI-MS analysis of C-terminal extensions of Antibody 01. (A) Antibody 01 MAbs, (B) Antibody 01-L, and (C) Antibody 01-LL were incubated with Z-Gln-Gly-CAD-biotin and microbial transglutaminase overnight at 37° C. and the masses were analyzed by ESI-MS as in FIG. 7.
Figure 8B:
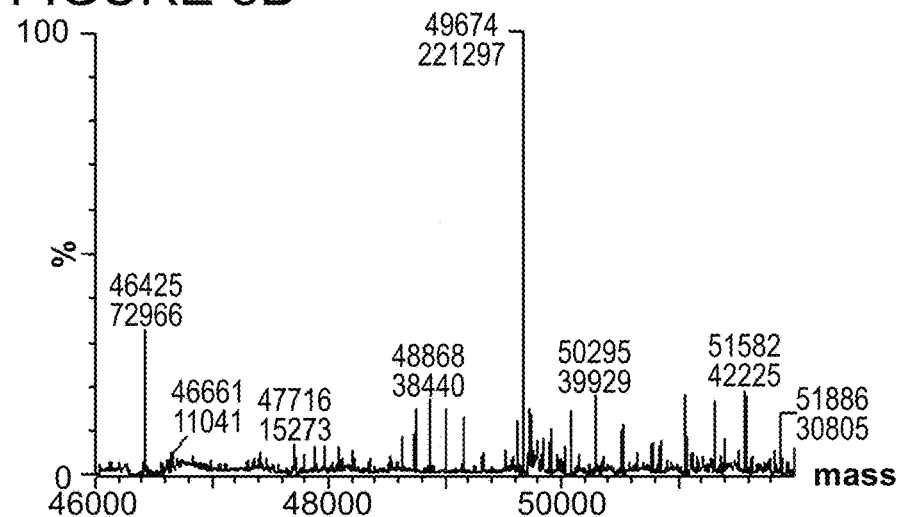
Figure 8C:
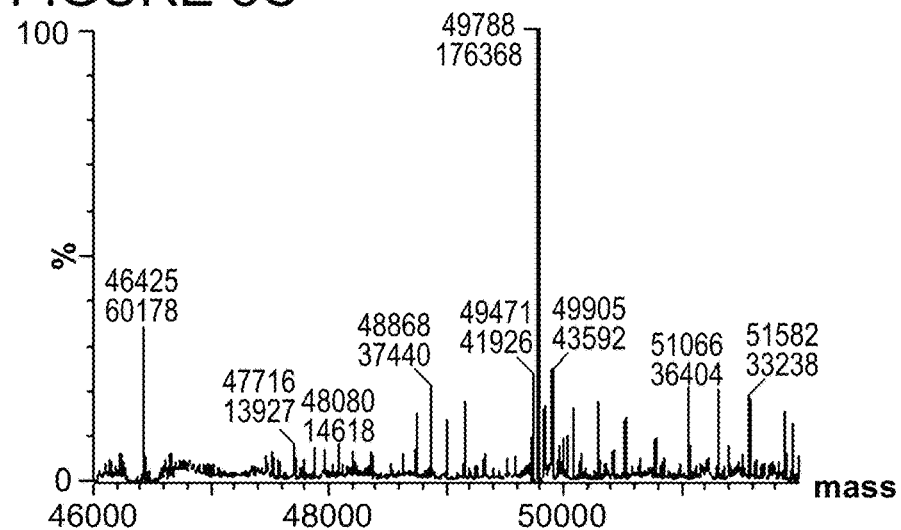

Lys447 is typically cleaved by carboxypeptidase B during recombinant IgG expression in HEK293 and CHO cells {Harris, 1990 7/id; Harris, 1995 6/id; Dick, 2008 3/id}. However, addition of the KTag to the HC C terminus blocks removal of Lys447 thereby allowing microbial transglutaminase to utilize Lys447 as an acyl acceptor site. To determine whether microbial transglutaminase could utilize Lys447 as an acyl acceptor without a KTag, the cleavage of Lys447 was blocked by the addition of one or two leucines at the C terminus of Antibody 01 (Antibody 01-HC-L or Antibody 01-HC-LL, respectively). Purified mAbs were incubated with Z-Gln-Gly-CAD-biotin and microbial transglutaminase and the mass of the deglycosylated HC was analyzed. Indeed, the addition of either one or two leucines retained Lys447, and the HC was modified with a single acyl donor substrate consistent with transamidation of Lys447 (FIG. 8; Table 3).

TABLE 3

Transamidation of Antibody 01 with a C-terminal leucine

Z-Gln-Gly-CAD-biotin: +631 Da

| C terminus | Calculated | Observed | ΔMass | % conjugated |
|---|---|---|---|---|
| Antibody 01 . . . SPGK (SEQ ID NO: 7) | 48937 | 48803 | -134 | 0.0% |
| Antibody 01-HC-L . . . SPGK-L (SEQ ID NO: 8) | 49050 | 49674 | 624 | 100.0% |
| Antibody 01-HC-LL . . . SPGK-LL (SEQ ID NO: 9) | 49164 | 49788 | 624 | 100.0% |

The masses of the HC and LC were determined by ESI-MS. The percent conjugation of Z-Gln-Gly-CAD-biotin (Δmass=631 Da) to a mAb was determined as in Table 2.

A C-terminal leucine was added to two other mAbs. The wild type and mutant mAbs were incubated with microbial transglutaminase and Z-Gln-Gly-CAD-biotin overnight at 37° C. The Fc fragment of each sample was analyzed by mass spectrometry as above. As with Antibody 01, adding a C-terminal leucine resulted in transamidation of the mutant, but not wild type mAb (Table 4).

TABLE 4

Transamidation of Monoclonal Antibodies with a C-terminal Leucine

Z-Gln-Gly-CAD-biotin: +631 Da

| C terminus | Glycan | Calculated | Observed | ΔMass | % conjugated |
|---|---|---|---|---|---|
| Antibody 10 . . . SPGK (SEQ ID NO: 7) | 25346 | 1445 | 25218 | -128 | 0.0% |
|  | 25509 | 1608 | 25379 | -130 |  |
| Antibody 11 . . . SPGK-L (SEQ ID NO: 8) | 25441 | 1445 | 26071 | 630 | 100.0% |
|  | 25604 | 1608 | 26233 | 629 |  |
| Antibody 12 . . . SPGK (SEQ ID NO: 7) | 25491 | 1608 | 25360 | -131 | 0.0% |
|  | 25653 | 1770 | 25523 | -130 |  |
| Antibody 13 . . . SPGK-L (SEQ ID NO: 8) | 25441 | 1445 | 26071 | 630 | 100.0% |
|  | 25604 | 1608 | 26232 | 628 |  |

MAbs were incubated with Z-Gln-Gly-CAD-biotin and microbial transglutaminase at 37° C. overnight, followed by digestion with IdeS to generate Fab and Fc fragments. The masses of the IdeS-generated Fc fragments were analyzed by ESI-MS as in FIG. 6, and the percent conjugation to Z-Gln-Gly-CAD-biotin (Δmass = 631 Da) was determined as in Table 2.

To determine if other amino acids could block cleavage of Lys447 and if they provided the proper context for microbial transglutaminase to modify Lys447, the remaining amino acids were added as a single-residue extension to the C terminus. The samples were analyzed for modification by microbial transglutaminase using Z-Gln-Gly-CAD-biotin. The mass of the Fc fragment was analyzed by mass spectrometry as above. Not surprisingly, an additional C-terminal lysine or arginine did not protect cleavage of Lys447, as they are substrates for carboxypeptidase B (Table 5). Of the remaining amino acids, only C-terminal proline and acidic residues did not facilitate 100% conjugation to the substrate. In addition to an average +628 Da shift associated with conjugation to Z-Gln-Gly-CAD-biotin (+631 Da), a mass shift of +400 Da was also observed. This is likely due to a small percentage of Z-Gln-Gly-CAD from either the synthesis of Z-Gln-Gly-CAD-biotin or degradation of the latter.

TABLE 5

Effect of C-terminal amino acids on transamidation of Lys447

Z-Gln-Gly-CAD: +404 Da
Z-Gln-Gly-CAD-biotin: +631 Da

| C terminus | Glycan | Calculated | Observed | ΔMass | Percentage | Total Conjugated |
|---|---|---|---|---|---|---|
| . . . SPGK (SEQ ID NO: 7) | G0F | 25328 | 25197 | -131 | 55.1% | 0.0% |
|  | G1F | 25491 | 25360 | -131 | 44.9% |  |

TABLE 5-continued

Effect of C-terminal amino acids on transamidation of Lys447

Z-Gln-Gly-CAD: +404 Da
Z-Gln-Gly-CAD-biotin: +631 Da

| C terminus | Glycan | Calculated | Observed | ΔMass | Percentage | Total Conjugated |
|---|---|---|---|---|---|---|
| . . . SPGK-G (SEQ ID NO: 10) | G0F | 25385 | 26013 | 628 | 31.4% | 100.0% |
|  | G0F | 25385 | 25785 | 400 | 20.2% |  |
|  | G1F | 25548 | 26175 | 627 | 26.9% |  |
|  | G1F | 25548 | 25954 | 406 | 21.6% |  |
| . . . SPGK-A (SEQ ID NO: 11) | G0F | 25399 | 26027 | 628 | 44.3% | 100.0% |
|  | G0F | 25399 | 25800 | 401 | 13.2% |  |
|  | G1F | 25562 | 26189 | 627 | 42.5% |  |
| . . . SPGK-V (SEQ ID NO: 12) | G0F | 25427 | 26055 | 628 | 46.2% | 100.0% |
|  | G0F | 25427 | 25827 | 400 | 15.6% |  |
|  | G1F | 25590 | 26217 | 627 | 38.2% |  |
| . . . SPGK-L (SEQ ID NO: 8) | G0F | 25441 | 26069 | 628 | 64.1% | 100.0% |
|  | G0F | 25441 | 25841 | 400 | 10.6% |  |
|  | G1F | 25604 | 26231 | 627 | 25.3% |  |
| . . . SPGK-I (SEQ ID NO: 13) | G0F | 25441 | 26069 | 628 | 46.4% | 100.0% |
|  | G0F | 25441 | 25841 | 400 | 15.4% |  |
|  | G1F | 25604 | 26232 | 628 | 38.1% |  |
| . . . SPGK-M (SEQ ID NO: 14) | G0F | 25459 | 26087 | 628 | 44.3% | 100.0% |
|  | G0F | 25459 | 25858 | 399 | 13.9% |  |
|  | G1F | 25622 | 26249 | 627 | 41.8% |  |
| . . . SPGK-P (SEQ ID NO: 15) | G0F | 25425 | 25422 | -3 | 36.7% | 37.2% |
|  | G1F | 25588 | 25584 | -4 | 26.1% |  |
|  | G0F | 25425 | 26053 | 628 | 20.1% |  |
|  | G1F | 25588 | 26216 | 628 | 17.0% |  |
| . . . SPGK-F (SEQ ID NO: 16) | G0F | 25475 | 26103 | 628 | 48.1% | 100.0% |
|  | G0F | 25475 | 25875 | 400 | 15.5% |  |
|  | G1F | 25638 | 26265 | 627 | 36.4% |  |
| . . . SPGK-Y (SEQ ID NO: 17) | G0F | 25491 | 26120 | 629 | 50.3% | 100.0% |
|  | G0F | 25491 | 25892 | 401 | 14.5% |  |
|  | G1F | 25654 | 26281 | 627 | 35.1% |  |
| . . . SPGK-W (SEQ ID NO: 18) | G0F | 25514 | 26142 | 628 | 49.4% | 100.0% |
|  | G0F | 25514 | 25915 | 401 | 11.5% |  |
|  | G1F | 25677 | 26304 | 627 | 39.2% |  |
| . . . SPGK-S (SEQ ID NO: 19) | G0F | 25415 | 26044 | 629 | 47.6% | 100.0% |
|  | G0F | 25415 | 25815 | 400 | 14.2% |  |
|  | G1F | 25578 | 26205 | 627 | 38.2% |  |
| . . . SPGK-T (SEQ ID NO: 20) | G0F | 25429 | 26057 | 628 | 47.4% | 100.0% |
|  | G0F | 25429 | 25829 | 400 | 12.8% |  |
|  | G1F | 25592 | 26219 | 627 | 39.8% |  |
| . . . SPGK-C (SEQ ID NO: 21) | G0F | 25431 | 25431 | 0 | 8.4% | 91.6% |
|  | G0F | 25431 | 26062 | 631 | 75.1% |  |
|  | G1F | 25594 | 26224 | 630 | 16.5% |  |
| . . . SPGK-N (SEQ ID NO: 22) | G0F | 25442 | 26070 | 628 | 41.2% | 100.0% |
|  | G0F | 25442 | 25842 | 400 | 16.6% |  |
|  | G1F | 25605 | 26232 | 627 | 42.2% |  |
| . . . SPGK-Q (SEQ ID NO: 23) | G0F | 25456 | 26084 | 628 | 56.3% | 100.0% |
|  | G0F | 25456 | 25856 | 400 | 8.7% |  |
|  | G1F | 25619 | 26246 | 627 | 35.0% |  |
| . . . SPGK-D (SEQ ID NO: 24) | G0F | 25443 | 25441 | -2 | 42.3% | 24.0% |
|  | G1F | 25606 | 25603 | -3 | 33.7% |  |
|  | G0F | 25443 | 26072 | 629 | 12.1% |  |
|  | G1F | 25606 | 26233 | 627 | 11.9% |  |
| . . . SPGK-E (SEQ ID NO: 25) | G0F | 25457 | 25455 | -2 | 28.0% | 34.7% |
|  | G1F | 25620 | 25617 | -3 | 37.3% |  |
|  | G0F | 25457 | 26085 | 628 | 20.3% |  |
|  | G1F | 25620 | 26248 | 628 | 14.4% |  |

TABLE 5-continued

Effect of C-terminal amino acids on transamidation of Lys447

Z-Gln-Gly-CAD: +404 Da
Z-Gln-Gly-CAD-biotin: +631 Da

| C terminus | Glycan | Calculated | Observed | ΔMass | Percentage | Total Conjugated |
|---|---|---|---|---|---|---|
| . . . SPGK-H | G0F | 25465 | 26094 | 629 | 49.2% | 100.0% |
| (SEQ ID NO: 26) | G0F | 25465 | 25865 | 400 | 11.6% | |
| | G1F | 25628 | 26256 | 628 | 39.1% | |
| . . . SPGK-K | G0F | 25456 | 25197 | −259 | 50.6% | 0.0% |
| (SEQ ID NO: 27) | G1F | 25619 | 25359 | −260 | 49.4% | |
| . . . SPGK-R | G0F | 25465 | 25197 | −268 | 53.6% | 0.0% |
| (SEQ ID NO: 28) | G1F | 25628 | 25359 | −269 | 46.4% | |

MAbs were incubated with Z-Gln-Gly-CAD-biotin and microbial transglutaminase at 37° C. overnight, followed by digestion with IdeS to generate Fab and Fc fragments. The masses of the IdeS-generated Fc fragments were analyzed by ESI-MS as in FIG. 6 (data not shown), and the percent conjugation to Z-Gln-Gly-CAD-biotin and Z-Gln-Gly-CAD (Δmass = 631 Da and 404 Da, respectively) was determined as in Table 2.

Due to the cleavage of the addition single lysine or arginine C-terminal amino acid, the effect of either amino acid on transamidation on Lys447 could not be accessed. Therefore, a leucine was added to the C-terminus of the lysine and arginine variants. In addition, the effect an additional C-terminal leucine was also investigated with the proline, aspartate, and glutamate variants. The additional leucine had a positive effect on transamidation of all C-terminal variants tested (Table 6). By blocking cleavage of the lysine or arginine, Lys447 was 100% transamidated. Further, the additional lysine in the KL variant was also transamidated, yielding an antibody with 4 transamidation sites. The C-terminal leucine also increased transamidation of the proline variant to 61.3%, and the acidic residue variants were moderately transamidated (Table 6).

TABLE 6

Effect of two C-terminal amino acids on transamidation of Lys447

Z-Gln-Gly-CAD-biotin: +631 Da

| C terminus | Glycan | Calculated | Observed | ΔMass | Percentage | Total Conjugated |
|---|---|---|---|---|---|---|
| . . . SPGK-L | G0F | 25441 | 26072 | 631 | 77.3% | 100.0% |
| (SEQ ID NO: 8) | G1F | 25604 | 26235 | 631 | 22.7% | |
| . . . SPGK-KL | G0F | 25569 | 26831 | 1262 | 62.0% | 100.0% |
| (SEQ ID NO: 29) | G0F | 25732 | 26993 | 1261 | 38.0% | |
| . . . SPGK-RL | G1F | 25597 | 26229 | 632 | 57.5% | 100.0% |
| (SEQ ID NO: 30) | G1F | 25760 | 26391 | 631 | 42.5% | |
| . . . SPGK-PL | G0F | 25538 | 25538 | 0 | 25.0% | 61.3% |
| (SEQ ID NO: 31) | G0F | 25701 | 25701 | 0 | 13.8% | |
| | G1F | 25538 | 26169 | 631 | 29.1% | |
| | G1F | 25701 | 26332 | 631 | 32.2% | |
| . . . SPGK-DL | G0F | 25556 | 25556 | 0 | 47.8% | 24.0% |
| (SEQ ID NO: 32) | G0F | 25719 | 25719 | 0 | 28.2% | |
| | G1F | 25556 | 26187 | 631 | 11.5% | |
| | G1F | 25719 | 26349 | 630 | 12.5% | |
| . . . SPGK-EL | G0F | 25570 | 25570 | 0 | 40.6% | 28.6% |
| (SEQ ID NO: 33) | G0F | 25733 | 25733 | 0 | 30.7% | |
| | G1F | 25570 | 26203 | 633 | 14.0% | |

Table 6: MAbs were incubated with Z-Gln-Gly-CAD-biotin and microbial transglutaminase at 37° C. overnight, followed by digestion with IdeS to generate Fab and Fc fragments. The masses of the IdeS-generated Fc fragments were analyzed by ESI-MS as in FIG. 6 (data not shown), and the percent conjugation to Z-Gln-Gly-CAD-biotin and Z-Gln-Gly-CAD (Δmass = 631 Da and 404 Da, respectively) was determined as in Table 2.

Example 4: Transamidation of the C-Terminal Lysine of Various Antibody Isotypes

The C-terminal residue of CH3 (or CH4 in the cases of IgE and IgM) is a lysine for all human isotypes (Table 7). Therefore, it is possible that this lysine could be utilized as a conjugation site on other isotypes. $IgG_2$, $IgG_3$, and $IgG_4$ versions of Antibody 01 were made with or without an additional C-terminal leucine or aspartate. The mAbs were incubated with microbial transglutaminase and Z-Gln-Gly-CAD-biotin overnight at 37° C. and the masses of the Fc fragments were analyzed by mass spectrometry as above. As with $IgG_1$, the C-terminal lysines were removed during expression in HEK293 cells unless there was an additional C-terminal residue (Table 8). No transamidation was seen with wild-type $IgG_2$, $IgG_3$, or $IgG_4$ or with a C-terminal aspartate, but a C-terminal leucine facilitated transamidation of the mAbs.

TABLE 7

Alignment of CH3 or CH4 C-terminal codons of different human isotypes

| | |
|---|---|
| IgG1 | . . . LSLSPGK*(SEQ ID NO: 34) |
| IgG2 | . . . LSLSPGK*(SEQ ID NO: 34) |
| IgG3 | . . . LSLSPGK*(SEQ ID NO: 34) |
| IgG4 | . . . LSLSLGK*(SEQ ID NO: 35) |
| IgA₁&₂ | . . . IDRLAGKPTH. . . (SEQ ID NO: 36) |
| IgD | . . . VSVNPGK*(SEQ ID NO: 37) |
| IgE | . . . TDHGPMK*(SEQ ID NO: 38) |
| IgM | . . . VDKSTGKPTL. . . (SEQ ID NO: 39) |

The C-terminal codons of CH3 (CH4 for IgE and IgM) were aligned. The three N-terminal codons of the tailpiece of IgA and IgM were included.

TABLE 8

Transamidation of IgG2, IgG3, and IgG4 with a C-terminal leucine

Z-Gln-Gly-CAD-biotin: +631 Da

| C terminus | | Glycan | Calculated | Observed | ΔMass | % conjugated |
|---|---|---|---|---|---|---|
| $IgG_2$ | . . . SPGK (SEQ ID NO: 7) | G0F | 25362 | 25232 | -130 | 0.0% |
| | | G1F | 25525 | 25394 | -131 | |
| $IgG_2$-L | . . . SPGK-L (SEQ ID NO: 8) | G0F | 25475 | 26104 | 629 | 100.0% |
| | | G1F | 25638 | 26266 | 628 | |
| $IgG_2$-D | . . . SPGK-D (SEQ ID NO: 24) | G0F | 25477 | 25475 | -2 | 23.2% |
| | | G1F | 25640 | 25637 | -3 | |
| | | G0F | 25477 | 26106 | 629 | |
| | | G1F | 25640 | 26268 | 628 | |
| $IgG_3$ | . . . SPGK (SEQ ID NO: 7) | G0F | 25396 | 25266 | -130 | 0.0% |
| | | G1F | 25559 | 25428 | -131 | |
| $IgG_3$-L | . . . SPGK-L (SEQ ID NO: 8) | G0F | 25509 | 26138 | 629 | 100.0% |
| | | G1F | 25672 | 26300 | 628 | |
| $IgG_3$-D | . . . SPGK-D (SEQ ID NO: 24) | G0F | 25511 | 25509 | -2 | 24.7% |
| | | G1F | 25674 | 25671 | -3 | |
| | | G0F | 25511 | 26140 | 629 | |
| | | G1F | 25674 | 26302 | 628 | |
| $IgG_4$ | . . . SPGK (SEQ ID NO: 7) | G0F | 25344 | 25214 | -130 | 0.0% |
| | | G1F | 25507 | 25376 | -131 | |
| $IgG_4$-L | . . . SLGK-L (SEQ ID NO: 8) | G0F | 25457 | 25455 | -2 | 81.9% |
| | | G1F | 25620 | 25616 | -4 | |
| | | G0F | 25457 | 26086 | 629 | |
| | | G1F | 25620 | 26248 | 628 | |
| $IgG_4$-D | . . . SPGK-D (SEQ ID NO: 24) | G0F | 25459 | 25457 | -2 | 16.8% |
| | | G1F | 25622 | 25619 | -3 | |
| | | G0F | 25459 | 26087 | 629 | |
| | | G1F | 25622 | 26250 | 628 | |

MAbs were incubated with Z-Gln-Gly-CAD-biotin and microbial transglutaminase at 37° C. overnight, followed by digestion with IdeS to generate Fab and Fc fragments. The masses of the IdeS-generated Fc fragments were analyzed by ESI-MS as in FIG. 6 (data not shown), and the percent conjugation to Z-Gln-Gly-CAD-biotin (Δmass = 631 Da) was determined as in Table 2.

Example 5: Acyl Donor Substrates

One utility of conjugations to the C-terminal lysine is for the manufacturing of site-specific ADCs. Conjugation of functional agents to the C-terminal lysine could be achieved by one of two methods. First, a 2-step method would require microbial transglutaminase conjugation of the C-terminally lysine to an acyl donor synthesized with a reactive group such as BCN, DBCO, TCO, azido ($N_3$), alkyne, tetrazine, or maleimide. The second step would involve conjugation of a functional agent to the reactive group using, for example, copper-free click chemistry or thiol-reactive chemistry. Therefore, amino-PEG3-BCN or aminopropyl-$N_3$ was added to the hydroxyl group of Z-Gln-Gly as detailed in the Methods section. Antibody 01-HC-L was incubated with Z-Gln-Gly, Z-Gln-Gly-CAD-biotin, Z-Gln-Gly-$N_3$, or Z-Gln-Gly-PEG3-BCN and microbial transglutaminase as above. The samples were desalted, deglycosylated, reduced, and analyzed by ESI-MS to determine addition of the substrate to the mAb. All four substrates were efficiently conjugated to the Antibody 01-HC-L (Table 9).

TABLE 9

Conjugation of various functional groups onto Lys447

| | Da | Calculated | Observed | ΔMass | Percentage |
|---|---|---|---|---|---|
| Z-Gln-Gly-$N_3$ | +402 | 49050 | 49048 | −2 | 9.2% |
| | | 49050 | 49447 | 397 | 90.8% |
| Z-Gln-Gly-PEG$_3$-BCN | +670 | 49050 | 49717 | 667 | 100.0% |
| Z-Gln-Gly | +320 | 49050 | 49047 | −3 | 1.9% |
| | | 49050 | 49367 | 317 | 98.1% |
| Z-Gln-Gly-CAD-biotin | +631 | 49050 | 49047 | −3 | 22.8% |
| | | 49050 | 49677 | 627 | 77.2% |

MAbs were incubated with Z-Gln-Gly-CAD-biotin and microbial transglutaminase at 37° C. overnight, followed by digestion with IdeS to generate Fab and Fc fragments. The masses of the IdeS-generated Fc fragments were analyzed by ESI-MS as in FIG. 6 (data not shown), and the percent conjugation to the various substrates was determined as in Table 2.

Figure 9A:
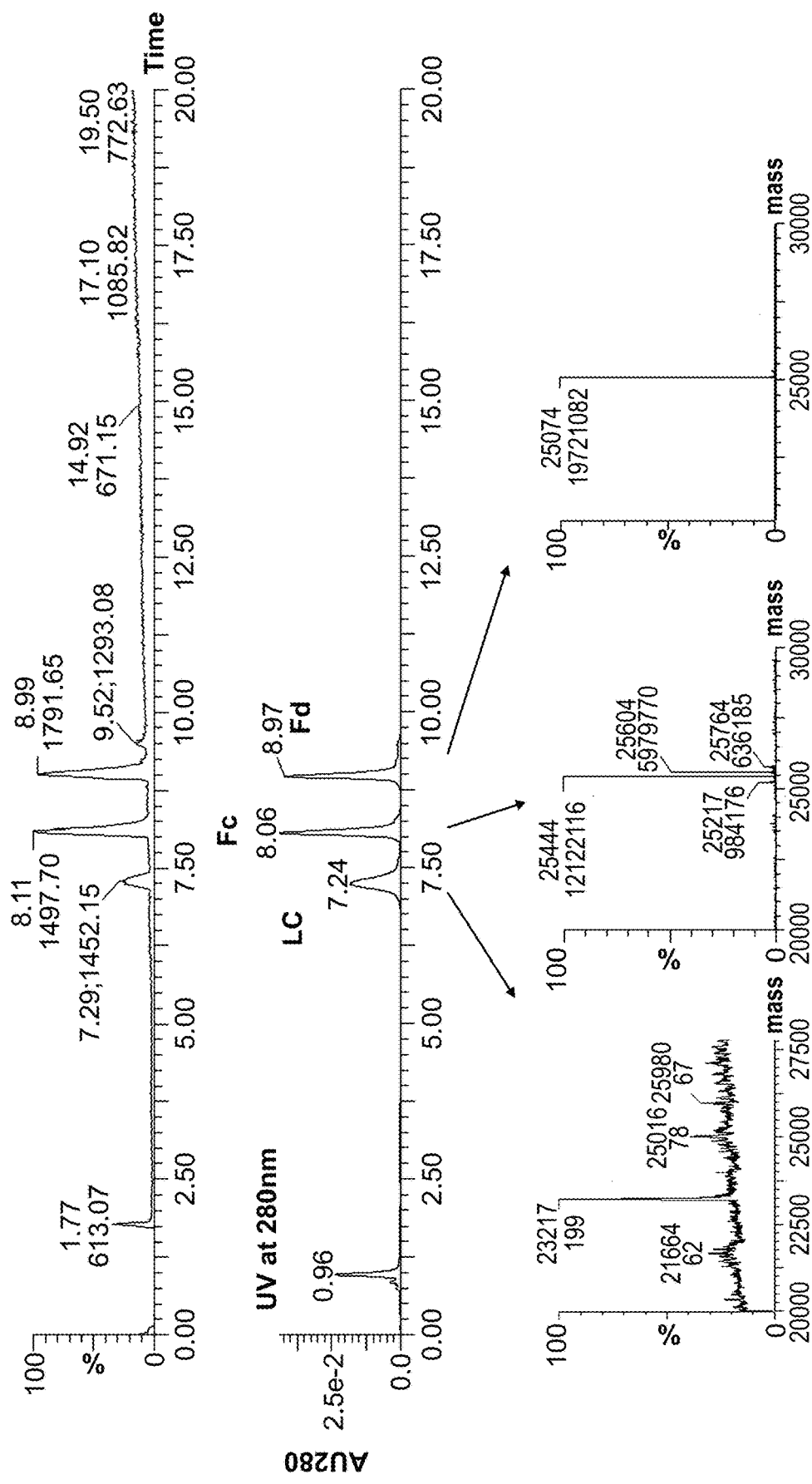
FIGS. 9A-9B, illustrates single-step drug conjugation to Lys447. (A) Antibody 01-L and (B) Antibody 01-L incubated with Z-Gln-Gly-PEG₂-AuF and microbial transglutaminase at 37° C. overnight were digestion with IdeS and reduction with DTT to generate LC, Fd, and Fc fragments. The absorbance at 280 nm (AU280) and total ion current (TIC) of the samples were monitored by reverse phase LC-MS as in the Methods.
Figure 9B:
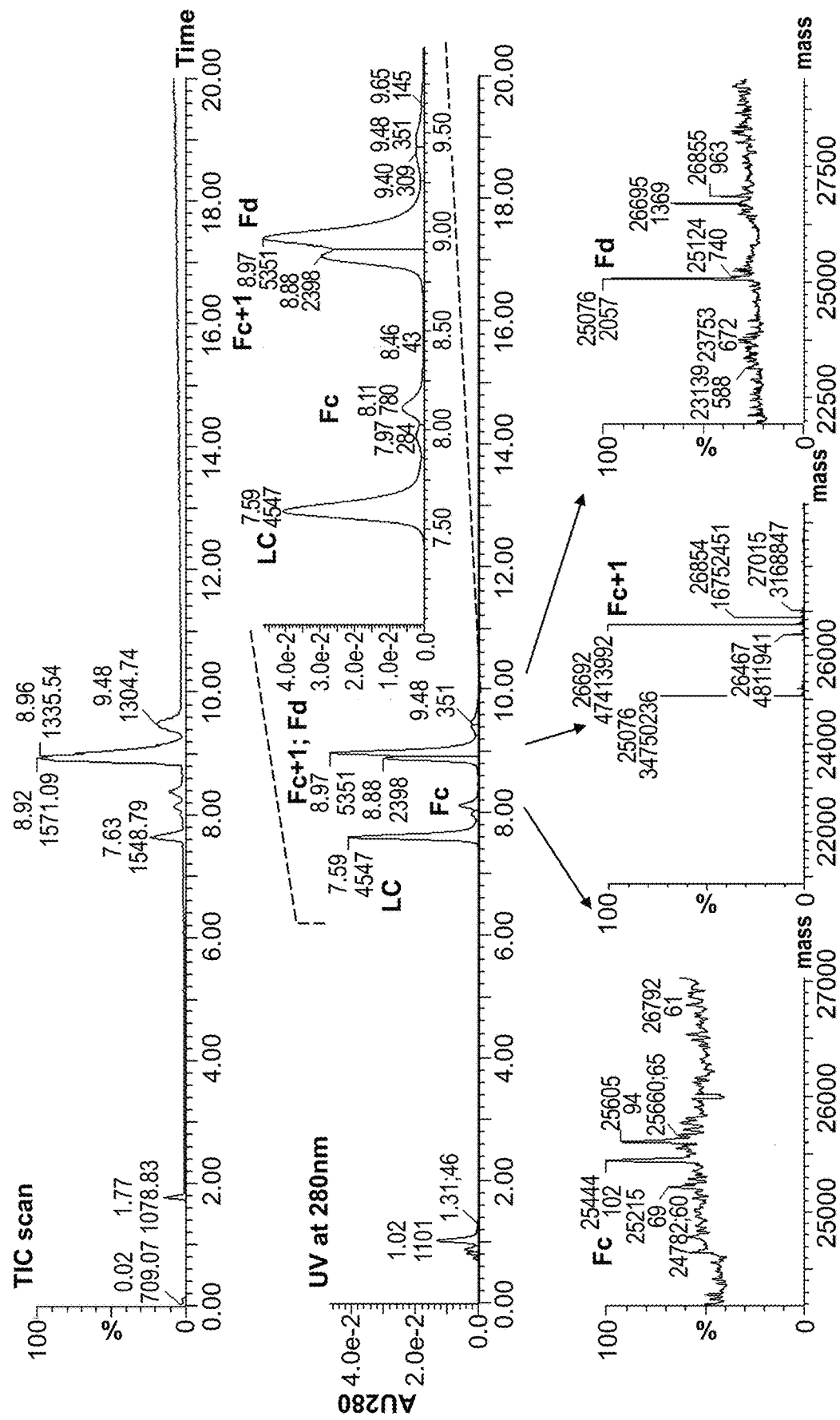

A second method involves a single conjugation step whereby a functional agent is synthesized with an acyl donor group. This method was tested by synthesizing a Z-Gln-Gly group onto PEG2-Auristatin F (Z-Gln-Gly-PEG2-AuF). The Z-Gln-Gly-PEG2-AuF was incubated with Antibody 01-L and microbial transglutaminase overnight at 37° C. Following digestion with IdeS and reduction by DTT, the absorbance at 280 nm was monitored was analyzed by reverse phase LC-MS. Three peaks were observed for Antibody 01-L (FIG. 9). The mass of each peak was analyzed by ESI-MS, and the first peak was determined to be the LC, the second was the Fc, and the third was the Fd. A fourth peak was observed for Antibody 01-L incubated with Z-Gln-Gly-PEG2-AuF and microbial transglutaminase. Although this peak could not be completely separated from the Fd peak, the area of majority of the peak (FIG. 9B, inset) was determined to be 75.4% of the total area of the Fc and Fc-Z-Gln-Gly-PEG$_2$-AuF peaks (Table 10). Therefore, a DAR of greater than 1.58 was achieved.

TABLE 10

Single-step conjugation of Auristatin F onto Lys447

| | Peak Area | | | | |
|---|---|---|---|---|---|
| Compound | Fc | Fc + compound | Total | % compound/Fc | DAR |
| Z-Gln-Gly-PEG2-AuF | 780 | 2398 | 3178 | 75.4 | 1.5 |

MAbs were incubated with acyl donor substrates and microbial transglutaminase at 37° C. overnight, followed by digestion with IdeS and reduction with DTT to generate LC, Fc, and Fd fragments. The percent conjugation was calculated by dividing the UV 280 peak area of the Fc + compound by the total area of the Fc and Fc + compound peaks in FIG. 9.

Example 6: Generation of Dimeric Antibody Molecules

Figure 10:
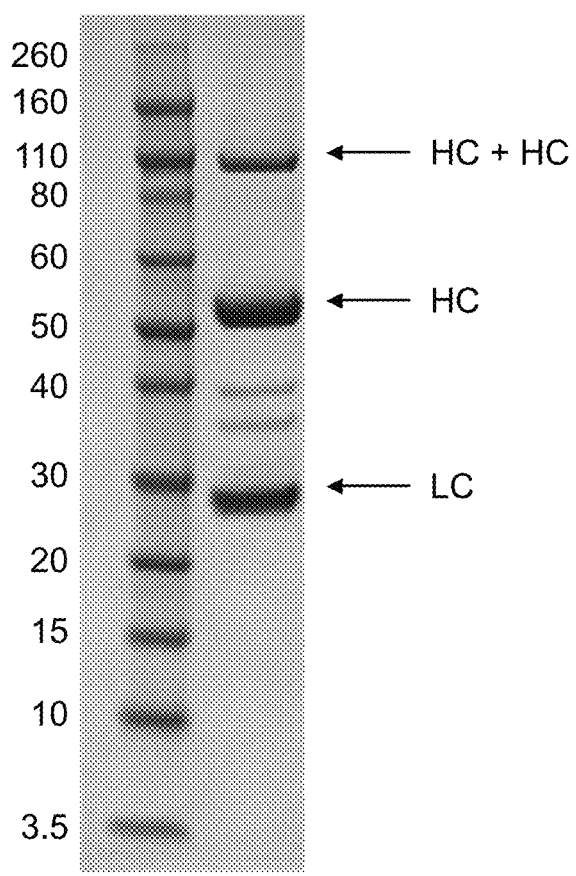
FIG. 10, shows SDS-PAGE of dimeric mAbs. Antibody 01-L transamidated with either Z-Gln-Gly-N₃ or Z-Gln-Gly-PEG₃-BCN were mixed and incubated overnight at 22° C. The samples were reduced and analyzed by SDS-PAGE using a 4-12% Bis-Tris polyacrylamide gel. The mass of the HC-HC dimer is approximately 110 kDa.

Another utility of the addition of functional groups onto the C-terminal lysine of an immunoglobulin is the generation of dimeric mAb-mAb molecules. For example, a BCN-conjugated mAb may be conjugated to an $N_3$-conjugated mAb using copper-free click chemistry. Therefore, equal volumes of the Z-Gln-Gly-N3 or Z-Gln-Gly-PEG3-BCN Antibody 01-HC-L reactions were mixed and allowed to incubate overnight at 22° C. The reduced reaction was analyzed for dimerized HC (~110 kDa) by SDS-PAGE using a 4-12% Bis-Tris polyacrylamide gel (FIG. 10). Indeed, heavy chains modified with BCN and N3 formed dimeric heavy chain molecules.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A conjugated immunoglobulin comprising an immunoglobulin and an acyl donor substrate, wherein
   a1) the immunoglobulin comprises one amino acid residue or two amino acid residues after Lysine 447 (K447) on a heavy chain constant region of the immunoglobulin, wherein the amino acid residues are numbered according to the EU numbering system, and wherein, when the immunoglobulin comprises one amino acid residue after K447, the one amino acid residue after the K447 is selected from the group consisting of glycine, alanine, valine, leucine, isoleucine, methionine, phenylalanine, tyrosine, tryptophan, serine, threonine, cysteine, asparagine, glutamine, and histidine; and when the immunoglobulin comprises two amino acid residues after K447, the first amino acid residue after the K447 is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine and the second amino acid residue after the K447 is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan and glycine, and
   b1) the acyl donor substrate comprises a glutamine residue and a therapeutic or a diagnostic agent, wherein the K447 of the immunoglobulin is conjugated to the glutamine residue of the acyl donor substrate, wherein the acyl donor substrate is according to one of Formulae (I) or (II):

$(Z)_m$-Gln-$(L)_n$-(Y)     (I)

(Y)-$(L)_n$-Gln-$(Z)_m$     (II)

wherein
   Z is a carboxylbenzyloxy (CBZ) group or an amino acid residue;
   Gln is a glutamine amino acid residue;
   each L is independently a straight or branched linker from 1 to 20 carbon atoms, wherein one or more of the carbon atoms is optionally and independently replaced with a nitrogen, oxygen or sulfur atom, and wherein each carbon and nitrogen atom is optionally substituted;
   or each L is optionally and independently an amino acid residue;
   m is an integer from 0 to 5;
   n is an integer from 0 to 5; and
   Y is a therapeutic or a diagnostic agent;
   or wherein:
   a2) the immunoglobulin comprises at one amino acid residue or two amino acid residues after Lysine 447 (K447) on a heavy chain of the constant region of the immunoglobulin, wherein the amino acid residues are numbered according to the EU numbering system, and wherein, when the immunoglobulin comprises one amino acid residue after K447, the one amino acid residue after the K447 is selected from the group consisting of glycine, alanine, valine, leucine, isoleucine, methionine, phenylalanine, tyrosine, tryptophan, serine, threonine, cysteine, asparagine, glutamine, and histidine; and when the immunoglobulin comprises two amino acid residue after K447, the first amino acid residue after the K447 is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine and the second amino acid residue after the K447 is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan and glycine, b2) the K447 of the immunoglobulin is conjugated to a glutamine residue on an acyl donor substrate, wherein the acyl donor substrate further comprises a reactive group, wherein the acyl donor substrate is according to one of Formulae (III) or (IV):

$$(Z)_m\text{-Gln-}(L)_n\text{-}(X) \tag{III}$$

$$(X)\text{-}(L)_n\text{-Gln-}(Z)_m \tag{IV}$$

wherein

Z is a carboxylbenzyloxy (CBZ) group or an amino acid residue;

Gln is a glutamine amino acid residue;

each L is independently a straight or branched linker from 1 to 20 carbon atoms, wherein one or more of the carbon atoms is optionally and independently replaced with a nitrogen, oxygen or sulfur atom, and wherein each carbon and nitrogen atom is optionally substituted;

or each L is optionally and independently an amino acid residue;

m is an integer from 0 to 5;

n is an integer from 0 to 5; and

X is a reactive group; and c2) the reactive group is conjugated to a therapeutic agent or a diagnostic agent.

2. The conjugated immunoglobulin of claim 1, wherein the immunoglobulin comprises one amino acid residue after K447.

3. The conjugated immunoglobulin of claim 1, wherein the acyl donor substrate:
(i) is according to formula (I), and wherein Z is a CBZ group; wherein L is a polyethylene glycol moiety (PEG) (—O((CH$_2$)$_2$)-), ethyl amine (—NH((CH$_2$)$_2$)-) or propyl amine (—NH((CH$_2$)$_3$)-); and wherein n is 0, 1, 2, 3, 4 or 5; or
(ii) is according to formula (I), wherein Z is a CBZ group, and wherein L is an amino acid; or
(iii) is according to formula (II), wherein Z is a CBZ group; m is 1; n is 1, 2 or 3; and at least one L is Gly.

4. The conjugated immunoglobulin of claim 1, wherein the acyl donor substrate:
(i) is according to formula (III), and wherein Z is a CBZ group; wherein each L is independently a polyethylene glycol moiety (PEG) (—O((CH$_2$)$_2$)-), ethyl amine (—NH((CH$_2$)$_2$)-) or propyl amine (—NH((CH$_2$)$_3$)-); and wherein n is 0, 1, 2, 3, 4 or 5; or
(ii) is according to formula (III), wherein Z is a CBZ group, and wherein L is an amino acid; or
(iii) is according to formula (IV), wherein Z is a CBZ group; m is 1; n is 1, 2 or 3; and at least one L is Gly.

5. The conjugated immunoglobulin of claim 1, wherein X is a reactive group selected from the group consisting of (1R,8S,9s)-bicyclo[6.1.0]non-4-yn-9-ylmethanol (BCN),

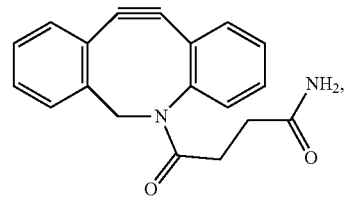
(DBCO)

trans-cyclooctene (TCO), azido (N3), alkyne, tetrazine methylcyclopropene, norbornene, hydrazide/hydrazine, and aldehyde.

6. The conjugated immunoglobulin of claim 1, wherein the therapeutic agent is an antibody or antigen-binding portion thereof, a chemotherapeutic agent, a drug agent, a radioactive agent, a cytotoxic agent, an antibiotic, a small molecule, nucleic acid, or a polypeptide; or
wherein the diagnostic agent is a fluorophore, a fluorescent dye, a radionuclide, or an enzyme.

7. The conjugated immunoglobulin of claim 1, wherein the immunoglobulin has two amino acid residues after the K447, comprising a first amino acid residue after the K447 and a second amino acid residue after the K447.

8. The conjugated immunoglobulin of claim 1, wherein the immunoglobulin:
(i) is an IgG$_1$ immunoglobulin; or
(ii) is an IgG$_2$, IgG$_3$, or IgG$_4$ immunoglobulin; or
(iii) is an IgA$_1$, an IgA$_2$, or an IgM immunoglobulin; or
(iv) is an IgD or IgE, immunoglobulin; or
(v) is a human immunoglobulin or a humanized immunoglobulin; or
(vi) is a chimeric immunoglobulin or a non-human immunoglobulin; or
(vii) comprises two heavy chain and two light chains.

9. The conjugated immunoglobulin of claim 1, wherein the therapeutic or the diagnostic agent is an antibody, or antigen-binding portion thereof, and wherein the immunoglobulin and the therapeutic or the diagnostic agent bind the same antigen or bind different antigens.

10. A composition comprising the conjugated immunoglobulin of claim 1, and a pharmaceutically acceptable carrier.

11. A method for generating the conjugated immunoglobulin of claim 1, the method comprising:
incubating an immunoglobulin with a microbial transglutaminase and an acyl donor substrate,
a1) wherein the immunoglobulin comprises one amino acid residue or two amino acid residues after Lysine 447 (K447) on a heavy chain of the constant region of the immunoglobulin, wherein the amino acid residues are numbered according to the EU numbering system, and wherein, when the immunoglobulin comprises one amino acid residue after K447, the one amino acid residue after the K447 is selected from the group consisting of glycine, alanine, valine, leucine, isoleucine, methionine, phenylalanine, tyrosine, tryptophan, serine, threonine, cysteine, asparagine, glutamine, and histidine; and when the immunoglobulin comprises two amino acid residues after K447, the first amino acid residue after the K447 is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine and the second amino acid residue after the K447 is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan and glycine, b1) wherein the acyl donor substrate comprises a glutamine residue and a therapeutic agent or a diagnostic agent, wherein the acyl donor substrate is according to one of Formulae (I) or (II):

$$(Z)_m\text{-Gln-}(L)_n\text{-}(Y) \qquad (I)$$

$$(Y)\text{-}(L)_n\text{-Gln-}(Z)_m \qquad (II)$$

wherein

Z is a carboxylbenzyloxy (CBZ) group or an amino acid residue;

Gln is a glutamine amino acid residue;

each L is independently a straight or branched linker from 1 to 20 carbon atoms, wherein one or more of the carbon atoms is optionally and independently replaced with a nitrogen, oxygen or sulfur atom, and wherein each carbon and nitrogen atom is optionally substituted;

or each L is optionally and independently an amino acid residue;

m is an integer from 0 to 5;

n is an integer from 0 to 5; and

Y is a therapeutic or a diagnostic agent; and wherein the microbial transglutaminase conjugates the K447 of the immunoglobulin to the glutamine residue of the acyl donor substrate, thereby generating the conjugated immunoglobulin;

or (i) incubating an immunoglobulin with a microbial transglutaminase and an acyl donor substrate, a2) wherein the immunoglobulin comprises one amino acid residue or two amino acid residues after the Lysine 447 (K447) on a heavy chain of the constant region of the immunoglobulin, wherein the amino acid residues are numbered according to the EU numbering system, and wherein, when the immunoglobulin comprises one amino acid residue after K447, the one amino acid residue after the K447 is selected from the group consisting of glycine, alanine, valine, leucine, isoleucine, methionine, phenylalanine, tyrosine, tryptophan, serine, threonine, cysteine, asparagine, glutamine, and histidine; and when the immunoglobulin comprises two amino acid residues after K447, the first amino acid residue after the K447 is selected from the group consisting of phenylalanine, leucine, isoleucine, methionine, valine, serine, threonine, alanine, tyrosine, histidine, glutamine, asparagine, lysine, cysteine, tryptophan, arginine, serine, and glycine and the second amino acid residue after the K447 is selected from the group consisting of phenylalanine, leucine, isoleucine, methionine, valine, serine, proline, threonine, alanine, tyrosine, histidine, glutamine, asparagine, aspartic acid, glutamic acid, cysteine, tryptophan and glycine, and b2) wherein the acyl donor substrate comprises a glutamine residue and a reactive group, wherein the acyl donor substrate is according to one of Formulae (III) or (IV):

$$(Z)_m\text{-Gln-}(L)_n\text{-}(X) \qquad (III)$$

$$(X)\text{-}(L)_n\text{-Gln-}(Z)_m \qquad (IV)$$

wherein

Z is a carboxylbenzyloxy (CBZ) group or an amino acid residue;

Gln is a glutamine amino acid residue;

each L is independently a straight or branched linker from 1 to 20 carbon atoms, wherein one or more of the carbon atoms is optionally and independently replaced with a nitrogen, oxygen or sulfur atom, and wherein each carbon and nitrogen atom is optionally substituted;

or each L is optionally and independently an amino acid residue;

m is an integer from 0 to 5;

n is an integer from 0 to 5; and

X is a reactive group;

wherein the microbial transglutaminase conjugates the K447 of the immunoglobulin to the glutamine residue of the acyl donor substrate, and (ii) conjugating a therapeutic or diagnostic agent to the reactive group of the acyl donor substrate, thereby generating the conjugated immunoglobulin.

12. The method of claim 11, wherein the reactive group of the acyl donor substrate is conjugated to the therapeutic or diagnostic agent by click chemistry.

13. The method of claim 11, wherein the microbial transglutaminase is a *Streptomyces mobarensis* microbial transglutaminase.

* * * * *

SEQUENCE LISTING

```
<160> NUMBER OF SEQ ID NOS: 42

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gly Thr Tyr Phe Gln Ala Tyr Gly Thr
1               5
```

<210> SEQ ID NO 2
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gly Glu Cys Thr Tyr Phe Gln Ala Tyr Gly Cys Thr Glu
1               5                   10

<210> SEQ ID NO 3
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Glu Asn Thr Tyr Phe Gln Ala Tyr Gly Asn Thr Glu
1               5                   10

<210> SEQ ID NO 4
<211> LENGTH: 18
<212> TYPE: PRT
<213> ORGANISM: Homo sapiens

<400> SEQUENCE: 4

Pro Thr His Val Asn Val Ser Val Val Met Ala Glu Val Asp Gly Thr
1               5                   10                  15

Cys Tyr

<210> SEQ ID NO 5
<211> LENGTH: 18
<212> TYPE: PRT
<213> ORGANISM: Homo sapiens

<400> SEQUENCE: 5

Pro Thr Leu Tyr Asn Val Ser Leu Val Met Ser Asp Thr Ala Gly Thr
1               5                   10                  15

Cys Tyr

<210> SEQ ID NO 6
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Ser Thr Lys His Lys Ile Pro Gly Gly Ser
1               5                   10

<210> SEQ ID NO 7
<211> LENGTH: 4
<212> TYPE: PRT
<213> ORGANISM: Homo sapiens

<400> SEQUENCE: 7

```
Ser Pro Gly Lys
1

<210> SEQ ID NO 8
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Ser Pro Gly Lys Leu
1               5

<210> SEQ ID NO 9
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Pro Gly Lys Leu Leu
1               5

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ser Pro Gly Lys Gly
1               5

<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Pro Gly Lys Ala
1               5

<210> SEQ ID NO 12
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ser Pro Gly Lys Val
1               5
```

```
<210> SEQ ID NO 13
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Ser Pro Gly Lys Ile
1               5

<210> SEQ ID NO 14
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Pro Gly Lys Met
1               5

<210> SEQ ID NO 15
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Ser Pro Gly Lys Pro
1               5

<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Ser Pro Gly Lys Phe
1               5

<210> SEQ ID NO 17
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ser Pro Gly Lys Tyr
1               5

<210> SEQ ID NO 18
<211> LENGTH: 5
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Ser Pro Gly Lys Trp
1               5

<210> SEQ ID NO 19
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ser Pro Gly Lys Ser
1               5

<210> SEQ ID NO 20
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Pro Gly Lys Thr
1               5

<210> SEQ ID NO 21
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Ser Pro Gly Lys Cys
1               5

<210> SEQ ID NO 22
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Pro Gly Lys Asn
1               5

<210> SEQ ID NO 23
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 23

Ser Pro Gly Lys Gln
1               5

<210> SEQ ID NO 24
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ser Pro Gly Lys Asp
1               5

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ser Pro Gly Lys Glu
1               5

<210> SEQ ID NO 26
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ser Pro Gly Lys His
1               5

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ser Pro Gly Lys Lys
1               5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

```
Ser Pro Gly Lys Arg
1               5

<210> SEQ ID NO 29
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Pro Gly Lys Lys Leu
1               5

<210> SEQ ID NO 30
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ser Pro Gly Lys Arg Leu
1               5

<210> SEQ ID NO 31
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ser Pro Gly Lys Pro Leu
1               5

<210> SEQ ID NO 32
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Ser Pro Gly Lys Asp Leu
1               5

<210> SEQ ID NO 33
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Pro Gly Lys Glu Leu
1               5
```

```
<210> SEQ ID NO 34
<211> LENGTH: 7
<212> TYPE: PRT
<213> ORGANISM: Homo sapiens

<400> SEQUENCE: 34

Leu Ser Leu Ser Pro Gly Lys
1               5

<210> SEQ ID NO 35
<211> LENGTH: 7
<212> TYPE: PRT
<213> ORGANISM: Homo sapiens

<400> SEQUENCE: 35

Leu Ser Leu Ser Leu Gly Lys
1               5

<210> SEQ ID NO 36
<211> LENGTH: 10
<212> TYPE: PRT
<213> ORGANISM: Homo sapiens

<400> SEQUENCE: 36

Ile Asp Arg Leu Ala Gly Lys Pro Thr His
1               5                   10

<210> SEQ ID NO 37
<211> LENGTH: 7
<212> TYPE: PRT
<213> ORGANISM: Homo sapiens

<400> SEQUENCE: 37

Val Ser Val Asn Pro Gly Lys
1               5

<210> SEQ ID NO 38
<211> LENGTH: 7
<212> TYPE: PRT
<213> ORGANISM: Homo sapiens

<400> SEQUENCE: 38

Thr Asp His Gly Pro Met Lys
1               5

<210> SEQ ID NO 39
<211> LENGTH: 10
<212> TYPE: PRT
<213> ORGANISM: Homo sapiens

<400> SEQUENCE: 39

Val Asp Lys Ser Thr Gly Lys Pro Thr Leu
1               5                   10

<210> SEQ ID NO 40
<211> LENGTH: 330
<212> TYPE: PRT
<213> ORGANISM: Homo sapiens

<400> SEQUENCE: 40

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

-continued

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 41
<211> LENGTH: 107
<212> TYPE: PRT
<213> ORGANISM: Homo sapiens

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

```
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 42
<211> LENGTH: 106
<212> TYPE: PRT
<213> ORGANISM: Homo sapiens

<400> SEQUENCE: 42

Gly Gln Pro Lys Ala Ala Pro Ser Val Thr Leu Phe Pro Pro Ser Ser
1               5                   10                  15
Glu Glu Leu Gln Ala Asn Lys Ala Thr Leu Val Cys Leu Ile Ser Asp
                20                  25                  30
Phe Tyr Pro Gly Ala Val Thr Val Ala Trp Lys Ala Asp Ser Ser Pro
            35                  40                  45
Val Lys Ala Gly Val Glu Thr Thr Thr Pro Ser Lys Gln Ser Asn Asn
50                  55                  60
Lys Tyr Ala Ala Ser Ser Tyr Leu Ser Leu Thr Pro Glu Gln Trp Lys
65                  70                  75                  80
Ser His Lys Ser Tyr Ser Cys Gln Val Thr His Glu Gly Ser Thr Val
                85                  90                  95
Glu Lys Thr Val Ala Pro Thr Glu Cys Ser
            100                 105
```